(12) United States Patent
Altshuler et al.

(10) Patent No.: US 7,942,916 B2
(45) Date of Patent: May 17, 2011

(54) PHOTOTREATMENT DEVICE FOR USE WITH COOLANTS AND TOPICAL SUBSTANCES

(75) Inventors: Gregory B. Altshuler, Lincoln, MA (US); Ilya Yaroslavsky, North Andover, MA (US); James Burke, III, Londonderry, NH (US); Andrei V. Erofeev, North Andover, MA (US); Henry Zenzie, Dover, MA (US); Robert R. Lopez, Boxford, MA (US); Christopher Gaal, Mansfield, MA (US)

(73) Assignee: Palomar Medical Technologies, Inc., Burlington, MA (US)

( * ) Notice: Subject to any disclaimer, the term of this patent is extended or adjusted under 35 U.S.C. 154(b) by 1117 days.

(21) Appl. No.: 11/607,551

(22) Filed: Dec. 1, 2006

(65) Prior Publication Data
US 2007/0078501 A1    Apr. 5, 2007

Related U.S. Application Data

(63) Continuation of application No. 11/598,412, filed on Nov. 13, 2006, which is a continuation of application No. 10/693,682, filed on Oct. 23, 2003, now Pat. No. 7,135,033, and a continuation-in-part of application No. 10/154,756, filed on May 23, 2002, now Pat. No. 7,204,832.

(60) Provisional application No. 60/420,645, filed on Oct. 23, 2002, provisional application No. 60/498,258, filed on Aug. 25, 2003.

(51) Int. Cl.
*A61N 5/067* (2006.01)
(52) U.S. Cl. .................. 607/88; 607/89; 607/90; 606/1; 606/9

(58) Field of Classification Search .................. 606/1, 4, 606/5, 9–26; 607/88–90
See application file for complete search history.

(56) References Cited

U.S. PATENT DOCUMENTS
853,033 A    5/1907   Roberts
(Continued)

FOREIGN PATENT DOCUMENTS
AT         400305        4/1995
(Continued)

OTHER PUBLICATIONS
Office Action dated Nov. 23, 2009 for Canadian Patent Application No. 2,501,098.
(Continued)

*Primary Examiner* — Roy D Gibson
(74) *Attorney, Agent, or Firm* — Nutter McClennen & Fish LLP; Thomas J. Engellenner; Reza Mollaaghababa

(57) ABSTRACT

Methods and systems are disclosed for phototreatment in which replaceable containers comprising one or more adjuvant (consumable or re-useable) substances are employed. The adjuvant substance can be, for example, a topical substance or a coolant. Systems are disclosed for using a topical substance to detect contact of a phototreatment device with a tissue, detect speed of a phototreatment device over the tissue, detect regions of tissue that have been treated by a phototreatment device and/or to provide other benefits to the tissue such as improved skin tone and texture, tanning, etc. Safety systems are also disclosed that ensure that a proper consumable substance and/or container is connected to a phototreatment device and/or directed to a proper target. Additionally, cooling systems and methods that utilize phase change materials for extracting heat from a light generating device are disclosed.

15 Claims, 30 Drawing Sheets

U.S. PATENT DOCUMENTS

| | | | |
|---|---|---|---|
| 1,590,283 A | 6/1926 | Catlin | |
| 1,706,161 A | 3/1929 | Hollnagel | |
| 2,472,385 A | 6/1949 | Rollman | |
| 2,669,771 A | 2/1954 | Burge et al. | |
| 3,261,978 A | 7/1966 | Brenman | |
| 3,327,712 A | 6/1967 | Kaufman et al. | |
| 3,486,070 A | 12/1969 | Engel | |
| 3,527,932 A | 9/1970 | Thomas | |
| 3,538,919 A | 11/1970 | Meyer | |
| 3,597,652 A | 8/1971 | Gates, Jr. | |
| 3,622,743 A | 11/1971 | Muncheryan | |
| 3,653,778 A | 4/1972 | Freiling | |
| 3,667,454 A | 6/1972 | Prince | |
| 3,693,623 A | 9/1972 | Harte et al. | |
| 3,818,914 A | 6/1974 | Bender | |
| 3,834,391 A | 9/1974 | Block | |
| 3,846,811 A | 11/1974 | Nakamura et al. | |
| 3,857,015 A | 12/1974 | Clark et al. | |
| 3,890,537 A | 6/1975 | Park et al. | |
| 3,900,034 A | 8/1975 | Katz | |
| 3,909,649 A | 9/1975 | Arsena | |
| 3,939,560 A | 2/1976 | Lyall | |
| 3,977,083 A | 8/1976 | Leslie et al. | |
| 4,047,106 A | 9/1977 | Robinson | |
| 4,213,462 A | 7/1980 | Sato et al. | |
| 4,233,493 A | 11/1980 | Nath | |
| 4,269,067 A | 5/1981 | Tynan et al. | |
| 4,273,109 A | 6/1981 | Enderby | |
| 4,275,335 A | 6/1981 | Ishida | |
| 4,298,005 A | 11/1981 | Mutzhas | |
| 4,316,467 A | 2/1982 | Muckerheide | |
| 4,333,197 A | 6/1982 | Kuris | |
| 4,335,726 A | 6/1982 | Kolstedt | |
| 4,388,924 A | 6/1983 | Weissman et al. | |
| 4,409,479 A | 10/1983 | Sprague et al. | |
| 4,452,081 A | 6/1984 | Seppi | |
| 4,456,872 A | 6/1984 | Froeschle | |
| 4,461,294 A | 7/1984 | Baron | |
| 4,504,727 A | 3/1985 | Melcher et al. | |
| 4,512,197 A | 4/1985 | von Gutfeld et al. | |
| 4,524,289 A | 6/1985 | Hammond et al. | |
| 4,539,987 A | 9/1985 | Nath et al. | |
| 4,553,546 A | 11/1985 | Javelle | |
| 4,561,440 A | 12/1985 | Kubo et al. | |
| 4,566,271 A | 1/1986 | French et al. | |
| 4,591,762 A | 5/1986 | Nakamura | |
| 4,601,753 A | 7/1986 | Soileau et al. | |
| 4,608,978 A | 9/1986 | Rohr | |
| 4,608,979 A | 9/1986 | Breidenthal et al. | |
| 4,617,926 A | 10/1986 | Sutton | |
| 4,623,929 A | 11/1986 | Johnson et al. | |
| 4,653,495 A | 3/1987 | Nanaumi | |
| 4,677,347 A | 6/1987 | Nakamura et al. | |
| 4,686,986 A | 8/1987 | Fenyo et al. | |
| 4,695,697 A | 9/1987 | Kosa | |
| 4,710,677 A | 12/1987 | Halberstadt et al. | |
| 4,718,416 A | 1/1988 | Nanaumi | |
| 4,733,660 A | 3/1988 | Itzkan | |
| 4,736,745 A | 4/1988 | Gluckman | |
| 4,745,909 A | 5/1988 | Pelton et al. | |
| 4,747,660 A | 5/1988 | Nishioka et al. | |
| 4,749,913 A | 6/1988 | Stuermer et al. | |
| 4,775,361 A | 10/1988 | Jacques et al. | |
| 4,779,173 A | 10/1988 | Carr et al. | |
| 4,784,135 A | 11/1988 | Blum et al. | |
| 4,799,479 A | 1/1989 | Spears | |
| 4,819,669 A | 4/1989 | Politzer | |
| 4,826,431 A | 5/1989 | Fujimura et al. | |
| 4,832,024 A | 5/1989 | Boussignac et al. | |
| 4,840,174 A | 6/1989 | Gluckman | |
| 4,845,608 A | 7/1989 | Gdula | |
| 4,852,549 A | 8/1989 | Mori et al. | |
| 4,860,172 A | 8/1989 | Schlager et al. | |
| 4,860,744 A | 8/1989 | Johnson et al. | |
| 4,862,903 A | 9/1989 | Campbell | |
| 4,871,479 A | 10/1989 | Bachelard et al. | |
| 4,884,560 A | 12/1989 | Kuracina | |
| 4,898,438 A | 2/1990 | Mori | |
| 4,905,690 A | 3/1990 | Ohshiro et al. | |
| 4,914,298 A | 4/1990 | Quad et al. | |
| 4,917,084 A | 4/1990 | Sinofsky | |
| 4,926,227 A | 5/1990 | Jensen | |
| 4,928,038 A | 5/1990 | Nerone | |
| 4,930,504 A | 6/1990 | Diamantopoulos et al. | |
| 4,945,239 A | 7/1990 | Wist et al. | |
| 4,973,848 A * | 11/1990 | Kolobanov et al. | 250/458.1 |
| 4,976,308 A | 12/1990 | Faghri | |
| 4,992,256 A | 2/1991 | Skaggs et al. | |
| 5,000,752 A | 3/1991 | Hoskin et al. | |
| 5,030,090 A | 7/1991 | Maeda et al. | |
| 5,032,178 A | 7/1991 | Cornell | |
| 5,046,494 A | 9/1991 | Searfoss et al. | |
| 5,050,597 A | 9/1991 | Daikuzono | |
| 5,057,104 A | 10/1991 | Chess | |
| 5,059,192 A | 10/1991 | Zaias | |
| 5,065,515 A | 11/1991 | Iderosa | |
| 5,066,293 A | 11/1991 | Furumoto | |
| 5,071,417 A | 12/1991 | Sinofsky | |
| 5,108,388 A | 4/1992 | Trokel | |
| 5,127,395 A | 7/1992 | Bontemps | |
| 5,133,102 A | 7/1992 | Sakuma et al. | |
| 5,137,530 A | 8/1992 | Sand | |
| 5,140,984 A | 8/1992 | Dew et al. | |
| 5,159,601 A | 10/1992 | Huber | |
| 5,160,194 A | 11/1992 | Feldman | |
| 5,171,564 A | 12/1992 | Nathoo et al. | |
| 5,178,617 A | 1/1993 | Kuizenga et al. | |
| 5,182,557 A | 1/1993 | Lang | |
| 5,182,857 A | 2/1993 | Simon | |
| 5,192,278 A | 3/1993 | Hayes et al. | |
| 5,196,004 A | 3/1993 | Sinofsky | |
| 5,207,671 A | 5/1993 | Franken et al. | |
| 5,222,907 A | 6/1993 | Katabuchi et al. | |
| 5,225,926 A | 7/1993 | Cuomo et al. | |
| 5,226,907 A | 7/1993 | Tankovich | |
| 5,267,399 A | 12/1993 | Johnston | |
| 5,281,211 A | 1/1994 | Parel et al. | |
| 5,282,797 A | 2/1994 | Chess | |
| 5,287,372 A | 2/1994 | Ortiz | |
| 5,287,380 A | 2/1994 | Hsia | |
| 5,293,880 A | 3/1994 | Levitt | |
| 5,300,097 A | 4/1994 | Lerner et al. | |
| 5,303,585 A * | 4/1994 | Lichte | 73/290 V |
| 5,304,170 A | 4/1994 | Green | |
| 5,304,173 A | 4/1994 | Kittrell et al. | |
| 5,306,143 A | 4/1994 | Levy | |
| 5,306,274 A | 4/1994 | Long | |
| 5,320,618 A | 6/1994 | Gustafsson | |
| 5,334,191 A | 8/1994 | Poppas et al. | |
| 5,334,193 A | 8/1994 | Nardella | |
| 5,336,217 A | 8/1994 | Buys et al. | |
| 5,342,358 A | 8/1994 | Daikuzono et al. | |
| 5,344,418 A | 9/1994 | Ghaffari | |
| 5,344,434 A | 9/1994 | Talmore | |
| 5,348,551 A | 9/1994 | Spears et al. | |
| 5,350,376 A | 9/1994 | Brown | |
| 5,353,020 A | 10/1994 | Schurmann | |
| 5,353,790 A | 10/1994 | Jacques et al. | |
| 5,358,503 A | 10/1994 | Bertwell et al. | |
| 5,360,426 A | 11/1994 | Muller et al. | |
| 5,369,831 A | 12/1994 | Bock | |
| 5,380,317 A | 1/1995 | Everett et al. | |
| 5,386,427 A | 1/1995 | Zayhowski | |
| 5,403,306 A | 4/1995 | Edwards et al. | |
| 5,405,368 A | 4/1995 | Eckhouse | |
| 5,415,654 A | 5/1995 | Daikuzono | |
| 5,425,728 A | 6/1995 | Tankovich | |
| 5,425,754 A | 6/1995 | Braun et al. | |
| 5,445,608 A | 8/1995 | Chen et al. | |
| 5,445,611 A | 8/1995 | Eppstein et al. | |
| 5,454,807 A | 10/1995 | Lennox et al. | |
| 5,458,140 A | 10/1995 | Eppstein et al. | |
| 5,474,549 A | 12/1995 | Ortiz et al. | |
| 5,486,170 A | 1/1996 | Winston et al. | |
| 5,486,172 A | 1/1996 | Chess | |
| 5,501,680 A | 3/1996 | Kurtz et al. | |
| 5,502,582 A | 3/1996 | Larson et al. | |

| Patent No. | Date | Inventor |
|---|---|---|
| 5,505,726 A | 4/1996 | Meserol |
| 5,505,727 A | 4/1996 | Keller |
| 5,519,534 A | 5/1996 | Smith |
| 5,522,813 A | 6/1996 | Trelles |
| 5,527,368 A | 6/1996 | Supkis et al. |
| 5,531,739 A | 7/1996 | Trelles |
| 5,531,740 A | 7/1996 | Black |
| 5,536,168 A | 7/1996 | Bourke et al. |
| 5,549,660 A | 8/1996 | Mendes et al. |
| 5,558,667 A | 9/1996 | Yarborough et al. |
| 5,561,881 A | 10/1996 | Klinger et al. |
| 5,571,098 A | 11/1996 | Domankevitz et al. |
| 5,578,866 A | 11/1996 | DePoorter et al. |
| 5,595,568 A | 1/1997 | Anderson et al. |
| 5,611,793 A | 3/1997 | Wilson et al. |
| 5,616,140 A | 4/1997 | Prescott |
| 5,620,478 A | 4/1997 | Eckhouse |
| 5,626,631 A | 5/1997 | Eckhouse |
| 5,628,744 A | 5/1997 | Coleman et al. |
| 5,630,811 A | 5/1997 | Miller |
| 5,634,711 A | 6/1997 | Kennedy et al. |
| 5,649,972 A | 7/1997 | Hochstein |
| 5,652,481 A | 7/1997 | Johnson et al. |
| 5,653,706 A | 8/1997 | Zavislan et al. |
| 5,655,547 A | 8/1997 | Karni |
| 5,657,760 A | 8/1997 | Ying et al. |
| 5,658,148 A | 8/1997 | Neuberger et al. |
| 5,658,323 A | 8/1997 | Miller |
| 5,660,836 A | 8/1997 | Knowlton |
| 5,661,744 A | 8/1997 | Murakami et al. |
| 5,662,643 A | 9/1997 | Kung et al. |
| 5,662,644 A | 9/1997 | Swor |
| 5,673,451 A | 10/1997 | Moore et al. |
| 5,679,113 A | 10/1997 | Caisey et al. |
| 5,683,380 A | 11/1997 | Eckhouse et al. |
| 5,698,866 A | 12/1997 | Doiron et al. |
| 5,707,401 A | 1/1998 | Talmore |
| 5,707,403 A | 1/1998 | Grove et al. |
| 5,713,738 A | 2/1998 | Yarborough |
| 5,720,772 A | 2/1998 | Eckhouse |
| 5,722,397 A | 3/1998 | Eppstein |
| 5,725,522 A | 3/1998 | Sinofsky |
| 5,728,090 A | 3/1998 | Martin et al. |
| 5,735,844 A | 4/1998 | Anderson et al. |
| 5,735,884 A | 4/1998 | Thompson et al. |
| 5,738,678 A | 4/1998 | Patel |
| 5,742,392 A | 4/1998 | Anderson et al. |
| 5,743,901 A | 4/1998 | Grove et al. |
| 5,743,902 A | 4/1998 | Trost |
| 5,746,735 A | 5/1998 | Furumoto et al. |
| 5,755,751 A | 5/1998 | Eckhouse |
| 5,759,200 A | 6/1998 | Azar |
| 5,769,076 A | 6/1998 | Mackawa et al. |
| 5,782,249 A | 7/1998 | Weber et al. |
| 5,802,136 A | 9/1998 | Carol |
| 5,810,801 A | 9/1998 | Anderson et al. |
| 5,812,567 A | 9/1998 | Jeon et al. |
| 5,813,855 A | 9/1998 | Crisio, Jr. |
| 5,814,008 A | 9/1998 | Chen et al. |
| 5,814,040 A | 9/1998 | Nelson et al. |
| 5,814,041 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,827,264 A | 10/1998 | Hohla |
| 5,828,803 A | 10/1998 | Eckhouse |
| 5,830,208 A | 11/1998 | Muller |
| 5,835,648 A | 11/1998 | Narciso, Jr. et al. |
| 5,836,877 A | 11/1998 | Zavislan |
| 5,836,999 A | 11/1998 | Eckhouse et al. |
| 5,840,048 A | 11/1998 | Cheng |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,871,480 A | 2/1999 | Tankovich |
| 5,879,159 A | 3/1999 | Cipolla |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,893,828 A | 4/1999 | Uram |
| 5,895,350 A | 4/1999 | Hori |
| 5,906,609 A | 5/1999 | Assa et al. |
| 5,908,418 A | 6/1999 | Dority et al. |
| 5,913,883 A | 6/1999 | Alexander et al. |
| 5,916,211 A | 6/1999 | Quon et al. |
| 5,920,374 A | 7/1999 | Vaphiades et al. |
| 5,921,926 A | 7/1999 | Rolland et al. |
| 5,928,222 A | 7/1999 | Kleinerman |
| 5,944,687 A | 8/1999 | Benett et al. |
| 5,944,748 A | 8/1999 | Mager et al. |
| 5,948,011 A | 9/1999 | Knowlton |
| 5,949,222 A | 9/1999 | Buono |
| 5,954,710 A | 9/1999 | Paolini et al. |
| 5,955,490 A | 9/1999 | Kennedy et al. |
| 5,957,915 A | 9/1999 | Trost |
| 5,964,749 A | 10/1999 | Eckhouse et al. |
| 5,968,033 A | 10/1999 | Fuller |
| 5,968,034 A | 10/1999 | Fullmer et al. |
| 5,974,616 A | 11/1999 | Dreyfus |
| 5,977,723 A | 11/1999 | Yoon |
| 5,979,454 A | 11/1999 | Anvari et al. |
| 5,984,915 A | 11/1999 | Loeb et al. |
| 6,007,219 A | 12/1999 | O'Meara |
| 6,015,404 A | 1/2000 | Altshuler et al. |
| 6,022,316 A | 2/2000 | Epstein et al. |
| 6,026,828 A | 2/2000 | Altshuler |
| 6,027,495 A | 2/2000 | Miller |
| 6,029,303 A | 2/2000 | Dewan |
| 6,029,304 A | 2/2000 | Hulke et al. |
| 6,030,378 A | 2/2000 | Stewart |
| 6,030,399 A | 2/2000 | Ignotz et al. |
| 6,032,071 A | 2/2000 | Binder |
| RE36,634 E | 3/2000 | Ghaffari |
| 6,036,684 A | 3/2000 | Tankovich et al. |
| 6,044,514 A | 4/2000 | Kaneda et al. |
| 6,050,990 A | 4/2000 | Tankovich et al. |
| D424,197 S | 5/2000 | Sydlowski et al. |
| 6,056,548 A | 5/2000 | Neuberger et al. |
| 6,056,738 A | 5/2000 | Marchitto et al. |
| 6,058,937 A | 5/2000 | Doiron et al. |
| 6,059,820 A | 5/2000 | Baronov |
| 6,063,108 A | 5/2000 | Salansky et al. |
| 6,070,092 A | 5/2000 | Kazama et al. |
| 6,074,382 A | 6/2000 | Asah et al. |
| 6,080,146 A | 6/2000 | Altshuler et al. |
| 6,080,147 A | 6/2000 | Tobinick |
| 6,086,363 A | 7/2000 | Moran et al. |
| 6,086,580 A | 7/2000 | Mordon et al. |
| 6,094,767 A | 8/2000 | Iimura |
| 6,096,029 A | 8/2000 | O'Donnell, Jr. |
| 6,096,209 A | 8/2000 | O'Brien et al. |
| 6,099,521 A | 8/2000 | Shadduck |
| 6,104,959 A | 8/2000 | Spertell |
| 6,106,293 A | 8/2000 | Wiesel |
| 6,106,294 A | 8/2000 | Daniel |
| 6,110,195 A | 8/2000 | Xie et al. |
| 6,113,559 A | 9/2000 | Klopotek |
| 6,117,129 A | 9/2000 | Mukai |
| 6,120,497 A | 9/2000 | Anderson |
| 6,126,655 A | 10/2000 | Domankevitz et al. |
| 6,129,723 A | 10/2000 | Anderson et al. |
| 6,135,774 A | 10/2000 | Hack et al. |
| 6,142,650 A | 11/2000 | Brown et al. |
| 6,142,939 A | 11/2000 | Eppstein et al. |
| 6,149,644 A | 11/2000 | Xie |
| 6,149,895 A | 11/2000 | Kutsch |
| 6,159,236 A | 12/2000 | Biel |
| 6,162,055 A | 12/2000 | Montgomery et al. |
| 6,162,211 A | 12/2000 | Tankovich et al. |
| 6,162,212 A | 12/2000 | Kreindel et al. |
| 6,171,300 B1 | 1/2001 | Adams |
| 6,171,301 B1 | 1/2001 | Nelson |
| 6,171,302 B1 | 1/2001 | Talpalriu et al. |

| Patent | Date | Name |
|---|---|---|
| 6,171,332 B1 | 1/2001 | Whitehurst |
| 6,173,202 B1 | 1/2001 | Eppstein et al. |
| 6,174,325 B1 | 1/2001 | Eckhouse |
| 6,176,854 B1 | 1/2001 | Cone |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,187,029 B1 | 2/2001 | Shapiro et al. |
| 6,197,020 B1 | 3/2001 | O'Donnell |
| 6,200,134 B1 | 3/2001 | Kovac et al. |
| 6,200,309 B1 | 3/2001 | Rice et al. |
| 6,202,242 B1 | 3/2001 | Salmon et al. |
| 6,203,540 B1 | 3/2001 | Weber |
| 6,210,425 B1 | 4/2001 | Chen |
| 6,214,034 B1 | 4/2001 | Azar |
| 6,221,095 B1 | 4/2001 | Van Zuylen et al. |
| 6,228,075 B1 | 5/2001 | Furumoto |
| 6,229,831 B1 | 5/2001 | Nightingale et al. |
| 6,235,016 B1 | 5/2001 | Stewart |
| 6,236,891 B1 | 5/2001 | Ingle et al. |
| 6,239,442 B1 | 5/2001 | Iimura et al. |
| 6,240,306 B1 | 5/2001 | Rohrscheib et al. |
| 6,245,093 B1 | 6/2001 | Li et al. |
| 6,251,127 B1 | 6/2001 | Biel |
| 6,254,388 B1 | 7/2001 | Yarborough |
| 6,263,233 B1 | 7/2001 | Zavislan et al. |
| 6,264,649 B1 | 7/2001 | Whitcroft et al. |
| 6,267,779 B1 | 7/2001 | Gerdes |
| 6,267,780 B1 | 7/2001 | Streeter |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,283,956 B1 | 9/2001 | McDaniel |
| 6,290,496 B1 | 9/2001 | Azar et al. |
| 6,290,713 B1 | 9/2001 | Russell |
| 6,306,130 B1 | 10/2001 | Anderson et al. |
| 6,306,160 B1 | 10/2001 | Nidetzky |
| 6,315,772 B1 | 11/2001 | Marchitto et al. |
| 6,317,624 B1 | 11/2001 | Kollias et al. |
| 6,319,274 B1 | 11/2001 | Shadduck |
| 6,325,769 B1 | 12/2001 | Klopotek |
| 6,328,733 B1 | 12/2001 | Trost |
| 6,331,111 B1 | 12/2001 | Cao |
| 6,340,495 B1 | 1/2002 | Sumian et al. |
| 6,343,400 B1 | 2/2002 | Massholder et al. |
| 6,343,933 B1 | 2/2002 | Montgomery et al. |
| 6,350,261 B1 | 2/2002 | Domankevitz et al. |
| 6,350,276 B1 | 2/2002 | Knowlton |
| 6,354,370 B1 | 3/2002 | Miller et al. |
| 6,355,054 B1 | 3/2002 | Neuberger et al. |
| 6,358,242 B1 | 3/2002 | Cecchetti |
| 6,358,272 B1 | 3/2002 | Wilden |
| 6,383,176 B1 | 5/2002 | Connors et al. |
| 6,383,177 B1 | 5/2002 | Balle-Petersen et al. |
| 6,387,089 B1 | 5/2002 | Kreindel et al. |
| 6,387,353 B1 | 5/2002 | Jensen et al. |
| 6,395,016 B1 | 5/2002 | Oron et al. |
| 6,402,739 B1 | 6/2002 | Neev |
| 6,406,474 B1 | 6/2002 | Neuberger et al. |
| 6,413,267 B1 | 7/2002 | Dumoulin-White et al. |
| 6,416,319 B1 | 7/2002 | Cipolla |
| 6,419,389 B1 | 7/2002 | Fuchs et al. |
| 6,424,852 B1 | 7/2002 | Zavislan |
| 6,425,912 B1 | 7/2002 | Knowlton |
| 6,435,873 B1 | 8/2002 | Burgio |
| 6,436,094 B1 | 8/2002 | Reuter |
| 6,439,888 B1 | 8/2002 | Boutoussov et al. |
| 6,440,155 B1 | 8/2002 | Matsumae et al. |
| 6,443,978 B1 | 9/2002 | Zharov |
| 6,451,007 B1 | 9/2002 | Koop et al. |
| 6,461,296 B1 | 10/2002 | Desai |
| 6,471,712 B2 | 10/2002 | Burres |
| 6,471,716 B1 | 10/2002 | Pecukonis |
| 6,475,211 B2 | 11/2002 | Chess et al. |
| 6,484,052 B1 | 11/2002 | Visuri et al. |
| 6,485,413 B1 | 11/2002 | Boppart et al. |
| 6,494,900 B1 | 12/2002 | Salansky et al. |
| 6,497,702 B1 | 12/2002 | Bernaz |
| 6,503,486 B2 | 1/2003 | Xu et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,525,819 B1 | 2/2003 | Delawter et al. |
| 6,527,764 B1 | 3/2003 | Neuberger et al. |
| 6,530,915 B1 | 3/2003 | Eppstein et al. |
| 6,537,270 B1 | 3/2003 | Elbrecht et al. |
| 6,547,780 B1 | 4/2003 | Sinofsky |
| 6,551,346 B2 * | 4/2003 | Crossley .................. 607/88 |
| 6,554,439 B1 | 4/2003 | Teicher et al. |
| 6,556,596 B1 | 4/2003 | Kim et al. |
| 6,558,372 B1 | 5/2003 | Altshuler |
| 6,561,808 B2 | 5/2003 | Neuberger et al. |
| 6,569,155 B1 | 5/2003 | Connors et al. |
| 6,570,893 B1 | 5/2003 | Libatique et al. |
| 6,572,634 B2 | 6/2003 | Koo |
| 6,572,637 B1 | 6/2003 | Yamazaki et al. |
| 6,595,934 B1 | 7/2003 | Hissong et al. |
| 6,600,951 B1 | 7/2003 | Anderson |
| 6,602,245 B1 | 8/2003 | Thiberg |
| 6,605,080 B1 | 8/2003 | Altshuler et al. |
| 6,605,083 B1 | 8/2003 | Clement et al. |
| 6,606,755 B1 | 8/2003 | Robinson et al. |
| 6,616,447 B1 | 9/2003 | Rizoiu et al. |
| 6,616,451 B1 | 9/2003 | Rizolu et al. |
| 6,618,531 B1 | 9/2003 | Goto et al. |
| 6,623,272 B2 | 9/2003 | Clemans |
| 6,623,513 B2 | 9/2003 | Biel |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,578 B2 | 11/2003 | Mukai |
| 6,641,600 B1 | 11/2003 | Kohler |
| 6,648,904 B2 | 11/2003 | Altshuler et al. |
| 6,653,618 B2 | 11/2003 | Zenzie |
| 6,659,999 B1 | 12/2003 | Anderson et al. |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,675,425 B1 | 1/2004 | Iimura et al. |
| 6,676,654 B1 | 1/2004 | Balle-Petersen et al. |
| 6,679,837 B2 | 1/2004 | Daikuzono |
| 6,685,639 B1 | 2/2004 | Wang et al. |
| 6,685,699 B1 | 2/2004 | Eppstein et al. |
| 6,689,124 B1 | 2/2004 | Thiberg |
| 6,699,040 B1 | 3/2004 | Hahn et al. |
| 6,706,035 B2 | 3/2004 | Cense et al. |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,743,222 B2 | 6/2004 | Durkin et al. |
| 6,746,444 B2 | 6/2004 | Key |
| 6,749,623 B1 | 6/2004 | Hsi et al. |
| 6,770,069 B1 | 8/2004 | Hobart et al. |
| 6,790,205 B1 | 9/2004 | Yamazaki et al. |
| 6,801,595 B2 | 10/2004 | Grodzins et al. |
| 6,808,331 B2 | 10/2004 | Hall et al. |
| 6,808,532 B2 | 10/2004 | Anderson et al. |
| RE38,670 E | 12/2004 | Asah et al. |
| 6,858,009 B2 | 2/2005 | Kawata et al. |
| 6,860,879 B2 | 3/2005 | Irion et al. |
| 6,862,771 B1 | 3/2005 | Muller |
| 6,863,781 B2 | 3/2005 | Nocera et al. |
| 6,878,144 B2 | 4/2005 | Altshuler et al. |
| 6,881,212 B1 | 4/2005 | Clement et al. |
| 6,887,260 B1 | 5/2005 | McDaniel |
| 6,888,319 B2 | 5/2005 | Inochkin et al. |
| 6,893,259 B1 | 5/2005 | Reizenson |
| 6,902,397 B2 | 6/2005 | Farrell et al. |
| 6,902,563 B2 | 6/2005 | Wilkens et al. |
| 6,936,046 B2 | 8/2005 | Hissong et al. |
| 6,942,658 B1 | 9/2005 | Rizoiu et al. |
| 6,953,341 B2 | 10/2005 | Black |
| 6,974,451 B2 | 12/2005 | Altshuler et al. |

| | | | | | | |
|---|---|---|---|---|---|---|
| 6,976,985 B2 | 12/2005 | Altshuler et al. | 2003/0018373 A1 | 1/2003 | Eckhardt et al. | |
| 6,989,023 B2 | 1/2006 | Black | 2003/0023235 A1 | 1/2003 | Cense et al. | |
| 6,991,644 B2 | 1/2006 | Spooner et al. | 2003/0023283 A1 | 1/2003 | McDaniel | |
| 6,997,923 B2 | 2/2006 | Anderson et al. | 2003/0023284 A1 | 1/2003 | Gartstein et al. | |
| 7,001,413 B2 | 2/2006 | Butler | 2003/0028227 A1* | 2/2003 | Neuberger et al. | 607/88 |
| 7,006,223 B2 | 2/2006 | Mullani | 2003/0032900 A1 | 2/2003 | Ella | |
| 7,029,469 B2 | 4/2006 | Vasily | 2003/0032950 A1 | 2/2003 | Altshuler et al. | |
| 7,033,349 B2 | 4/2006 | Key | 2003/0036680 A1 | 2/2003 | Black | |
| 7,041,100 B2 | 5/2006 | Kreindel | 2003/0040739 A1 | 2/2003 | Koop | |
| 7,044,959 B2 | 5/2006 | Anderson et al. | 2003/0055414 A1 | 3/2003 | Altshuler et al. | |
| 7,060,061 B2 | 6/2006 | Altshuler et al. | 2003/0057875 A1 | 3/2003 | Inochkin et al. | |
| 7,066,733 B2 | 6/2006 | Logan et al. | 2003/0059738 A1 | 3/2003 | Neuberger | |
| 7,077,840 B2 | 7/2006 | Altshuler et al. | 2003/0065314 A1 | 4/2003 | Altshuler et al. | |
| 7,081,128 B2 | 7/2006 | Hart et al. | 2003/0083649 A1 | 5/2003 | Margaron et al. | |
| 7,097,639 B1 | 8/2006 | Almeida | 2003/0084534 A1 | 5/2003 | Kaizuka | |
| 7,097,656 B1 | 8/2006 | Akopov et al. | 2003/0097122 A1 | 5/2003 | Ganz et al. | |
| 7,144,247 B2 | 12/2006 | Black | 2003/0100936 A1 | 5/2003 | Altshuler et al. | |
| 7,144,248 B2 | 12/2006 | Irwin | 2003/0104340 A1 | 6/2003 | Clemans | |
| 7,145,105 B2 | 12/2006 | Gaulard | 2003/0109787 A1 | 6/2003 | Black | |
| 7,145,108 B2 | 12/2006 | Kanel et al. | 2003/0109860 A1 | 6/2003 | Black | |
| 7,160,289 B2 | 1/2007 | Cohen | 2003/0113684 A1 | 6/2003 | Scott | |
| 7,198,634 B2 | 4/2007 | Harth et al. | 2003/0129154 A1 | 7/2003 | McDaniel | |
| 7,204,832 B2 | 4/2007 | Altshuler et al. | 2003/0130709 A1 | 7/2003 | D.C. et al. | |
| 7,220,254 B2 | 5/2007 | Altshuler et al. | 2003/0152528 A1 | 8/2003 | Singh et al. | |
| 7,223,270 B2 | 5/2007 | Altshuler et al. | 2003/0163884 A1 | 9/2003 | Weihrauch | |
| 7,223,281 B2 | 5/2007 | Altshuler et al. | 2003/0167080 A1 | 9/2003 | Hart et al. | |
| 7,255,691 B2 | 8/2007 | Tolkoff et al. | 2003/0169433 A1 | 9/2003 | Koele et al. | |
| 7,274,155 B2 | 9/2007 | Inochkin et al. | 2003/0181896 A1 | 9/2003 | Zvuloni et al. | |
| 7,291,140 B2 | 11/2007 | MacFarland et al. | 2003/0187486 A1 | 10/2003 | Savage et al. | |
| 7,309,335 B2 | 12/2007 | Altshuler et al. | 2003/0195494 A1 | 10/2003 | Altshuler et al. | |
| 7,311,722 B2 | 12/2007 | Larsen | 2003/0199859 A1 | 10/2003 | Altshuler et al. | |
| 7,322,972 B2 | 1/2008 | Viator et al. | 2003/0216795 A1 | 11/2003 | Harth et al. | |
| 7,329,273 B2 | 2/2008 | Altshuler et al. | 2003/0232303 A1 | 12/2003 | Black | |
| 7,329,274 B2 | 2/2008 | Altshuler et al. | 2004/0006332 A1 | 1/2004 | Black | |
| 7,331,964 B2 | 2/2008 | Maricle et al. | 2004/0010298 A1 | 1/2004 | Altshuler et al. | |
| 7,333,698 B2 | 2/2008 | Israel | 2004/0015156 A1 | 1/2004 | Vasily | |
| 7,351,252 B2 | 4/2008 | Altshuler et al. | 2004/0015158 A1 | 1/2004 | Chen et al. | |
| 7,422,598 B2 | 9/2008 | Altshuler et al. | 2004/0019990 A1 | 2/2004 | Farrell et al. | |
| 7,431,419 B2 | 10/2008 | Turner et al. | 2004/0024388 A1 | 2/2004 | Altshuler | |
| 7,540,869 B2 | 6/2009 | Altshuler et al. | 2004/0030326 A1 | 2/2004 | Altshuler et al. | |
| 7,624,640 B2 | 12/2009 | Maris et al. | 2004/0034319 A1 | 2/2004 | Anderson et al. | |
| 7,647,092 B2 | 1/2010 | Motz et al. | 2004/0034341 A1 | 2/2004 | Altshuler et al. | |
| 2001/0007068 A1 | 7/2001 | Ota et al. | 2004/0073079 A1 | 4/2004 | Altshuler et al. | |
| 2001/0008973 A1 | 7/2001 | Van Zuylen et al. | 2004/0082940 A1 | 4/2004 | Black et al. | |
| 2001/0023363 A1 | 9/2001 | Harth et al. | 2004/0085026 A1 | 5/2004 | Inochkin et al. | |
| 2001/0024777 A1 | 9/2001 | Azar et al. | 2004/0093042 A1 | 5/2004 | Altshuler et al. | |
| 2001/0041886 A1 | 11/2001 | Durkin et al. | 2004/0093043 A1 | 5/2004 | Edel et al. | |
| 2001/0046652 A1 | 11/2001 | Ostler et al. | 2004/0111132 A1 | 6/2004 | Shenderova et al. | |
| 2001/0048077 A1 | 12/2001 | Afanassieva | 2004/0116984 A1 | 6/2004 | Spooner et al. | |
| 2002/0004066 A1 | 1/2002 | Stanley et al. | 2004/0133251 A1 | 7/2004 | Altshuler et al. | |
| 2002/0005475 A1 | 1/2002 | Zenzie | 2004/0143920 A1 | 7/2004 | Nanda | |
| 2002/0013572 A1 | 1/2002 | Berlin | 2004/0147984 A1 | 7/2004 | Altshuler et al. | |
| 2002/0016587 A1* | 2/2002 | Furumoto ............ 606/7 | 2004/0156626 A1 | 8/2004 | Thoms | |
| 2002/0018754 A1 | 2/2002 | Sagel et al. | 2004/0161213 A1 | 8/2004 | Lee | |
| 2002/0019624 A1 | 2/2002 | Clement et al. | 2004/0162549 A1 | 8/2004 | Altshuler et al. | |
| 2002/0026225 A1 | 2/2002 | Segal | 2004/0162596 A1 | 8/2004 | Altshuler et al. | |
| 2002/0029071 A1 | 3/2002 | Whitehurst | 2004/0176754 A1 | 9/2004 | Island et al. | |
| 2002/0049483 A1 | 4/2002 | Knowlton | 2004/0191729 A1 | 9/2004 | Altshuler et al. | |
| 2002/0058890 A1 | 5/2002 | Visuri et al. | 2004/0193234 A1 | 9/2004 | Butler | |
| 2002/0071287 A1 | 6/2002 | Haase | 2004/0193235 A1 | 9/2004 | Altshuler et al. | |
| 2002/0071827 A1 | 6/2002 | Petersen et al. | 2004/0193236 A1 | 9/2004 | Altshuler et al. | |
| 2002/0072676 A1 | 6/2002 | Afanassieva | 2004/0199227 A1 | 10/2004 | Altshuler et al. | |
| 2002/0081555 A1 | 6/2002 | Wiesel | 2004/0204745 A1 | 10/2004 | Altshuler et al. | |
| 2002/0091377 A1 | 7/2002 | Anderson | 2004/0210276 A1 | 10/2004 | Altshuler et al. | |
| 2002/0108193 A1 | 8/2002 | Gruber | 2004/0214132 A1 | 10/2004 | Altshuler | |
| 2002/0111610 A1 | 8/2002 | Nordquist | 2004/0225339 A1 | 11/2004 | Yaroslavsky et al. | |
| 2002/0120256 A1 | 8/2002 | Furuno et al. | 2004/0230258 A1 | 11/2004 | Altshuler et al. | |
| 2002/0123745 A1 | 9/2002 | Svaasand et al. | 2004/0230260 A1 | 11/2004 | MacFarland et al. | |
| 2002/0127224 A1 | 9/2002 | Chen | 2004/0234460 A1 | 11/2004 | Tarver et al. | |
| 2002/0128635 A1 | 9/2002 | Altshuler et al. | 2005/0038418 A1 | 2/2005 | Altshuler et al. | |
| 2002/0128695 A1 | 9/2002 | Harth et al. | 2005/0049467 A1 | 3/2005 | Stamatas et al. | |
| 2002/0161357 A1 | 10/2002 | Anderson | 2005/0049582 A1 | 3/2005 | DeBenedictis et al. | |
| 2002/0161418 A1 | 10/2002 | Wilkens et al. | 2005/0049658 A1 | 3/2005 | Connors et al. | |
| 2002/0173780 A1 | 11/2002 | Altshuler et al. | 2005/0063931 A1 | 3/2005 | Paus et al. | |
| 2002/0182563 A1 | 12/2002 | Boutoussov et al. | 2005/0065531 A1 | 3/2005 | Cohen | |
| 2002/0183808 A1 | 12/2002 | Biel | 2005/0085875 A1 | 4/2005 | Van Zuylen | |
| 2003/0004499 A1 | 1/2003 | McDaniel | 2005/0107849 A1 | 5/2005 | Altshuler et al. | |
| 2003/0009158 A1 | 1/2003 | Perricone | 2005/0168158 A1 | 8/2005 | Inochkin et al. | |
| 2003/0009205 A1 | 1/2003 | Biel | 2005/0171517 A1 | 8/2005 | Altshuler et al. | |

| | | | | | | |
|---|---|---|---|---|---|---|
| 2005/0171581 A1 | 8/2005 | Connors et al. | | EP | 0563953 | 10/1993 |
| 2005/0177026 A1 | 8/2005 | Hoeg et al. | | EP | 0565331 | 10/1993 |
| 2005/0182389 A1 | 8/2005 | LaPorte et al. | | EP | 0593375 | 4/1994 |
| 2005/0197681 A1 | 9/2005 | Barolet et al. | | EP | 0598984 | 6/1994 |
| 2005/0215988 A1 | 9/2005 | Altshuler et al. | | EP | 0709941 | 5/1996 |
| 2005/0220726 A1 | 10/2005 | Pauly et al. | | EP | 0724894 | 8/1996 |
| 2006/0004306 A1 | 1/2006 | Altshuler et al. | | EP | 0726083 | 8/1996 |
| 2006/0004347 A1 | 1/2006 | Altshuler et al. | | EP | 0736308 | 10/1996 |
| 2006/0009750 A1 | 1/2006 | Altshuler et al. | | EP | 0743029 | 11/1996 |
| 2006/0020309 A1 | 1/2006 | Altshuler et al. | | EP | 0755698 | 1/1997 |
| 2006/0047281 A1 | 3/2006 | Kreindel | | EP | 0763371 | 3/1997 |
| 2006/0058712 A1 | 3/2006 | Altshuler et al. | | EP | 0765673 | 4/1997 |
| 2006/0079947 A1 | 4/2006 | Tankovich et al. | | EP | 0765674 | 4/1997 |
| 2006/0089687 A1 | 4/2006 | Spooner et al. | | EP | 0783904 | 7/1997 |
| 2006/0094988 A1 | 5/2006 | Tosaya et al. | | EP | 0884066 | 12/1998 |
| 2006/0122668 A1 | 6/2006 | Anderson et al. | | EP | 0885629 | 12/1998 |
| 2006/0149343 A1 | 7/2006 | Altshuler et al. | | EP | 0920840 A2 | 6/1999 |
| 2006/0161143 A1 | 7/2006 | Altshuler et al. | | EP | 1038505 | 9/2000 |
| 2006/0194164 A1 | 8/2006 | Altshuler et al. | | EP | 1075854 | 2/2001 |
| 2006/0206103 A1 | 9/2006 | Altshuler et al. | | EP | 1138349 | 10/2001 |
| 2006/0253176 A1 | 11/2006 | Caruso et al. | | EP | 1147785 | 10/2001 |
| 2006/0271028 A1 | 11/2006 | Altshuler et al. | | EP | 1219258 | 7/2002 |
| 2006/0287646 A1 | 12/2006 | Altshuler et al. | | EP | 1226787 | 7/2002 |
| 2007/0027440 A1 | 2/2007 | Altshuler et al. | | EP | 1250893 | 10/2002 |
| 2007/0038206 A1 | 2/2007 | Altshuler et al. | | EP | 1057454 | 11/2003 |
| 2007/0049910 A1 | 3/2007 | Altshuler et al. | | EP | 1 457 234 A2 | 9/2004 |
| 2007/0060819 A1 | 3/2007 | Altshuler et al. | | EP | 1495735 A1 | 1/2005 |
| 2007/0067006 A1 | 3/2007 | Altshuler et al. | | EP | 1512373 | 3/2005 |
| 2007/0073308 A1 | 3/2007 | Anderson et al. | | EP | 1535582 | 6/2005 |
| 2007/0078501 A1 | 4/2007 | Altshuler et al. | | EP | 1627662 A1 | 2/2006 |
| 2007/0159592 A1 | 7/2007 | Rylander et al. | | EP | 1839705 A1 | 10/2007 |
| 2007/0185552 A1 | 8/2007 | Masotti et al. | | EP | 1854505 A2 | 11/2007 |
| 2007/0194717 A1 | 8/2007 | Belikov et al. | | FR | 2199453 | 4/1974 |
| 2007/0198004 A1 | 8/2007 | Altshuler et al. | | FR | 2591902 | 6/1987 |
| 2007/0213696 A1 | 9/2007 | Altshuler et al. | | GB | 1546625 | 5/1979 |
| 2007/0213698 A1 | 9/2007 | Altshuler et al. | | GB | 2044908 | 10/1980 |
| 2007/0213792 A1 | 9/2007 | Yaroslavsky et al. | | GB | 2059053 | 4/1981 |
| 2007/0219604 A1 | 9/2007 | Yaroslavsky et al. | | GB | 2059054 | 4/1981 |
| 2007/0219605 A1 | 9/2007 | Yaroslavsky et al. | | GB | 2123287 | 2/1984 |
| 2007/0239142 A1 | 10/2007 | Altshuler et al. | | GB | 2239675 A | 7/1991 |
| 2007/0239143 A1 | 10/2007 | Altshuler et al. | | GB | 2270159 A | 3/1994 |
| 2007/0255355 A1 | 11/2007 | Altshuler et al. | | GB | 2356570 | 5/2001 |
| 2007/0288071 A1 | 12/2007 | Rogers | | GB | 2360461 A | 9/2001 |
| 2008/0009842 A1 | 1/2008 | Manstein et al. | | GB | 2360946 | 10/2001 |
| 2008/0058783 A1 | 3/2008 | Altshuler et al. | | GB | 2364376 | 1/2002 |
| 2008/0132886 A1 | 6/2008 | Cohen et al. | | GB | 2368020 | 4/2002 |
| 2008/0139901 A1 | 6/2008 | Altshuler et al. | | GB | 2390021 | 12/2003 |
| 2008/0140164 A1 | 6/2008 | Oberreiter et al. | | GB | 2397528 | 7/2004 |
| 2008/0172047 A1 | 7/2008 | Altshuler et al. | | JP | 1099574 A | 4/1989 |
| 2008/0183162 A1 | 7/2008 | Altshuler et al. | | JP | 2174804 | 7/1990 |
| 2008/0183250 A1 | 7/2008 | Tanojo et al. | | JP | 3066387 A | 3/1991 |
| 2008/0195183 A1 | 8/2008 | Botchkareva et al. | | JP | 199013014 A | 9/1991 |
| 2008/0214988 A1 | 9/2008 | Altshuler et al. | | JP | 6022871 | 2/1994 |
| 2008/0294150 A1 | 11/2008 | Altshuler et al. | | JP | 9084803 A | 3/1997 |
| 2008/0306471 A1 | 12/2008 | Altshuler et al. | | JP | 9141869 A | 6/1997 |
| 2009/0048557 A1 | 2/2009 | Yeshurun et al. | | JP | 10014661 | 1/1998 |
| 2009/0069741 A1 | 3/2009 | Altshuler et al. | | JP | 10165410 A | 6/1998 |
| | | | | JP | 11047146 A | 2/1999 |
| FOREIGN PATENT DOCUMENTS | | | | JP | 11081877 A | 3/1999 |
| AU | 1851583 | 3/1984 | | JP | 2000037400 A | 2/2000 |
| CN | 2053926 | 3/1990 | | JP | 2000300684 A | 10/2000 |
| CN | 1073607 | 6/1993 | | JP | 2001145520 | 5/2001 |
| CN | 1182572 A | 5/1998 | | JP | 2002506362 T | 2/2002 |
| CN | 1351483 A | 5/2002 | | JP | 2003192809 | 2/2005 |
| CN | 1535126 A | 10/2004 | | RU | 2082337/95105406 | 6/1997 |
| DE | 3304230 A1 | 8/1984 | | RU | 2089126/94012665 | 10/1997 |
| DE | 3719561 | 1/1988 | | RU | 2089127/94040344 | 10/1997 |
| DE | 3837248 | 5/1990 | | RU | 2096051/95012749 | 11/1997 |
| DE | 9102407 | 7/1991 | | RU | 2122848/4954402 | 10/1998 |
| DE | 19803460 | 8/1999 | | WO | WO 86/02783 | 5/1986 |
| DE | 19944401 A1 | 3/2001 | | WO | WO 88/04592 | 6/1988 |
| DE | 10140715 A1 | 3/2002 | | WO | WO 90/00420 | 11/1990 |
| DE | 10112289 A1 | 9/2002 | | WO | 91/02562 A1 | 3/1991 |
| DE | 10120787 | 1/2003 | | WO | WO 91/13652 | 9/1991 |
| EP | 0593 A1 | 2/1979 | | WO | WO 92/16338 | 1/1992 |
| EP | 0142671 | 5/1985 | | WO | WO 92/19165 | 11/1992 |
| EP | 0172490 A1 | 2/1986 | | WO | WO 93/05920 | 4/1993 |
| EP | 0320080 A1 | 6/1989 | | WO | 95/10243 A1 | 4/1995 |
| EP | 0324120 A1 | 7/1989 | | WO | WO 95/15725 | 6/1995 |

| | | |
|---|---|---|
| WO | WO 95/32441 | 11/1995 |
| WO | WO 96/23447 | 8/1996 |
| WO | WO 96/25979 | 8/1996 |
| WO | 96/28212 | 9/1996 |
| WO | WO 96/36396 | 11/1996 |
| WO | WO 96/41579 | 12/1996 |
| WO | 97/013552 | 4/1997 |
| WO | WO 97/13458 | 4/1997 |
| WO | 97/22384 A1 | 6/1997 |
| WO | 98/05286 A1 | 2/1998 |
| WO | 98/05380 | 2/1998 |
| WO | 98/06456 A1 | 2/1998 |
| WO | WO 98/04317 | 2/1998 |
| WO | WO 98/24507 | 6/1998 |
| WO | WO 98/51235 | 11/1998 |
| WO | WO 98/52481 | 11/1998 |
| WO | WO 98/58595 | 12/1998 |
| WO | 99/10046 A1 | 3/1999 |
| WO | WO 99/17666 | 4/1999 |
| WO | WO 99/17667 | 4/1999 |
| WO | WO 99/27997 | 6/1999 |
| WO | WO 99/29243 | 6/1999 |
| WO | 99/34867 A1 | 7/1999 |
| WO | WO 99/38569 | 8/1999 |
| WO | 99/43387 A1 | 9/1999 |
| WO | 99/44638 A1 | 9/1999 |
| WO | WO 99/46005 | 9/1999 |
| WO | WO 99/49937 | 10/1999 |
| WO | 99/62472 A1 | 12/1999 |
| WO | 99/66988 A1 | 12/1999 |
| WO | WO 00/02491 | 1/2000 |
| WO | WO 00/03257 | 1/2000 |
| WO | 0007514 A1 | 2/2000 |
| WO | 0030714 A1 | 2/2000 |
| WO | WO 00/32272 | 6/2000 |
| WO | 0041278 A1 | 7/2000 |
| WO | WO 00/40266 | 7/2000 |
| WO | WO 00/43070 | 7/2000 |
| WO | WO 00/44294 | 8/2000 |
| WO | 0054649 A2 | 9/2000 |
| WO | 0054685 | 9/2000 |
| WO | 0062700 A1 | 10/2000 |
| WO | 0066226 A1 | 11/2000 |
| WO | WO 00/64537 | 11/2000 |
| WO | WO 00/71045 | 11/2000 |
| WO | WO 00/74583 | 12/2000 |
| WO | WO 00/74781 | 12/2000 |
| WO | WO 00/78242 | 12/2000 |
| WO | WO 01/03257 | 1/2001 |
| WO | 0114012 A1 | 3/2001 |
| WO | WO 01/26573 | 4/2001 |
| WO | WO 01/34048 | 5/2001 |
| WO | WO 01/42671 | 6/2001 |
| WO | WO 01/54606 | 8/2001 |
| WO | WO 01/54770 | 8/2001 |
| WO | WO 01/78830 | 10/2001 |
| WO | 02/09813 A1 | 2/2002 |
| WO | 02/26147 A1 | 4/2002 |
| WO | WO 02/053050 | 7/2002 |
| WO | WO 02/069825 | 9/2002 |
| WO | 02078559 A1 | 10/2002 |
| WO | WO 02/094116 | 11/2002 |
| WO | 03005883 A2 | 1/2003 |
| WO | 03049633 A1 | 6/2003 |
| WO | 2004000150 A1 | 12/2003 |
| WO | 2004033040 A1 | 4/2004 |
| WO | 2004037068 A2 | 5/2004 |
| WO | 2004037287 A2 | 5/2004 |
| WO | 2004080279 A2 | 9/2004 |
| WO | WO 2004/073537 | 9/2004 |
| WO | WO 2004/084752 | 10/2004 |
| WO | WO 2004/086947 A2 | 10/2004 |
| WO | WO 2005/007003 A1 | 1/2005 |
| WO | 2005009266 A1 | 2/2005 |
| WO | 2005030317 A2 | 4/2005 |
| WO | 2005046793 A2 | 5/2005 |
| WO | 2005065288 A2 | 7/2005 |
| WO | 2005092438 A1 | 10/2005 |
| WO | 2005096981 A2 | 10/2005 |
| WO | 2005099369 A2 | 10/2005 |
| WO | 2005112815 A1 | 12/2005 |
| WO | 2006006123 A1 | 1/2006 |
| WO | WO 2006/036968 A2 | 4/2006 |
| WO | 2006066226 A1 | 6/2006 |
| WO | 2006089227 A2 | 8/2006 |
| WO | 2006101735 A1 | 9/2006 |
| WO | 2006116141 A1 | 11/2006 |
| WO | 2007035444 A2 | 3/2007 |
| WO | 2007122611 A2 | 11/2007 |
| WO | 2008070747 A2 | 6/2008 |

OTHER PUBLICATIONS

Communication pursuant to Article 94(3) EPC dated Nov. 2, 2009 for European patent application EP03711558.1.
PCT/US2006/035927 International Report on Patentability dated Oct. 8, 2007.
English Translation of Chinese Office Action (Chinese Application No. 200610093460.9) dated Aug. 22, 2008.
Sheehan-Dare, et al., "Lasers in Dermatology," British Journal of Dermatology, 129:1-8 (1993).
Shimizu et al., "Prospect of Relieving Pain Due to Tooth Movement During Orthodontic Treatment Utilizing a GA-AI As Diode Laser," SPIE vol. 1984, pp. 275-280.
Shumilovitch et al., "Influence of Low Intensity Laser Radiation Upon the Microflora of Carious Cavities and Root Canal," SPIE vol. 1984, pp. 215-220.
Sing, "Electroacupuncture and Laser Stimulation Treatment: Evaluation by Somatosensory Evoked Potential in Conscious Rabbits," Abstract Am-J-Chin-Med. 1997; 25(3-4): 263-71.
Sliney et al., "Safety with Lasers and Other Optical Sources: A Comprehensive Handbook," Plenum Press, pp. 477-480 (1980).
Sokolova et al., "Low-intense Laser Radiation in Complex Treatment of Inflammatory Diseases of Parodontium," SPIE vol. 1984, pp. 234-237.
Unger, "Laser Hair Transplantation III, Computer-assisted Laser Transplanting," Dermatol. Surg., 21:1047-1055 (1995).
Van Bruegel, "Power Density and Exposure Time of He-Ne Irradiation Are More Important Than Total Energy Dose in Photo-Biomodulation of Human Fibroblasts in Vitro," Lasers in Surgery and Medicine, vol. 12 pp. 528-537, 1992.
Walsh, "Laser "Curettage": a Critical Analysis," Periodontology 14:4-12, 1993.
Walsh, "The Current Status of Low Level Laser Therapy in Dentistry. Part 1. Soft Tissue Applications" paper prepared by LJ Walsh, Department of Dentistry University of Queensland, pp. 1-16. Publication date unknown.
Watanabe, S. et al., "The Effect of Pulse Duration on Selective Pigmented Cell Injury by Dye Lasers," The Journal of Investigative Dermatology, 88:523, 1987.
Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998.
Zonios et al., "Skin Melanin, Hemoglobin, and Light Scattering Properties can be Quantitatively Assessed in Vivo Using Diffuse Reflectance Spectroscopy," Journal of Investigative Dermatology,117:1452-1457 (Dec. 2001).
"BIOPTRON Light Therapy System," website print-out, accessed Jul. 13, 2006 (2 pages).
Altshuler et al., "Human Tooth as an Optical Device," SPIE vol. 1429 Holography and Interferometry and Optical Pattern Recognition in Biomedicine, pp. 95-104, 1991.
Altshuler et al., "Modern Optics and Dentistry," Laser in Dentistry, pp. 283-297, 1995.
Altshuler et al., "New Optical Effects in the Human Hard Tooth Tissues," Lasers and Medicine, Proc. SPIE vol. 1353, pp. 97-102, 1989.
Apfelberg et al. "Analysis of Complications of Argon Laser Treatment for Port Wine Hemangiomas with Reference to Striped Technique," Lasers in Surgery and Medicine, 2:357-371 (1983).

Apfelberg et al. "Dot or Pointillistic Method for Improvement in Results of Hypertrophic Scarring in the Argon Laser Treatment of Portwine Hemangiomas," Lasers in Surgery and Medicine, 6:552-558 (1987).

Blankenau et al., "In Vivo Caries-Like Lesion Prevention with Argon Laser: Pilot Study," Journal of Clinical Laser Medicine and Surgery, vol. 17, No. 6, pp. 241-243, 1999.

Chan, E.K., "Effects of Compression on Soft Tissue Optical Properties," IEEE Journal of Selected Topics in Quantum Electronics, vol. 2, No. 4, pp. 943-950 (Dec. 1996).

Dabrowska, "Intravital Treatment of the Pulp with Stimulation Laser Biostimulation," Abstract Rocz-Akad-Med-Bialymst. 1997; 42(1): 168-76.

Dixon et al. "Hypertrophic Scarring in Argon Laser Treatment of Port-Wine Stains," Plastic and Reconstructive Surgery, 73:771-777 (1984).

Forrest-Winchester et al., "The Effect of Infrared Laser Radiation on Dentinal Permeability in vitro," Department of Dentistry, University of Queensland Dental School, pp. 1-8, 1992.

Ginsbach et al. "New Aspects in the Management of Benign Cutameous Tumors," Laser 79 Opto-Electronics, Munich Conference Proceedings, 344-347 (1979).

Gottlieb, I., "Power Supplies, Switching Regulators, Inverters & Converters," 1976.

Greenwald et al. "Comparative Histological Studies of the Tunable Dye (at 577 nm) Laser and Argon Laser: The Specific Vascular Effects of the Dye Laser," The Journal of Investigative Dermatology, 77:305-310 (1981).

Grossman, et al., "780 nm Low Power Diode Laser Irradiation Stimulates Proliferation of Keratinocyte Cultures: Involvement of Reactive Oxygen Species," Lasers in Surgery and Medicine vol. 29, pp. 212-218, 1998.

Hicks et al., "After Low Fluence Argon Laser and Flouride Treatment," Compendium, vol. 18, No. 6, Jun. 1997.

Hicks et al., "Enamel Carries Initiation and Progression Following Low Fluence (energy) and Argon Laser and Fluoride Treatment," The Journal of Clinical Pediatric Dentistry, vol. 20, No. 1 pp. 9-13, 1995.

Hsu et al., "Combined Effects of Laser Irradiation/Solution Flouride Ion on Enamel Demineralization," Journal of Clinical Laser Medicine and Surgery, vol. 16, No. 2 pp. 93-105, 1998.

Hulsbergen Henning et al. "Clinical and Histological Evaluation of Portwine Stain Treatment with a Microsecond-Pulsed Dye-Laser at 577 NM," Lasers in Surgery and Medicine, 4:375-380 (1984).

Hulsbergen Henning et al., "Port Wine Stain Coagulation Experiments with a 540-nm Continuous Wave Dye-Laser," Lasers in Surgery and Medicine, 2:205-210 (1983).

Ivanov, A.P. et al., "Radiation Propagation in Tissues and Liquids with Close Particle Packing," Zhurnal Prikladnoi Spektroskopii, vol. 47, No. 4, pp. 662-668 (Oct. 1987).

Kalivradzhiyan et al., "The Usage of Low Intensity Laser Radiation for the Treatment of the Inflammatory processes of the Oral Cavity Mucosa after Applying Removable Plate Dentures," SPIE vol. 1984 pp. 225-230.

Karu, "Cell Attachment to Extracellular Matrics is Modulated by Pulsed Radiation at 820 nm and Chemicals that Modify the Activity of Enzymes in the Plasma Membrane," Laser in Surgery and Medicine, vol. 29, pp. 274-281, 2001.

Karu, "Photobiological Fundamentals of Low-Power Laser Therapy," 8th Congress of International Society for Laser Surgery and Medicine, Mar. 30, 1987.

Kazmina et al., "Laser Prophlaxis and Treatment of Primary caries," SPIE vol. 1984, pp. 231-233.

Kozlov et al., "Laser in Diagnostics and Treatment of Microcirculation Disorders Under Parodontitis," SPIE vol. 1984, pp. 253-264.

Levin, G. et al., "Designing with hyseretic current-mode control, " EDN Magazine, pp. 1-8, Apr. 11, 1996.

Levin, G. et al., "Designing with hyseretic current-mode control, " EDN Magazine, pp. 1-8, Apr. 28, 1994.

Maegawa, et al., "Effects of Near-Infrared Low-Level Laser Irradiation on Microcirculation," Lasers in Surgery and Medicine, vol. 27, pp. 427-437, 2000.

Mamedova et al., "Microbiological Estimate of Parodontis Laser Therapy Efficiency," SPIE vol. 1984, pp. 247-249.

Mang, "Effect of Soft Laser Treatment on Wound Healing in the Hamster Oral Mucosa," American Society for Laser Medicine and Surgery Abstracts, Chapters 25, pp. 5-8.

Marinelli et al., "Diode laser illuminated automotive lamp systems," SPIE Proceedings vol. 3285:170-177 (1998).

McDaniel, et al., "Hexascan: A New Robotized Scanning Laser Handpiece," Cutis, 45:300-305 (1990).

Nemeth, et al., "Copper vapor laser treatment of pigmented lesions," Lasers Surg. Med. Supp. 2:51 (1990).

Ohbayashi, "Stimulatory Effect of Laser Irradiation on Calcified Nodule Formation in Human Dental Pulp Fibroblasts," Abstract J-Endod. Jan. 1999; 25(1): 30-3.

Oleinik, et al., "Automatized Securing Definition for Laser Therapy Indications in Case of Non-complicated Caries," SPIE, vol. 1984, pp. 238-244.

Orchardson, "Effect of Pulsed Nd:YAG Laser Radiation on Action Potential Conduction in Nerve Fibres Inside Teeth in vitro," Abstract J-Dent. Jul.-Aug. 1998; 26(5-6): 421-6.

Osigo et al, "Phase Transitions of Rat Stratum Corneum Lipids By an Electron Paramagnetic Resonance Study and Relationship of Phase States to Drug Penetration," Biochimica et Biophysica Acta 1301:97-104 (1996).

Ozawa et al., "Stimulatory Effects of Low-Power Laser Irradiation on Bone Formation in vitro," SPIE vol. 1984, pp. 281-288.

Petrischev et al. "Clinical and Experimental Low-Intense Laser Therapy in Dentistry," SPIE, vol. 1984, pp. 212-214.

Petrischev et al., "Report on Low Intensity Laser Radiation Usage in Dentistry," SPIE vol. 1984, pp. 202-211.

Powell, "Laser Dental Decay Prevention: does it have a future?" SPIE vol. 3192, 1997.

Remillard et al., "Diode laser illuminated automotive brake lamp using a linear fanout diffractive optical element," Proc. of the Diffractive Optics and Micro-Optics Conference, OSA Technical Digest Series vol. 10, 192-194 (1998).

Remillard et al., "Diode Laser Illuminators for Night-Vision Applications," SPIE Proceedings vol. 4285:14-22 (2001).

Rohrer, "Evaluating the Safety and Efficacy Of A Novel Light Based Hair Removal System," Lasers. Surg. Med. Supp.13:97 (2001).

Rotteleur, et al., "Robotized scanning laser handpiece for the treatment of port wine stains and other angiodysplasias," Lasers Surg. Med., 8:283-287 (1988).

Rubach et al., "Histological and Clinical Evaluation of Facial Resurfacing Using a Carbon Dioxide Laser With the Computer Pattern Generator," Arch Otolaryngol Head Neck Surg., 123:929-934 (1997).

Rylander, C.G. et al., "Mechanical Tissue Optical Clearing Devices: Enhancement of Light Penetration in Ex Vivo Porcine Skin and Adipose Tissue," Lasers in Surgery and Medicine, vol. 40, pp. 688-694 (2008).

Sandford et al., "Thermal Effects During Desensitisation of Teeth with Gallium-Aluminum-Arsenide Lasers," University of Queensland Dental School, Periodontology 15: 25-30 (1994).

Schindl, "Does Low Intensity Laser Irradiation Really Cause Cell Damage?" Laser in Surgery and Medicine vol. 22, pp. 105, 2001.

G.B. Altshuler et al., "Acoustic response of hard dental tissues to pulsed laser action," SPIE, vol. 2080, Dental Application of Lasers, pp. 97-103, 1993.

G.B. Altshuler et al., "Extended theory of selective photothermolysis," Lasers in Surgery and Medicine, vol. 29, pp. 416-432, 2001.

R.L. Amy & R. Storb, "Selective mitochondrial damage by a ruby laser microbeam: An electron microscopic study," Science, vol, 15, pp. 756-758, Nov. 1965.

R.R. Anderson et al., "The optics of human skin," Journal of Investigative Dermatology, vol. 77, No. 1, pp. 13-19, 1981.

R.R. Anderson & J.A. Parrish, "Selective photothermolysis: Precise microsurgery by selective absorption of pulsed radiation," Science, vol. 220, pp. 524-527, Apr. 1983.

A.V. Belikov et al., "Identification of enamel and dentine under tooth laser treatment," SPIE vol. 2623, Progress in Biomedical Optics Europe Series, Proceedings of Medical Applications of Lasers III, pp. 109-116, Sep. 1995.

P. Bjerring et al., "Selective Non-Ablative Wrinkle Reduction by Laser," J Cutan Laser Ther, vol. 2, pp. 9-15, 2000.

Doukas et al., "Transdermal Drug Delivery With a Pressure Wave," Advanced Drug Delivery Reviews 56 (2004), pp. 559-579.

J.S. Dover et al., "Pigmented guinea pig skin irradiated with Q-switched ruby laser pulses," Arch Dermatol, vol. 125, pp. 43-49, Jan. 1989.

L.H. Finkelstein & L.M. Blatstein, "Epilation of hair-bearing urethral grafts using the neodymium:yag surgical laser," Journal of Urology, vol. 146, pp. 840-842, Sep. 1991.

E.J. Fiskerstrand et al., "Hair Removal With Long Pulsed Diode Lasers: A Comparison Between Two Systems With Different Pulse Structures," Lasers in Surgery and Medicine, vol. 32, pp. 399-404, 2003.

L. Goldman, Biomedical Aspects of the Laser, Springer-Verlag New York Inc., publishers, Chapts. 1, 2, & 23, 1967.

L. Goldman, "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.

L. Goldman, "Effects of new laser systems on the skin," Arch Dermatol., vol. 108, pp. 385-390, Sep. 1973.

L. Goldman, "Laser surgery for skin cancer," New York State Journal of Medicine, pp. 1897-1900, Oct. 1977.

L. Goldman, "Surgery by laser for malignant melanoma," J. Dermatol. Surg. Oncol., vol, 5, No. 2, pp. 141-144, Feb. 1979.

L. Goldman, "The skin," Arch Environ Health, vol. 18, pp. 434-436, Mar. 1969.

L. Goldman & D.F. Richfield, "The effect of repeated exposures to laser beams," Acta derm.-vernereol., vol. 44, pp. 264-268, 1964.

L. Goldman & R.J. Rockwell, "Laser action at the cellular level," JAMA, vol. 198, No. 6, pp. 641-644, Nov. 1966.

L. Goldman et al., The biomedical aspects of lasers, JAMA, vol. 188, No. 3, pp. 302-306, Apr. 1964.

L. Goldman et al., "Effect of the laser beam on the skin, Preliminary report" Journal of Investigative Dermatology, vol. 40, pp. 121-122, 1963.

L. Goldman et al., "Effect of the laser beam on the skin, III. Exposure of cytological preparations," Journal of Investigative Dermatology, vol. 42, pp. 247-251, 1964.

L. Goldman et al., "Impact of the laser on nevi and melanomas," Archives of Dermatology, vol. 90, pp. 71-75, Jul. 1964.

L. Goldman et al., "Laser treatment of tattoos, A preliminary survey of three year's clinical experience," JAMA, vol. 201, No. 11, pp. 841-844, Sep. 1967.

L. Goldman et al., "Long-term laser exposure of a senile freckle," ArchEnviron Health, vol. 22, pp. 401-403, Mar. 1971.

L. Goldman et al., "Pathology, Pathology of the effect of the laser beam on the skin," Nature, vol. 197, No. 4870, pp. 912-914, Mar. 1963.

L. Goldman et al., "Preliminary investigation of fat embolization from pulsed ruby laser impacts of bone," Nature, vol. 221, pp. 361-363, Jan. 1969.

L. Goldman et al., "Radiation from a Q-switched ruby laser, Effect of repeated impacts of power output of 10 megawatts on a tattoo of man," Journal of Investigative Dermatology, vol. 44, pp. 69-71, 1965.

L. Goldman et al., "Replica microscopy and scanning electron microscopy of laser impacts on the skin," Journal of Investigative Dermatology, vol. 52, No. 1, pp. 18-24, 1969.

M.C. Grossman et al., "Damage to hair follicles by normal-mode ruby laser pulses," Journal of he American Academy of Dermatology, vol. 35, No. 6, pp. 889-894, Dec. 1996.

M.C. Grossman et al., "Laser Targeted at Hair Follicles," Lasers Med Surg., Suppl. 7:221,1995.

E. Klein et al., "Biological effects of laser radiation 1.,"Northeast Electroncis Research and Engineering Meeting, NEREM Record, IEEE catalogue No. F-60, pp. 108-109, 1965.

J.G. Kuhns et al., "Laser injury in skin," Laboratory Investigation, vol. 17, No. 1, pp. 1-13, Jul. 1967.

J.G. Kuhns et al., "Biological effects of laser radiation II Effects of laser irradiation on the skin," NEREM Record, pp. 152-153, 1965.

D. Manstein et al., "Selective Photothermolysis of Lipid-Rich Tissue," American Society for Laser Medicine and Surgery Abstracts, No. 17, American Society for Laser Medicine and Surgery Twenty-First Annual Meeting, Apr. 20-22, 2001, p. 6.

R.J. Margolis et al., "Visible action spectrum for melanin-specific selective photothermolysis," Lasers in Surgery and Medicine, vol. 9, pp. 389-397, 1989.

Ohshiro et al., "The Ruby and Argon Lasers in the Treatment of the Naevi," Annals Academy of Medicine, Apr. 1983, vol. 12, No. 2, pp. 388-395.

J.A. Parrish, "Selective thermal effects with pulsed irradiation from lasers: From organ to organelle," Journal of Investigative Dermatology, vol. 80, No. 6 Supplement, pp. 75s-80s, 1983.

L. Polla et al., "Melanosomes are a primary target of Q-switched ruby laser irradiation in guinea pig skin," Journal of Investigative Dermatology, vol. 89, No. 3, pp. 281-286, Sep. 1987.

Riggle et al., "Laser Effects On Normal and Tumor Tissue," Laser Applications in Medicine and Biology, vol. 1, M.L. Wolbarsht, editor, Plenum Press, publishers, Chapter 3, pp. 35-65, 1971.

T. Shimbashi & T. Kojima, "Ruby laser treatment of pigmented skin lesions," Aesth. Plast. Surg., vol. 19, pp. 225-229, 1995.

Stratton, K., et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.

Sumian, C.C. et al., "A Preliminary Clinical And Histopathological Study Of Laser Skin Resurfacing Using A Frequency-Doubled Nd:YAG Laser After Application of Chromofilm®," Journal of Cutaneous Laser Therapy, vol. 1, pp. 159-166, 1999.

Sumian, C.C. et al., "Laser Skin-Resurfacing Using A Frequency Doubled Nd:YAG Laser After Topical Application Of An Exogenous Chromophore," Lasers in Surgery and Medicine, vol. 25, pp. 43-50, 1999.

C.R. Taylor et al., "Treatment of tattoos by Q-switched ruby laser," Arch. Dermatol. vol. 126, pp. 893-899, Jul. 1990.

V.V. Tuchin, "Laser light scattering in biomedical diagnostics and therapy," Journal of Laser Applications, vol. 5, No. 2-3, pp. 43-60, 1993.

S. Watanabe et al, "Comparative studies of femtosecond to microsecond laser pulses on selective pigmented cell injury in skin," Photochemistry and Photobiology, vol. 53, No. 6, pp. 757-762, 1991.

A.J. Welch et al., "Evaluation of cooling techniques for the protection of the epidermis during HD-yag laser irradiation of the skin," Neodymium-Yag Laser in Medicine and Surgery, Elsevier Science Publishing Co., publisher, pp. 195-204, 1983.

R.B. Yules et al., "The effect of Q-switched ruby laser radiation on dermal tattoo pigment in man," Arch Surg, vol. 95, pp. 179-180, Aug. 1967.

E. Zeitler and M. L. Wolbarsht, "Laser Characteristics that Might be Useful in Biology," Laser Applications in Medicine and Biology, vol. I, M.L. Wolbarsht, editor, Plenum Press, publishers, Chapter 1, pp. 1-18, 1971.

Abstracts Nos. 17-19, Lasers in Surgery and Medicine, ASLMS, Supplement 13, 2001.

Abstracts Nos. 219-223, ASLMS.

US 6,230,044, 05/2001, Afanassieva et al. (withdrawn)

* cited by examiner

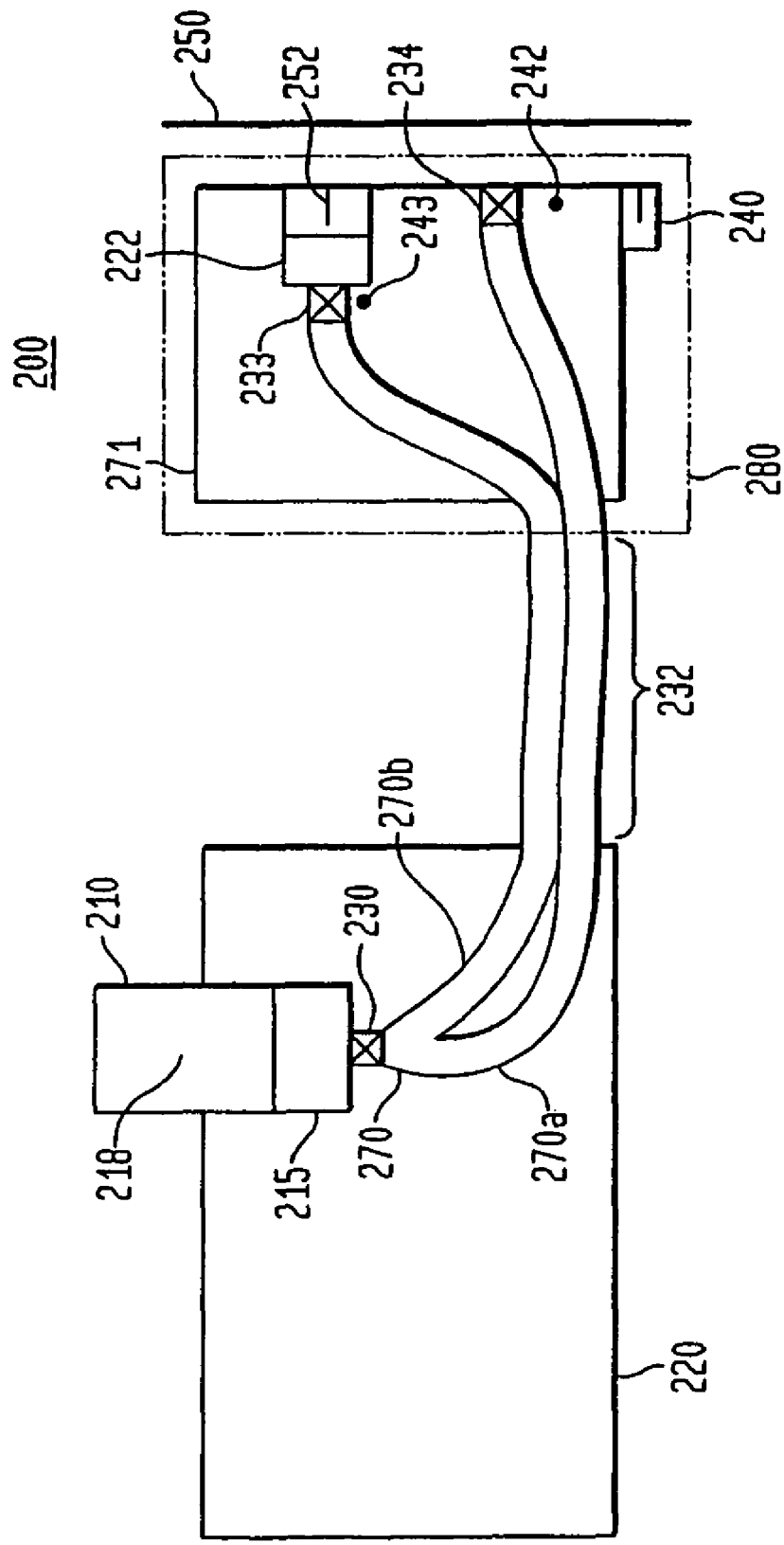

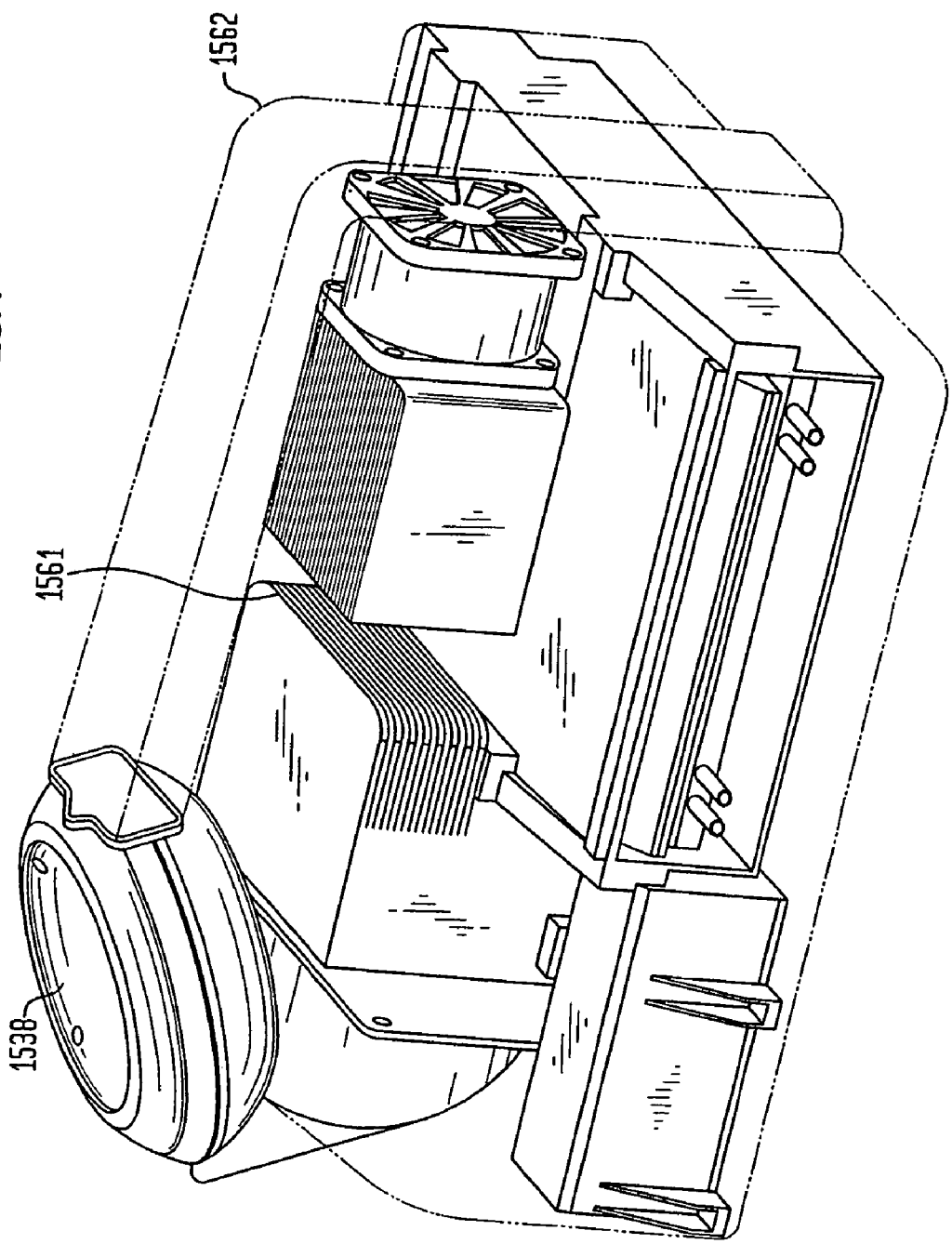

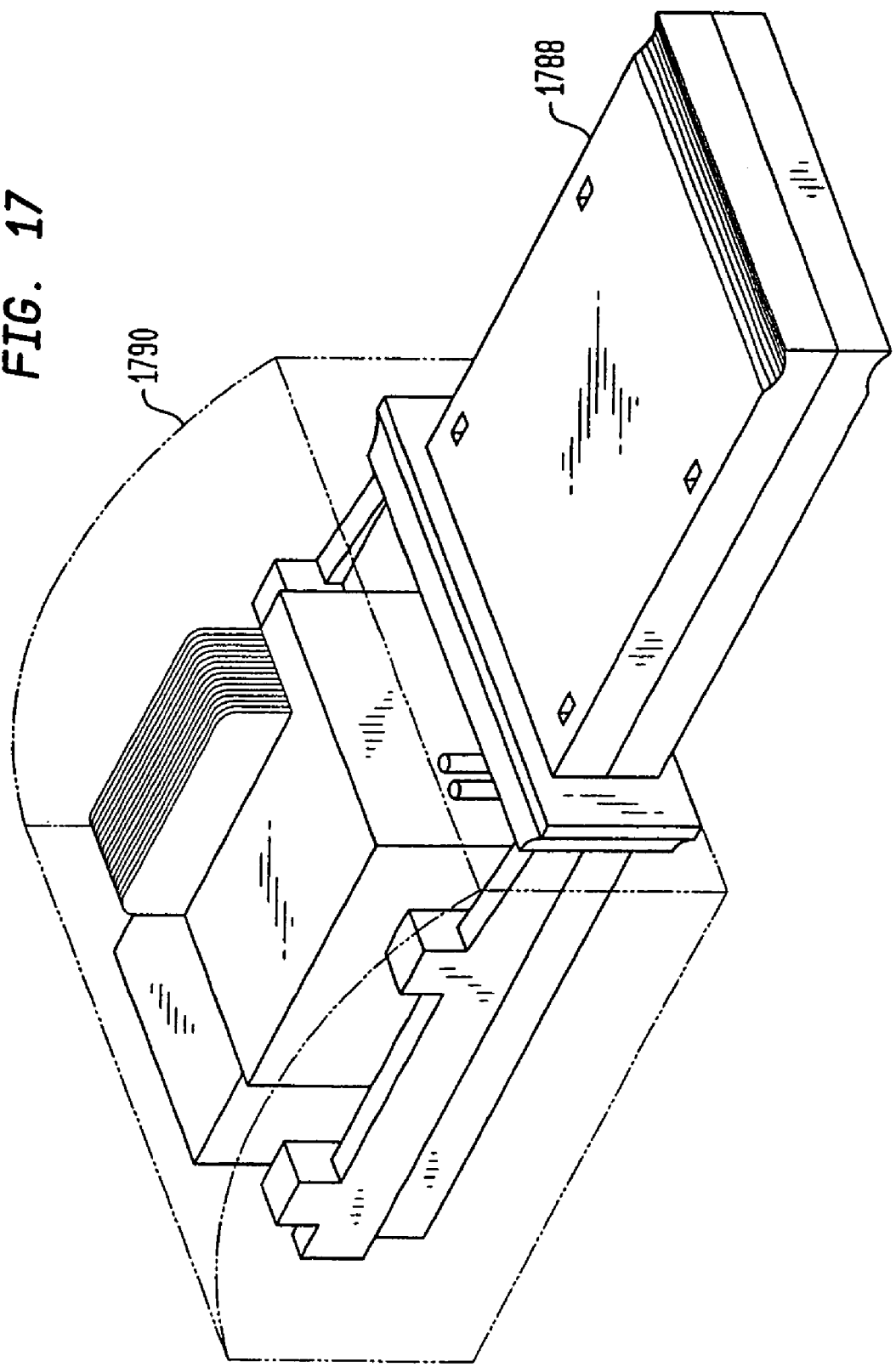

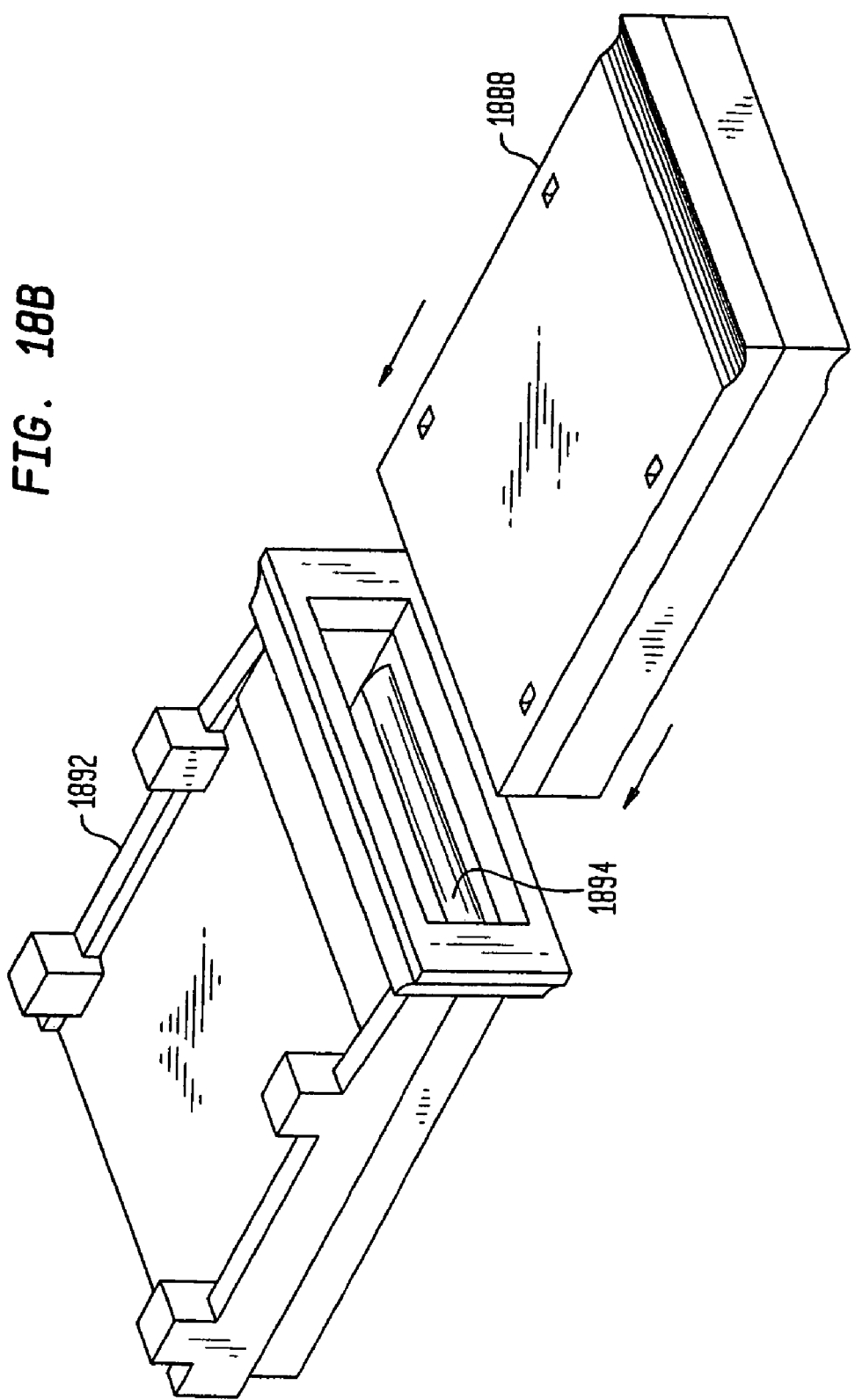

PHOTOTREATMENT DEVICE FOR USE WITH COOLANTS AND TOPICAL SUBSTANCES

PRIORITY

This application is a continuation of U.S. application Ser. No. 11/598,412 filed Nov. 13, 2006, which is a continuation of U.S. application Ser. No. 10/693,682 filed Oct. 23, 2003, now U.S. Pat. No. 7,135,033, which is a continuation-in-part of U.S. application Ser. No. 10/154,756 filed May 23, 2002, now U.S. Pat. No. 7,204,832 and claims priority to U.S. provisional application No. 60/420,645 filed Oct. 23, 2002 and U.S. provisional application No. 60/498,258 filed Aug. 25, 2003.

BACKGROUND OF THE INVENTION

The present invention is directed generally to systems and methods for phototreatment in which adjuvant substances are used for cooling or topical applications.

There exists a variety of conditions that are treatable using phototreatments of tissue (e.g., phototherapeutic and photocosmetic treatments). Such phototreatments include light-based hair removal, treatment of various skin lesions (including pigmented and vascular lesions as well as acne), tattoo removal, facial skin improvement, fat and cellulite treatment, scar removal, and skin rejuvenation (including wrinkle reduction and improvement of tone and texture), odor redaction, acne treatment to name a few.

Typically, light from a phototreatment device treats a tissue using a photothermal mechanism (i.e., a target structure or a tissue proximate the target structure is heated to effect the treatment) and/or a photodynamic therapy mechanism (i.e., the light causes a photochemical reaction). A variety of different light sources can be incorporated into a handpiece of a photocosmetic device for generating radiation suitable for a desired treatment of a patient's skin. These light sources, which can be either coherent or non-coherent, can emit light at a single wavelength, multiple wavelengths or in one or more wavelength bands. Some examples of such light sources include, without limitation, diode lasers, LEDs, arc lamps, flash lamps, tungsten lamps, and any other suitable light emitting devices.

Such light sources typically convert a portion of an applied electrical energy into optical energy while the rest of the electrical energy is converted into waste heat. For example, in a photocosmetic device that utilizes a diode laser bar as the source of optical radiation, up to about 40-60% of the electrical energy may be converted into waste heat. For LEDs, this loss can be as high as 70-99%. Other light sources may exhibit different efficiencies for generating optical energy. However, in general, a substantial amount of waste heat is generated that needs to be removed in order to ensure proper operation of the light source and to prevent shortening its lifetime. In addition, heat removal is important to ensure that the temperature of the components of the handpiece that are in contact with a patient's skin remain in a suitable range that is not damaging to the skin.

Adjuvant substances include consumable and reusable coolants to be applied to one or more target components of a phototreatment device. For example, because of the use of high-power radiation to perform phototreatments, one or more electronic or optical components may generate significant amounts of heat. Such components include, for example, laser diodes, LED or high-power electrical components. Coolants for removing heat from such components have been used to reduce the expense of maintaining phototreatment devices by increasing their operational lifetimes and/or to improve their safety.

Phototreatment devices are also often used with other consumable materials including, for example, topical substances. Conventional topical substances include any suitable topical liquid or emollient, such as a lotion, gel, water, alcohol, or oil. Such topical substances may be used, for example, to improve the safety of a device, efficacy of a treatment, cosmetic qualities of a treated tissue, and/or comfort of a patient.

While consumable substances, such as those discussed above may provide benefits, the use of consumable materials may lead to difficulty and expense in packaging, handling, and manufacturing of phototreatment devices employing such materials. Hence, there is a need for methods and systems that allow efficient and cost effective delivery of adjuvant substances during phototreatment.

SUMMARY OF THE INVENTION

Methods and systems are disclosed for phototreatment in which replaceable containers comprising one or more adjuvant (consumable or re-useable) substances are employed. The adjuvant substance can be, for example, a topical substance or a coolant. Systems are disclosed for using a topical substance to detect contact of a phototreatment device with a tissue, detect speed of a phototreatment device over the tissue, detect regions of tissue that have been treated by a phototreatment device and/or to provide other benefits to the tissue such as improved skin tone and texture, tanning, etc. Safety systems are also disclosed that ensure that a proper consumable substance and/or container is connected to a phototreatment device and/or directed to a proper target. Additionally, cooling systems and methods that utilize phase change materials for extracting heat from a light generating device are disclosed.

In one aspect, the invention provides a container having a container housing defining at least one compartment therein, a substance contained in the compartment, and an indicator coupled to the compartment for monitoring substance release during phototreatment. The housing and compartment are capable of being coupled to a phototreatment device to provide a flow path for substance release during phototreatment. The compartment can be fluidly coupled to at least one element selected from the group consisting of a head of a phototreatment device, a heat dissipating element in the phototreatment device, a target area, and a tissue region to be treated. The indicator can indicate an aspect of the container (i.e., amount of substance contained therein, temperature, etc.) or the substance (i.e., temperature, activity, etc.). The indicator can be selected, for example, from the group including mechanical indicia, optical indicia, magnetic indicia, electronic indicia, and piezoelectronic indicia. The substance can be a consumable substance and can contain a marker.

In another aspect of the invention, a subassembly is disclosed for use with a phototreatment device to treat a tissue. The subassembly has a container capable of storing a substance and coupling to the phototreatment device. The subassembly can further include a detector coupled to the container and configured and arranged to monitor a substance parameter. The container can have an outlet to allow release and/or replenishing of the substance, which can be a consumable substance, such as a coolant and a topical substance. Non-limiting examples of a topical substance include lotions, water, alcohols, oils, gels, powders, aerosols, granular particles, creams, gels, waxes, and films. The consumable substance can include a super-cooled liquid, a pressurized gas, or a phase change material. For example, the consumable substance can be a phase-changing material exhibiting a phase transition from a liquid to a gaseous state or exhibiting a phase transition from a solid to a liquid state. Suitable phase change materials include, but are not limited to, liquid carbon tetrafluoride, liquid $CO_2$, ice, frozen lotions, frozen wax, frozen creams and frozen gels. The container can be fluidly coupled to the device, a tissue region, a target area, a head of the device, or a heat dissipating element located within the device, e.g., located in a handle of the device. The container can also contain a reusable substance, such as a phase-change material. The detector can be a mechanical detector, an optical detector, a magnetic detector, an electronic detector, and a piezoelectronic detector. The subassembly can be replaced by the user.

In another aspect, the invention discloses a container having a housing defining at least one compartment therein, a substance contained in the compartment. The housing and the compartment are capable of coupling to a phototreatment device to permit heat transfer between the substance and the device. The container further includes an indicator coupled to the compartment. The compartment is capable of being fluidly coupled to at least one of a head of a phototreatment device, a heat dissipating element, or a tissue to be treated. The substance contained in the container can be a re-useable substance, such as a phase change material, or a consumable substance, such as a coolant or topical substance. The substance can further contain a marker. Non-limiting examples of markers include absorptive markers, photoactive markers, optical markers, fluorescent markers, electric markers, and magnetic markers. The marker can indicate an aspect of the substance. The marker can be selected from the group consisting of dyes, metals, ions, colored particles, photosensitive dyes, photosensitive materials, carbon particles, conductive skin lotions, electrolyte sprays, conductive electrode gels, and oxides.

At least one compartment of the container can have a first compartment and a second compartment, the first compartment is adapted to couple to a tissue, and the second compartment is adapted to couple to a heat dissipating element in the phototreatment device. The first compartment can contain a topical substance, such as lotion, cream, wax, film, water, alcohol, oil, gel, powder, aerosol, and granular particles. The topical substance can achieve at least one of moisturizing skin, UV protection, tanning skin, improving skin texture, improving skin tone, reduction and/or prevention of cellulite, reduction and/or prevention of acne, wrinkle reduction and/or prevention of wrinkles, reduction of scars, reduction and/or prevention of vascular lesions, reduction in pore size, oil reduction in sebum secretion, skin elasticity improvement, reduction in sweat secretion, reduction and/or improvement of odor, body hair reduction or removal, and stimulation of hair growth. The second compartment of the container can contain a coolant. Non-limiting examples of a coolant include liquid tetrafluorethane (R-134a), liquid $CO_2$, ice, frozen lotion, frozen gel, cristallohydrates (45% $CaCl*6H_2O$:55% $CaBr*6H_2O$ ore $KF*4H_2O$), organic materials as $HO(C_2H_4O)_8C_2H_4OH$ (PE Glycol), Caprilic acid, Hexadecane, and Paraffin 5913. A single consumable substance can function as a topical substance and a coolant, and can be directed to both tissue and a heat dissipating element. In some embodiments of the present invention, a container for a topical substance and/or coolant comprises a first compartment fluidly connectable to a tissue, and a second compartment fluidly connectable to a heat dissipating element of the phototreatment device.

In another aspect, the invention provides a method of operating a phototreatment device comprising the steps of coupling a container of an adjuvant substance, having an indicator associated therewith to permit monitoring of the substance, to a phototreatment device, determining a value of the indicator, and enabling operation of the phototreatment device if the value is acceptable. The step of enabling operation can include, for example, activating a radiation source. The indicator can be, without limitation, an optical indicator, mechanical indicator, electronic indicator, and magnetic indicator.

In yet another aspect, the invention provides a system, having a radiation source, a detector, and a processor, for measuring a speed of motion of a phototreatment device over a tissue region, where the phototreatment device has an electromagnetic source to effect a phototreatment and the tissue region has a substance applied thereto. An applicator coupled to the phototreatment device can be used for depositing the substance, which can contain a marker, onto the tissue prior to irradiation of the tissue region by the radiation source. The substance contains a marker. Non-limiting examples of markers include fluorescent markers, absorptive markers, electrical markers, optical markers, and magnetic markers. The radiation source can be positioned on the phototreatment device to irradiate the tissue region and the applied substance. The detector is associated with the phototherapeutic device configured and arranged to monitor the substance. The processor calculates a speed of motion of the phototreatment device based on signals from the detector. The radiation source can be further coupled to the phototreatment device for irradiating a plurality of tissue locations and the substance applied thereto as the device moves over the tissue region. The detector can be further coupled to the phototreatment device at a selected distance from the radiation source and arranged to monitor a response of the substance at an irradiated location subsequent to the irradiation. The processor can be further coupled to the detector for comparing the monitored response with a pre-selected value to determine a continues or discrete speed of motion of the phototreatment device.

The system can contain a comparator for comparing the calculated speed of motion with a defined maximum speed value in order to determine when the calculated speed has exceeded a threshold established by the defined maximum speed. A maximum speed can be in the 10-500 mm/sec range. A comparator can also be used for comparing the calculated speed of motion with a defined minimum speed value in order to determine when the calculated speed has fallen below a threshold established by the defined minimum speed. A minimum speed can be in the 5-100 mm/sec range. The system also contains a shut-off switch responsive to a control signal to terminate phototreatment when the speed has fallen below the threshold, thereby preventing potential injury to the user, or when the speed is above the threshold, thereby preventing ineffective treatment. For example, the control signal can enable the processor to control the electromagnetic source based on the speed of the phototherapeutic device. The shut-off switch can include a shutter that blocks the radiation and/or an alarm to alert the user.

In another aspect, the invention provides a method of operating a phototreatment device that includes the steps of applying a topical substance to a tissue, detecting a parameter associated with the topical substance, and enabling operation of the phototreatment device based on a detected value of the substance parameter.

In yet another aspect, a phototreatment device for use with a marker is disclosed. The device includes a radiation source to effect a phototreatment on a region of tissue, and a detector assembly to detect the marker and to selectively activate the radiation source based on marker detection. The detector can be, for example, an optical detector, a heat detector, an electronic detector, a mechanical detector, or a magnetic detector. The detector assembly can be configured and arranged to detect a reflected portion of light from an object, and to determine if the object is a tissue. The device can also have an applicator configured and arranged to deposit the marker in at least a portion of the region.

In other aspects, applicants have realized that a phase transition of a phase change material can be employed to extract heat from an element that is heated or generates heat ("heated element") and is incorporated in a handpiece of a photocosmetic device. The heated element may be any element that generates heat. Such heat generating elements can include, for example, a light source, a portion of a patient's skin or electronics incorporated in the device. Further, a heated element can include any element that receives heat (i.e., it is heated) from a heat generating source. Such elements can include, for example, a heat sink, a heat exchanger, a heat spreader, a heat pipe, a heat transfer element, a circulating gas or liquid, or components (including optical components) that are in thermal contact with a treatment site. The term "phase change material," as used herein, refers to any substance or compound that exhibits at least two phases between which a transition can be caused by either removing heat from or depositing heat into the substance or compound. The transition between these phases typically occurs at a well defined temperature herein referred to as a phase transition temperature, which can depend on ambient pressure. The heat deposited or removed from such a phase transition material at the phase transition temperature is herein referred to as the latent heat associated with the phase transition. For example, a phase change material can be initially in a solid phase, and can transition into a liquid phase by absorbing an amount of heat, which is herein referred to as the latent heat of melting.

In many embodiments of the invention described below, ice is employed as a phase change material for removing waste heat generated by a light source incorporated in a handpiece of a photocosmetic device. Applicants have discovered that ice is a particularly suitable material for use in various embodiments of the invention because it exhibits a fairly high latent heat of melting, namely, 330 J/g at atmospheric pressure, thus providing an efficient mechanism for heat removal. Further, melting of ice generates water, which is a biologically compatible substance, is environmentally safe, and can be mixed with skin beneficial compounds. Although ice is described below as one preferred substance whose phase transition can be utilized in the practice of the invention for heat removal, it should be understood that other suitable phase transition materials can also be employed. Further, rather than utilizing the latent heat of melting, the latent heat of sublimation of a phase transition material, such as dry ice, can be utilized in the practice of the invention to remove heat from a heated element.

A variety of different embodiments that utilize such phase change for cooling a photocosmetic device are described below. In principle, the phase change medium, e.g., ice, can be provided in the handpiece itself to be in thermal contact with a heat generator (e.g., a light source), typically via a heat transfer element (e.g., a copper block), or in thermal contact with any other heated element. Alternatively, the phase transition medium can be provided in a base of the photocosmetic device to extract heat from a cooling fluid that circulates between the base and the handpiece to cool a heat generator (e.g., light source) or any other heated element (e.g., the optical system that delivers light onto a patient's skin). Those having ordinary skill in the art will appreciate that other alternative approaches are also possible. For example, phase transition media can be provided both in the handpiece for direct cooling of the heated elements in the handpiece (e.g., the skin and/or light source) and in the base for functioning as a heat exchanger for electronics.

In one aspect, the invention provides a closed-loop (renewable) cooling system for extracting heat from a heated element of a photocosmetic device in which a phase change medium, e.g., ice, subsequent to its phase transition as a result of heat absorption is regenerated in a state suitable for heat extraction, and is reused. The regeneration of the phase change medium can be performed, for example, by a refrigeration unit incorporated in, or externally coupled to the photocosmetic device.

In another aspect, a phase change medium is utilized to extract heat from a circulating fluid that in turn removes heat from a heated element of a photocosmetic device. The phase change medium can be located remotely relative to the heated element.

The term "thermal contact" is generally known in the art. To the extent that a definition may be needed, this term as used herein in intended to encompass any coupling between at least two elements that allows transfer of heat between them. Such a thermal coupling can be obtained by a direct physical contact between the elements, or via an intermediate heat conducting element, or heat pipe or loop with circulating gas or liquid. A heat exchanger is a device for transferring heat from one medium to another, for example, from water to air, from ice to water, or from water to water. The better the thermal contact between the media, the more effective the heat exchanger. Alternatively, or in addition, radiative heat transfer can be established between two elements without direct physical contact or the use of an intermediate heat conducting element. Hence, in general, two elements are in thermal contact so long as heat can be transferred between them.

In further aspects, the invention provides a cartridge that can contain a selected quantity of a phase change material. The cartridge can couple to a heated element incorporated in a photocosmetic device, so as to bring the phase change material into thermal contact therewith. The heat transfer from the heated element to the phase change medium causes a phase transition of the phase change medium, for example, from a solid state to a liquid state, thereby removing heat from the heated element. The cartridge can further include a flow path for directing fluid, which can be generated following the phase change, away from the heated element.

In another aspect, the invention provides a cartridge for storing a phase change medium, which can be removably and replaceably placed within the flow path of a cooling fluid utilized for extracting heat from a heated element of a photocosmetic device. A phase transition of the phase change medium removes heat carried by the cooling fluid, thereby lowering its temperature.

In another aspect, the invention provides mechanisms for applying pressure to a phase change medium to facilitate maintaining good or optimum thermal contact between the phase change medium and a heated element incorporated in a photocosmetic device. The applied pressure ensures that the phase change medium remains in good or optimum thermal contact with the heated element as the heat from the heated element causes a phase transition of the phase change medium at its interface with the heated element.

In yet another aspect, the invention provides a cooling device, in which a phase change medium can be stored, that can couple to an optically transmissive element of a handpiece of a photocosmetic device so as to provide thermal contact between the phase change medium and the optical element. A phase transition of the phase change medium extracts heat from the optical element, thereby maintaining its temperature in an acceptable range.

Although several of the following embodiments are directed to cooling a light source incorporated in a photocosmetic device, those having ordinary skill in the art will appreciate that the teachings of the invention can be employed to cool light sources incorporated in other devices, such as, military, consumer or commercial lighting, industrial, medical and a variety of consumer devices. In general, the teachings of the invention are applicable to cooling any light source having a finite operational life time.

BRIEF DESCRIPTION OF THE DRAWINGS

Illustrative, non-limiting embodiments of the present invention will be described by way of example with reference to the accompanying drawings.

FIG. 2 is a schematic view of a phototreatment device including a consumable substance application system according to aspects of the present invention;

FIG. 15A is a schematic perspective view of a cooling mechanism, coupling the cartridge of FIG. 11 onto a base unit of a photocosmetic device and utilizing a TE cooler provided in the base unit for freezing water contained in the cartridge into ice;

FIG. 17 is a schematic perspective view of a cassette containing ice coupled to a base unit of a photocosmetic device for removing heat from a heat exchanger provided in the base unit;

FIG. 18B schematically illustrates the cassette and the receiving module of FIG. 18A in a disengaged state;

DETAILED DESCRIPTION

Figure 1A:
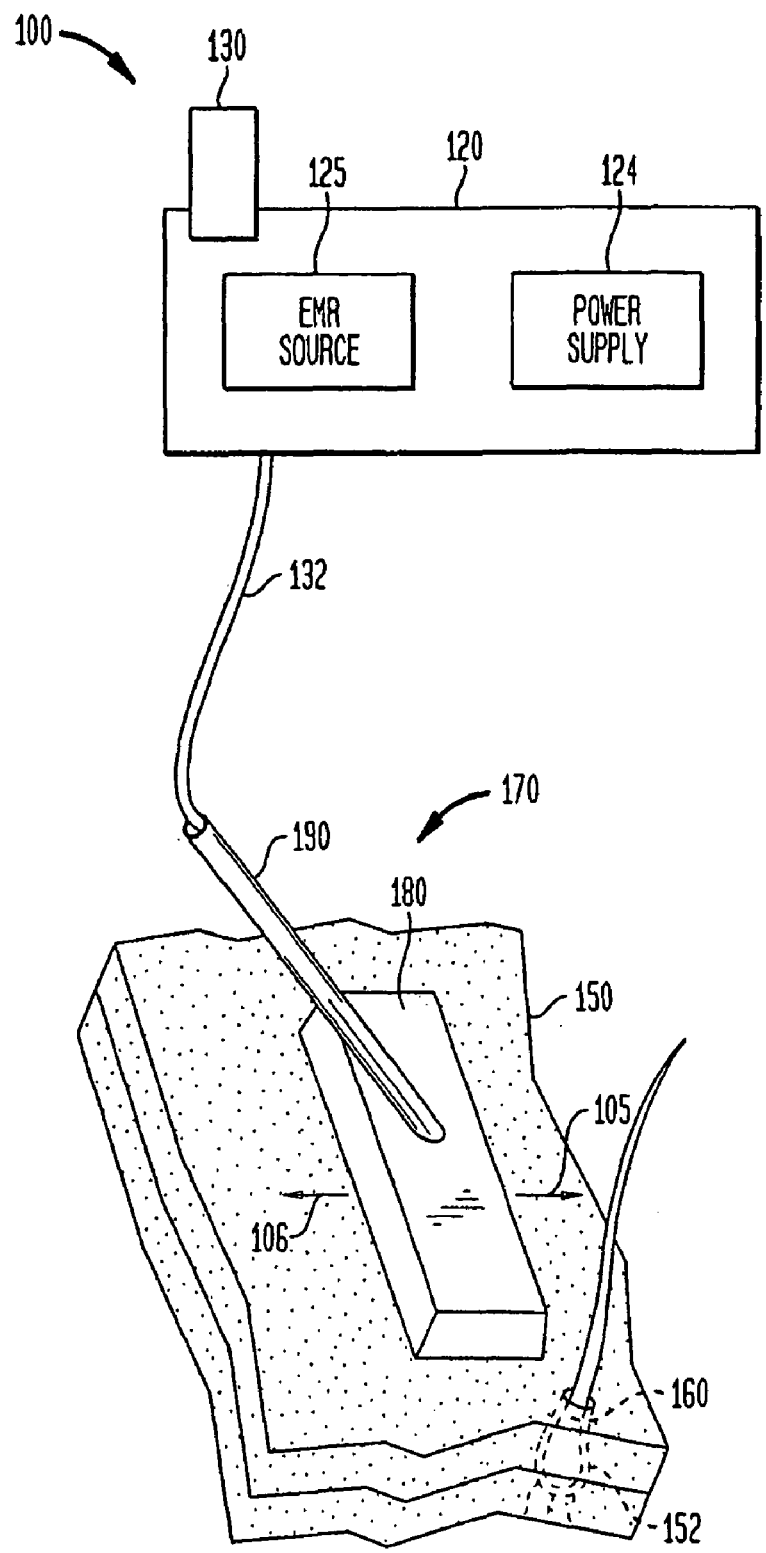
FIG. 1A is a schematic view of one example of an embodiment of a phototreatment device to treat a tissue according to aspects of the present invention.

Aspects of phototreatment devices according to the present invention, for use in medical or non-medical environments, may include, for example, the following characteristics: (1) reduced thermal tissue damage (for example, it is desirable to avoid wounds and other skin injuries); (2) improved safety and efficacy (e.g., the device increases the likelihood that the appropriate consumable substances are used; that the device is in contact with particular tissue to be treated to avoid injury to sensitive tissues (e.g., the eyes); that the device is moved over tissue within a particular range of speeds; and that treated areas are not overtreated); (3) easy maintenance (preferably maintaining a device in useable condition and replacing expended parts can be easily accomplished); (4) easy manufacture (e.g., preferably the device is manufacturable in high volume); (5) low-cost manufacture and operation (e.g., preferably the device is available and operable at a reasonable price); (6) small package size (preferably the device is small and easily stored, for example, in a bathroom); (7) improved patient comfort during treatment (i.e., the device preferably results in reduced pain from light or mechanical action); (8) ease of use (e.g., providing a visual indication of regions of tissue that have been treated or regions to be treated); (9) it is capable of providing additional aesthetic benefits (e.g., application of a self-tanning substance). Currently available phototreatment devices have limitations related to one or more of the above characteristics.

The present invention provides systems and methods for using a phototreatment device with a substance, which can provide beneficial effects to the user such as cooling the target area, providing a means for generating a safety shut-off mechanism, marking the area that has been treated, delivering therapeutic effects to the patient, etc. The substance is contained within a compartment that is coupled to the phototreatment device. The substance can be an adjuvant substance, which is either consumable or re-useable.

I. Substances: Consumable and Reuseable

The container described in the present invention can be used with an adjuvant substance. An "adjuvant substance" as used herein is intended to include both re-useable substances (i.e., phase change coolant materials) and consumable substances (i.e., topical substances and disposable coolants).

A coolant may be any suitable transportable material capable of absorbing heat. For example, a coolant may comprise tetrafluorethan (R-134a), liquid $CO_2$, ice, frozen lotion, wax or frozen gel. In some embodiments, the coolant is a phase change material (i.e., a material that changes phase in response to addition or removal of heat). Example of phase transition substances include: cristallohydrates (45% $CaCl*6H_2O$:55% $CaBr*6H_2O$ ore $KF*4H_2O$), organic materials as $HO(C_2H_4O)_8C_2H_4OH$ (PE Glycol), Caprilic acid, Hexadecane and Paraffin 5913. For example, the container may contain a pressurized gas in liquid phase (such that the liquid coolant is projected onto a target to absorb heat from the target, and in response to heat absorbed, the liquid changes to a gas), or a solid state material (e.g., a powder or granules or a block of material) with a melting temperature below the temperature of the target heat dissipating element. Various other phase changing materials may be used.

A topical substance may be any suitable transportable material to perform any suitable function. For example, a topical substance may enhance the efficacy of a phototreatment (e.g., coupling light from a source into a tissue, or by removing residual hairs), increase safety of a phototreatment device (e.g., cooling the tissue, indicating areas that have been treated, indicating rate of movement of the device over the tissue), provide comfort to a patient during or after a phototreatment (e.g., by containing mild anesthetic ingredients and/or by cooling), or provide additional benefits for the skin and subcutaneous tissue (e.g., by moisturizing skin, tanning skin, ultraviolet (UV) protection, improving skin texture and tones, improvement of skin elasticity, reduction or prevention of cellulite, decreasing the appearance of cellulite, reduction and/or prevention of acne, reduction and or prevention of wrinkles, decreasing the appearance of scars, reduction and/or prevention of vascular lesions, reduction in pore size, oil reduction in sebum secretion, reduction of sweat, reduction of odor, reduction or removal of body hair, stimulation of hair growth, etc.). In some embodiments, penetration of a tissue by topical substances may be photo-enhanced and/or the effect of the topical substance may be photo-enhanced by radiation from source 125.

According to some aspects of the present invention, a topical substance may comprise a lotion, water, alcohol, oil, gel, powder, aerosol, granular particles, cream, gel, wax, film or any other suitable substance. Exemplary topical substances are preferably: biocompatible; have a low absorption coefficient for the wavelength or wavelengths of light that effects a phototreatment (e.g., less than 1 $cm^{-1}$); and have a low scattering coefficient for the wavelength of light that effects a phototreatment (e.g., less than 10 $cm^{-1}$).

Topical substances for use with phototreatment devices operated in contact with a tissue preferably have: a refractive index close to the refractive index of the epidermis (e.g., the index may be 1.3-1.6, and preferably 1.4-1.55); a high thermal conductivity (e.g., greater than 0.1-1 W/m/K); and a good lubrication effect. It is to be appreciated that a topical substance can be applied to the treatment region by the patient or operator, or be dispensed from a suitable dispensing device. It is to be appreciated that a consumable substance may have multiple purposes and effects, for example, the consumable substance may operate both as a topical substance and a coolant. In such embodiments, a substance may be fluidly coupled to the tissue and the heat dissipating element, or the substance may be fluidly coupled only to the tissue but provide both cooling and other benefits to the tissue.

In other aspects of the present invention, efficacy and/or safety of a phototreatment may be improved where the topical substance itself (which may or may not be a coolant) or a marker (added to the topical substance) is used to designate an area to be treated, facilitate detection of motion of a phototreatment device over tissue, and/or facilitate measurement of speed of said motion.

Phase change materials can be used as re-useable substances. The phase transition of a phase change material can be from a solid phase to a liquid phase, i.e., melting of ice, or from a solid phase to a gas phase, i.e., sublimation of dry ice stored in a cartridge. The phase-change material can be employed for removing heat from the light source. Ice is a particularly good choice for the phase change material because it exhibits a high latent heat of melting and is biologically and environmentally safe. It should, however, be appreciated that any other suitable phase change material can also be utilized in the practice of the invention. In some embodiments, a frozen mixture of water and an additive, such as salt or alcohol, can be used as the phase change material. Other examples of the phase change material include gallium and wax. In general, a suitable phase change material preferably exhibits a relatively high latent heat of melting to allow efficient heat dissipation, and is biologically safe. In addition, the phase change material is preferably safe for release into the surrounding environment. Further, skin beneficial ingredients can be added to the phase change material to be released onto a portion of the patient's skin during treatment of the skin by the photocosmetic device. Such ingredients can provide beneficial and/or therapeutic effects independent of the therapeutic effects provided by the exposure of the skin to light or heating or cooling provided by the photocosmetic device. Alternatively, the skin beneficial ingredients can be photo or thermally activated by the device to provide their intended beneficial effects.

A single or multi-use cartridge containing both phase change material and skin beneficial ingredients can be configured in many ways including a) a phase change material (such as ice) mixed with skin beneficial ingredients in a single chamber or b) a phase change material and skin beneficial ingredients located in two separate chambers. The cartridge can be located either in the base unit or the handpiece and can be designed to be replaceable by the user.

For a single-use cartridge, the user would simply replace the old cartridge with a new one prior to treatment. Assuming ice is used as the phase change material to cool the light source, a supply of single-use cartridges could be kept in the freezer and used as needed.

For a multi-use ice cartridge with separate chambers for the captive ice/water and beneficial ingredients delivered to skin, the water could be refrozen after use. The multi-use cartridge could be designed to contain enough skin beneficial ingredients for 10 (nominal) treatments. If a marker was mixed in with the skin beneficial ingredients and the device was designed to activate only when the marker was detected, then the user would be forced to replace the cartridge even though the water could again be refrozen.

The lotion dispensed on the skin can contain both skin beneficial ingredients and compounds designed to improve the thermal and optical contact between handpiece and skin. In the case of a handpiece designed for unidirectional scanning across the skin surface, the lotion can be deposited on the skin either pre or post laser irradiation. By depositing a lotion designed to improve thermal and optical contact prior to laser irradiation, improved safety and efficacy can be achieved. A lotion cooled by the ice in the cartridge could be applied to the skin post irradiation to make the treatment more comfortable for the user. Whether applied pre or post irradiation, the lotion will provide lubrication, which allows the handpiece to be easily scanned across the skin surface.

II. Phototreatment Devices Coupled to a Container

FIG. 1A is a schematic view of one example of an embodiment of a phototreatment device 100 to treat a target area or tissue 150, for example, skin. Typically, photocosmetic treatments involve treating a target area located within an epidermal or dermal layer. For example, in the case of hair removal, it may be desirable to heat a bulb 152 of a hair follicle 160. Phototreatment device 100 includes a base unit 120, an umbilical cord 132 (also referred to herein as a "cord"), and a handpiece 170. According to an aspect of the present invention, phototreatment device 100 also includes a replaceable container 130 containing a consumable substance comprising, for example, a coolant or a topical substance. In other embodiments, container 130 may contain a topical substance and be fluidly connected to tissue 150.

Base unit 120 may include a power supply 124 to power an electromagnetic radiation (EMR) source 125 (also referred to herein simply as a "source"), which effects a phototreatment. Power supply 124 may be connected to an external power source or an internal battery. EMR source 125 may be any source (e.g., a laser, a lamp, an LED, or collected sunlight) capable of producing electromagnetic radiation to effect any presently-known or later-developed phototreatment. Power supply 124 may be electrically coupled to handpiece 170 via cord 132. Cord 132 is preferably lightweight and flexible.

Handpiece 170 includes a treatment head 180 (also referred to as a "head") configured to be used in proximity to tissue 150, and a handle 190 that may be grasped by an operator to move head 180 in any direction across tissue 150. For example, head 180 may be pushed across the tissue in a forward direction 105 or pulled across the tissue in a backward direction 106. Handpiece 170 may be mechanically driven by a suitable mechanical apparatus or hand-scanned manually across tissue 150. Typically, during a given stroke (i.e., movement over tissue 150), contact will be maintained between head 180 and tissue 150 while head 180 is moved, although some phototreatments according to the present invention may be achieved without contact. Firm contact between head 180 and tissue 150 is preferable to ensure good thermal and optical contact therebetween. Phototreatment device 100 is further described in U.S. application Ser. No. 10/154,756 filed May 23, 2002, entitled "Cooling System for a Photocosmetic Device," by Altshuler et al., the entirety of which is hereby incorporated by reference.

In the embodiment illustrated in FIG. 1, source 125 is located in base unit 120 and connected to head 180 via a light pipe (e.g., an optical fiber, not shown) in cord 132. The light pipe may extend through handle 190, or may be otherwise connected to head 180 to deliver light to tissue 150. In some embodiments, the source is located in the handpiece, for example, in the embodiment illustrated in FIG. 2 below, a source 252 is located in a handpiece 280.

While the above embodiment of a phototreatment device is modular (i.e., having a separated base unit and handpiece), it is to be appreciated that phototreatment devices according to aspects of the present invention can be implemented in a self-contained unit, in which an entire phototreatment device is implemented as a handheld device.

Figure 1B:
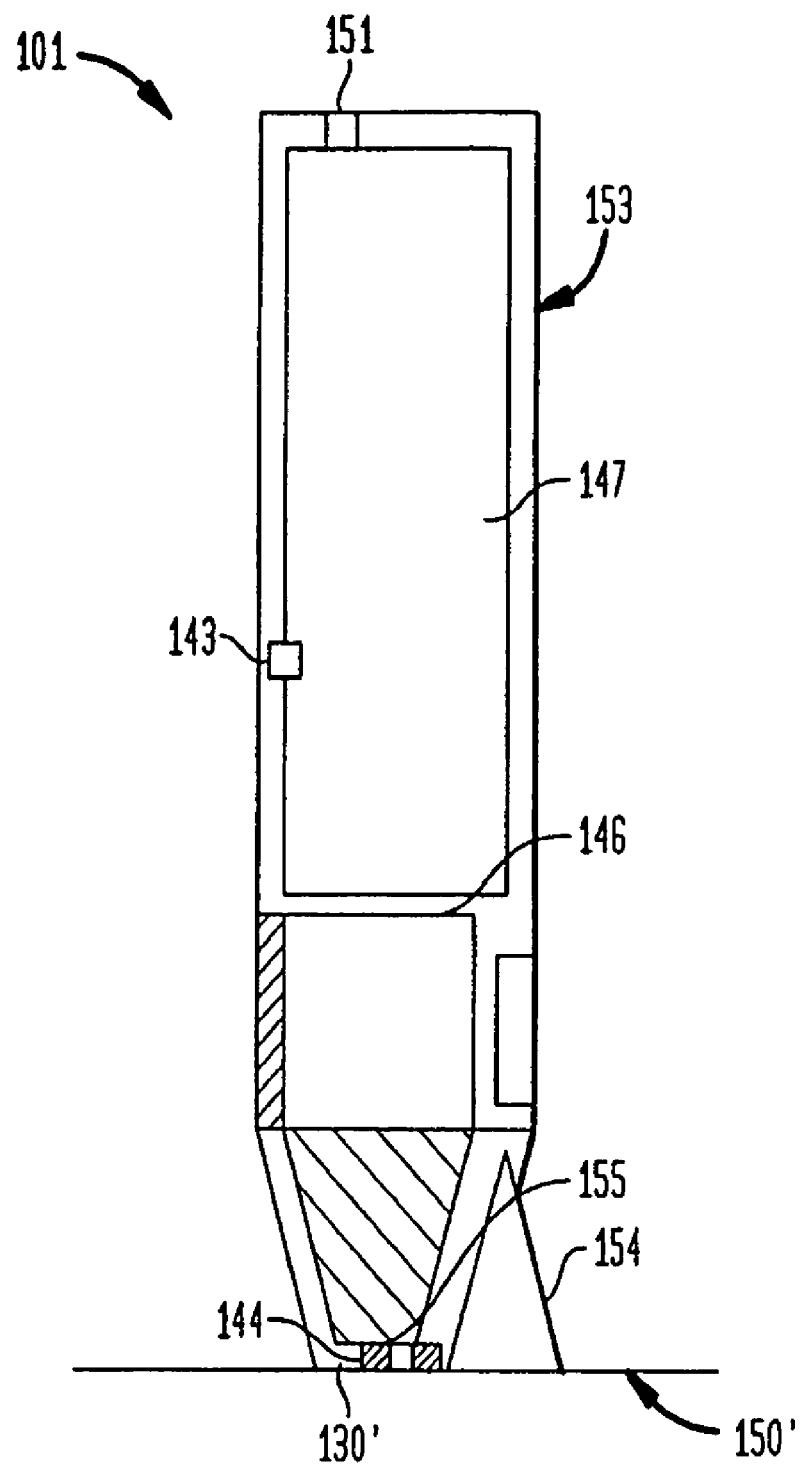
FIG. 1B is a schematic view illustrating some aspects of a self-contained phototreatment device according to the present invention.

FIG. 1B is a cross-sectional schematic of one embodiment of a self-contained photocosmetic device according to the present invention. Handpiece 101 comprises an optical source 155, an optical system 144, and a container 146 for a consumable substance. The device is shown in contact with a tissue region 150'. Optical system 144 couples light from light source 155 into a tissue region 150'.

A power supply 147 (e.g., battery or capacitor) supplies electrical current to optical source 155. In some embodiments, power source 147 may be charged via an electrical contact 151 or an electrical cord (not shown). An on/off button 143 controls the electrical power. A housing 153 may be used to enclose, protect, or mount one or more of the above parts. Optionally, a hair removal device 154 (e.g., a razor) may be located to remove hair prior to irradiation by light from optical source 155 to ensure that substantially no hair extends above the skin surface. Further details regarding self-contained devices are given in U.S. application Ser. No. 10/154,756, incorporated by reference herein above. In some embodiments, container 130' is coupled to optical source 155 or an optical system 144.

As described in greater detail below, in some embodiments, containers 130 and 130' can contain an adjuvant substance. An "adjuvant substance" as used herein is intended to include both re-useable substances (i.e., phase change materials) and consumable substances (i.e., topical substances and coolants).

In one embodiment, container 130 or 130', shown in FIG. 1A and 1B, contains a coolant and is fluidly connected to a heat dissipating element of phototreatment device 100, 101 either in the base unit or in the handpiece (for example, heat dissipating element 222 illustrated in FIG. 2 below). The coolant may instead be or may also be fluidly connected to tissue 150, 150' to cool the tissue. The phrase "heat dissipating element" is defined herein to mean any element that dissipates heat. A heat dissipating element may be a heat source (e.g., EMR source 125 or power supply 124) or an element that dissipates heat from a heat generating element (e.g., a heat sink or thermally conductive electrode).

FIG. 2 is a schematic illustration of a phototreatment device 200 according to aspects of the present invention. A handpiece 280 includes a source 252 located to direct light from a head 272 onto a target area 250 (e.g., an area of a patient's skin) on which a selected phototreatment is to be performed.

A replaceable container 210 includes a consumable substance, for example, a coolant 215, that may be fluidly connected to tissue 250 and/or a heat dissipating element 222 in handpiece 280 and/or a heat dissipating element in base unit 220 (not shown). A "fluidly connected" container is defined herein as a container configured and arranged to deliver a substance (e.g., a consumable substance) to a selected location (e.g., a tissue and/or a heat dissipating element). For example, a fluidly connected container may be directly connected to a selected location or may be connected via a conduit and/or a valve. In some embodiments, container 210 is fluidly connected to a selected location (e.g., a tissue or heat dissipating element) via a conduit 270. A consumable substance to be delivered may be any suitable transportable substance. For example, a transportable substance may be a gas, liquid, gel, powder, granules, or any substance capable of being delivered from a container to a selected location.

Consumable substances may provide any benefits as described above and may provide benefits such as improved moisture, tone, texture, skin color, or exfoliation. Additionally, for example, a consumable substance may have a suitable color or be capable of changing color after receiving light from a phototreatment device, for example, to identify regions of tissue that have been treated by a phototreatment device as described herein. As other examples, a consumable substance may be a fluorescent material for use in a measuring speed of the device over tissue as described herein, or may provide any of a variety of other benefits as will be apparent to one of ordinary skill in the art.

A conduit may allow flow of the consumable substance to only tissue 250 or only to a heat dissipating element 222. Alternatively, conduit 270 may be bifurcated to allow flow of the consumable substance to both tissue 250 through a branch 270a, and a heat dissipating element 222 through a branch 270b. Alternatively, container 210 may be coupled to two separate conduits, one to allow flow of the consumable substance to tissue 250, and one to allow flow to heat dissipating element 222. In some embodiments, conduit 270 may comprise rigid plumbing within the base unit 220, and may comprise flexible plumbing in the region of the umbilical cord 232 to allow a user to freely move and orient the handpiece 280. Conduit 270 may be located such that the consumable substance 215 is delivered onto an area of tissue 250 before, during and/or after phototreatment light is directed on the area of tissue.

As mentioned above, where a consumable substance 215 is a coolant, it may be any substance capable of absorbing heat. Preferably, the coolant is capable of efficiently absorbing heat. In some embodiments, the coolant changes phase as a result of absorbing heat from heat dissipating element 222 or tissue 250. The coolant may be a liquid that becomes gaseous; or a solid or gel that becomes liquid or gaseous. For example, the coolant may be a pressurized liquid, such as liquid carbon tetrafluoride or liquid $CO_2$, or the coolant may be a solid, such as ice, frozen lotion or frozen gel that evaporates and/or liquifies upon absorbing heat from a selected location (e.g., heat dissipating element 222 or tissue 250). In other embodiments, the coolant may be a super-cooled liquid (i.e., liquid cooled below nominal freezing temperature of its principal component).

Consumable substance 215 may be pressurized using any known method such that the consumable substance may be projected onto a selected location upon release of the pressure via conduit 270. For example, consumable substance 215 may be mechanically compressed by reducing the volume of container 210 (e.g., by a spring, repelling magnets, or other suitable apparatus for applying pressure). In some embodiments, consumable substance 215 is a liquefied gas under pressure, where container 210 includes a portion of liquefied gas 215 and a portion of gas 218. In some embodiments, the pressure in the container projects a portion of liquefied gas 215 to a selected location. Alternatively, any suitable consumable substance 215 may be pressurized and projected by adding any suitable pressurized gas 218.

It is to be appreciated that a consumable substance may include a combination of materials. For example, a consumable substance 215 may comprise a coolant and a topical substance such that the consumable substance may be applied to tissue 250 and a heat dissipating element 222.

One or more valves 230, 233, 234 may be included to control the release of consumable substance 215. Valves 230, 233, 234 may be any valves controllable using electrical, mechanical, magnetic controls or any other suitable valves. In some embodiments, one or more of valves 230, 233, 234 may be controllable based on speed of movement across the skin as measured by a motion sensor 240, or a temperature measured at the skin by a temperature sensor 242 or a temperature measured at heat dissipating element 222 by a temperature sensor 243. Motion sensor 240 and temperature sensors 242 and 243 are described in greater detail in U.S. application Ser. No. 10/154,756, incorporated by reference herein above.

Valves 230, 233, 234 may be located in any suitable location to control the release of consumable substance 215. In some embodiments, a valve 230 is connected to container 210 or located in base unit 220, thereby avoiding adding to the size and weight of umbilical cord 236 or handpiece 280. In other embodiments, one or more valves 233 and 234 are located in handpiece 280, proximate a selected location (e.g., proximate tissue 250 or a heat dissipating element 222). For example, locating one or more valves in a handpiece 280 allows a pressurized liquid coolant 215 to be maintained in a liquid state to facilitate projecting the coolant onto the selected location in a liquid state; accordingly, as described above, the liquid coolant may change phase as a result of heat absorbed from a selected location.

In some embodiments, valve 230 is a displacement valve connected to container 210, and base unit 220 has a corresponding pin to displace valve 230 such that upon proper positioning of container 210, valve 230 is activated and consumable substance 215 fills conduit 270. Optionally, container 210 and base unit 220 may be threaded such that container 210 is screwed into base unit 222.

In some embodiments, base unit 220 maintains container 210 in a specific orientation. For example, container 210 may be maintained in an orientation such that valve 230 is at the bottom container 230 (i.e., gravity allows consumable substance 215 to flow through valve 230).

Although only one container is illustrated, phototreatment devices comprising two or more containers each containing a consumable substance, such as coolants and/or topical substances, are within the scope of the invention. As one of ordinary skill will understand, in the case of two or more such containers, each of the containers is fluidly connected to one or more selected locations.

According to some embodiments of the invention, two containers may be connected to a single conduit or separate conduits that meet at the same target location to allow the consumable substances in the two containers to be physically or chemically combined either prior to or upon arrival at the selected location. Allowing two or more topical substances to be mixed may provide a great many benefits. For example, the mixture of the topical substances may provide an improved topical substance or coolant. Additionally, the two or more topical substances may have longer shelf life if kept in separate containers, or the mixture of the topical substances may cause a chemical reaction providing different benefits than either substance alone. For example, the combining of the consumable substances may result in an endothermic reaction that provides cooling or an active substance for topical application (e.g., an exfoliant, hair removal substance or self tanning compound).

Figure 3A:
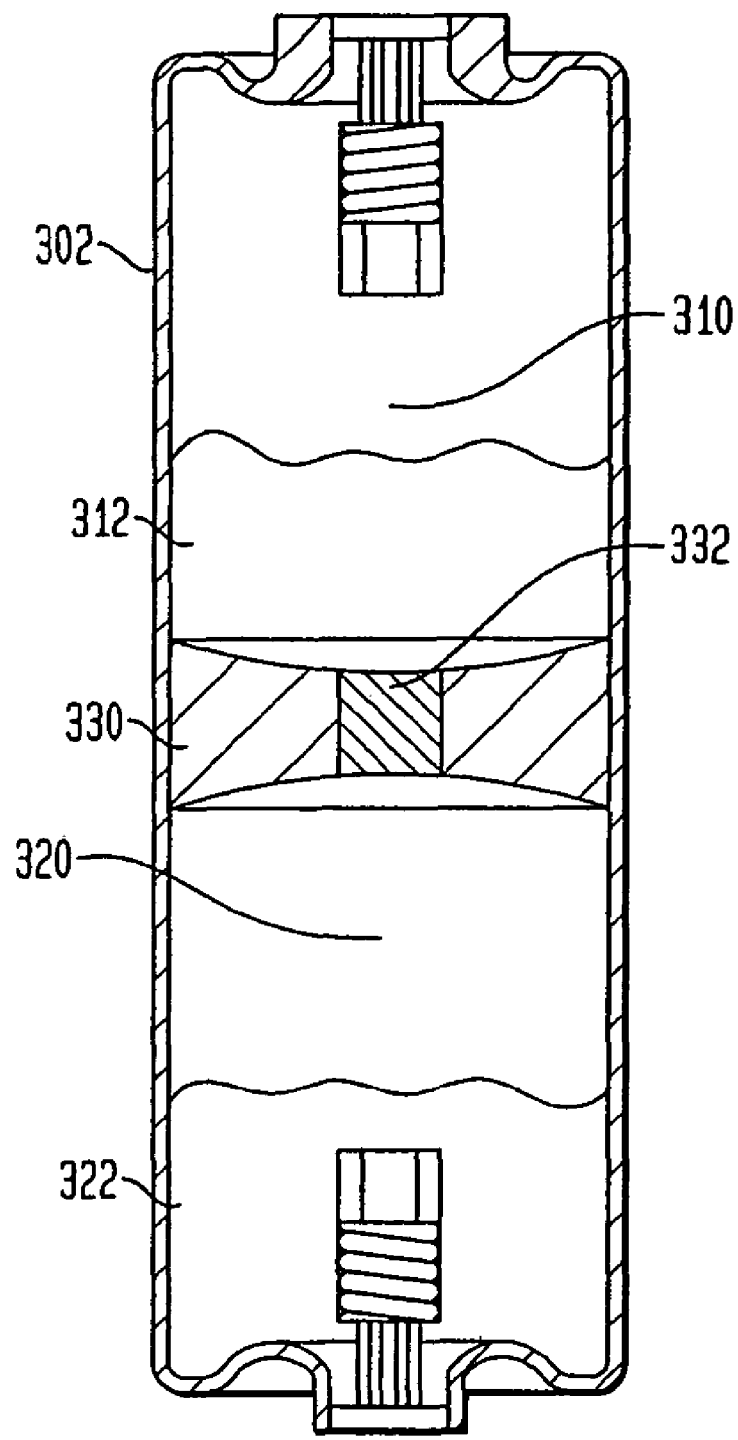
FIG. 3A is a cross-sectional view of a first example of a container comprises a first compartment fluidly connectable to a tissue, and a second compartment fluidly connectable to a phototreatment device.

FIG. 3A is a cross-sectional side view of an example of a container 300 according to an aspect of the invention. Container 300 comprises a first compartment 310 fluidly connectable to a tissue, and a second compartment 320 fluidly connectable to a head or base unit of the phototreatment device. A "fluidly connected compartment" is defined as a compartment configured and arranged to deliver a consumable substance to a selected location. For example, a fluidly connected compartment may be directly connected to a selected location or may be connected via a conduit and/or a valve, as described above with respect to FIG. 2. A "fluidly connectable compartment" is defined herein to be a compartment capable of being arranged to deliver a consumable substance to a selected location. It is to be appreciated a fluidly connectable compartment may provide for the flow of liquids, gases, gels, or suitable solids (e.g., powder or granules).

First compartment 310 and second compartment 320 each contain a corresponding consumable substance 312 and 322. Consumable substances 312 and 322 may be any consumable substances suitable for use with a phototreatment device as described herein. In some embodiments, at least one of consumable substances 312 and 322 is suitable for application on a tissue as a topical substance which may or may not cool the tissue and the other is a coolant for a heat dissipating element as described above with reference to FIG. 2.

First compartment 310 and second compartment 320 may be separated by any divider 330 capable of separating consumable substances 312 and 322. The divider may be rigid or flexible; divider 330 may be fixed to a wall 302 of container 300, or may be moveable relative to wall 302. In some embodiments, there may be more than one divider present.

In some embodiments, first compartment 310 and second compartment 320 are in pressure communication. The phrase "pressure communication" is defined herein to mean that a pressure in one of first compartment 310 and second compartment 320 is applied to the other compartment, respectively. Preferably, pressure communication allows the first compartment 310 and second compartment 320 to have equal pressure therein.

First compartment 310 and second compartment 320 may be separated by a divider 330 capable of maintaining pressurized gas in one or both of compartments 310 and 320. For example, to achieve pressure communication, divider 330 may be fixed to wall 302 and have a valve 332 to allow the flow of pressurized gas (e.g., a propellant) from compartment 320 to compartment 310; alternatively, divider 330 may be moveable relative to wall 302 (e.g., the divider may be a plunger, such as a plunger used in a syringe) such that divider 330 moves relative to wall 302 to maintain a pressure in compartments 310 and 320.

Although first compartment 310 and second compartment 320 are illustrated as being disposed end to end, any suitable arrangement in which compartments 310 and 320 are fluidly connectable to a tissue and a heat dissipating element, are within the scope of this invention. Further exemplary embodiments of containers having a first compartment and second compartment in pressure communication are illustrated below with reference to FIGS. 3B and 3C. It is to be appreciated that any of the embodiments illustrated in FIG. 3A-3C may include an indicator as described herein.

Figure 3B:
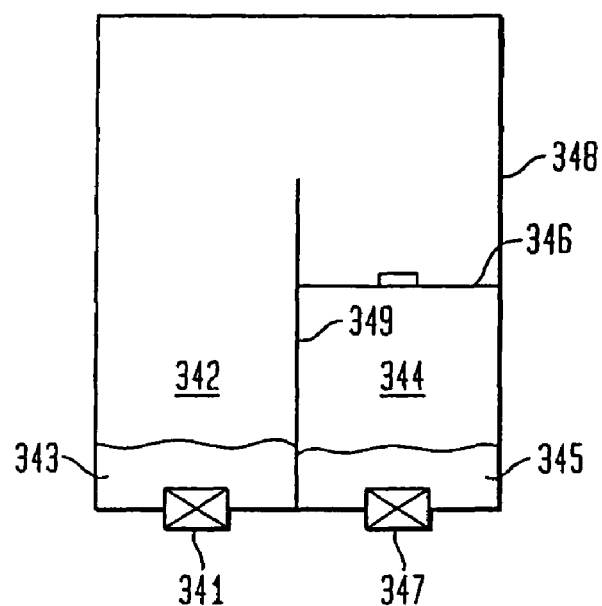
FIG. 3B is a cross-sectional view of a second example of a container comprises a first compartment fluidly connectable to a tissue, and a second compartment fluidly connectable to a phototreatment device.

FIG. 3B is a cross-sectional view of a second example of a container 340 that includes a first compartment 342 fluidly connectable to a tissue through a port 341 (e.g., a valve) and having a consumable substance 343, and a second compartment 344 fluidly connectable to a heat dissipating element through a port 347 and having a consumable substance 345. First compartment 342 and second compartment 344 are disposed side-by-side, and separated by a wall 349 and a divider 346. Divider 346 is moveable relative to walls 348 and 349 such that first compartment 342 and second compartment 344 are in pressure communication. As an alternative to a moveable divider 346, a valve may be used to provide pressure communication.

While FIG. 3B was discussed with compartment 342 fluidly connectable to a tissue and compartment 344 fluidly connectable to a heat dissipating element, respectively, it is to be understood that first compartment 342 may be fluidly connectable to a heat dissipating element and/or a tissue, and second compartment 344 may be fluidly connectable to tissue and or heat dissipating element.

Figure 3C:
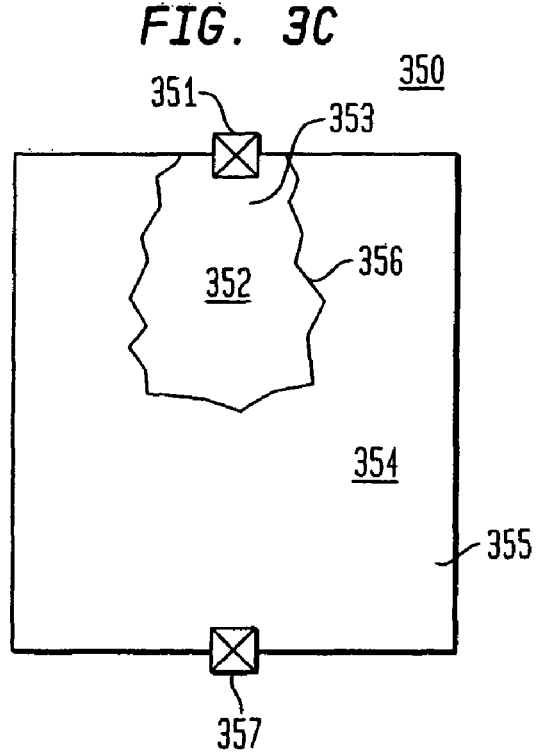
FIG. 3C is a cross-sectional view of a third example of a container comprises a first compartment fluidly connectable to a tissue, and a second compartment fluidly connectable to a phototreatment device.

FIG. 3C is a cross-sectional view of a third example of a container 350 that includes a first compartment 352 having a consumable substance 353 fluidly connectable to tissue through a port 351, and a second compartment 354 having a consumable substance 355 fluidly connectable to a head of a phototreatment device through a port 357. First compartment 352 and second compartment 354 are separated by a flexible divider 356 such that first compartment 352 and a second compartment 354 are in pressure communication. For example, flexible divider 356 may be a plastic bag.

Divider 356 allows a pressurized gas (e.g., a propellant) to be maintained in a first of compartments 352 and 354, and maintains a pressure in the other of compartments 352 and 354. Divider 356 is compressed or expanded (depending on which of compartments 352 or 354 has greater pressure).

While FIG. 3C was discussed with compartment 352 fluidly connectable to a tissue and compartment 354 fluidly connectable to a heat dissipating element, respectively, it is to be understood that compartment 352 may be fluidly connectable to a heat dissipating element and/or tissue, and 354 may be fluidly connectable to tissue and/or a heat dissipating element.

Figure 4A:
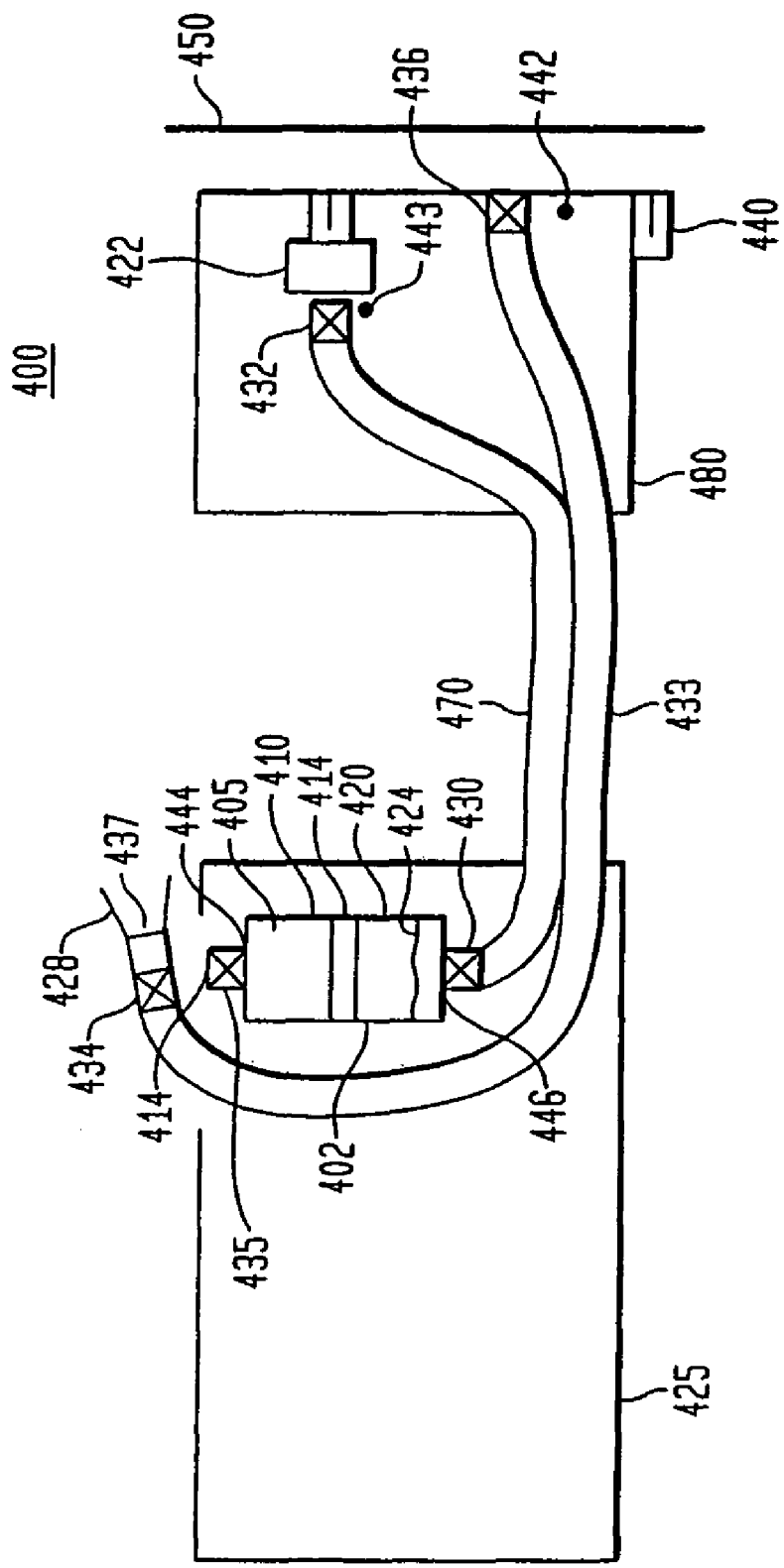
FIG. 4A is a schematic view of an exemplary embodiment of an application system for use with a replaceable container comprises a first compartment fluidly connectable to a tissue, and a second compartment fluidly connectable to a head of a phototreatment device.

FIG. 4A is a schematic of an exemplary embodiment of an application system 400 for use with a container 405 comprised of a first compartment 410 fluidly connectable to a tissue, and a second compartment 420 fluidly connectable to a head 480 of a phototreatment device.

In FIG. 4A, a first fluid connection is made to first compartment 410, and a second fluid connection is made to second compartment 420. First compartment 410 of container 405 may be fluidly connected to tissue 450 in any suitable manner, such as described above with reference to FIG. 2, and a second compartment 420 may have a fluid connection to a heat dissipating element 422 of head 480, such as described above with reference to FIG. 2.

In FIG. 4A, valves 430 and 432 may be used to control the flow of a consumable substance 424. One or more valves 434, 435, 436 may be used to control the flow of consumable substance 414 from first compartment 410. Valve 435 may be a displacement valve, and base unit 425 may have a pin 437 which displaces valve 435, such that upon displacement of the valve 435, consumable substance 414 fills conduit 433. In some embodiments, pin 437 is located on a spring-activated door 428, such that when door 428 is closed, pin 437 activates valve 435. One or more additional valves 434, 436 may be added to control the flow of consumable substance 414, for example, flow may be controlled based on speed of movement across the skin as measured by a motion sensor 440, or a temperature measured at the skin by a temperature sensor 442 or a temperature measured at a heat dissipating element 422 by a temperature sensor 443. For reasons described above, one or more of valves 432 and 436 may be located proximate a selected target location.

In some embodiments, base unit 425 maintains container 405 in a specific orientation. For example, container 405 may be maintained in an orientation to facilitate flow of fluid 424 through a conduit 470 by pressure generated by a propellant.

In some embodiments, a connection 444 by which container 405 connects to base unit 425 is different than a connection 446 by which container 405 connects to base unit 425. Referring to FIGS. 4C and 4D, connections 444 and 446 are illustrated in greater detail. In FIG. 4C, 490 is a top view of container 405 and in FIG. 4D 492 is bottom view of container 405. For example, connections 444 and 446 may have different characteristics, such that each of valves 435 and 430 is activated only if the connections 444, 446 are appropriate. Such connections are commonly referred to as "lock and key" mechanisms. Accordingly, selective activation of valves 435 and 430 is achieved, such that consumable substance 414 is prevented from reaching heat dissipating element 422 and consumable substance 424 is prevented from reaching tissue 450. For example, this may prevent accidental upside-down or reverse insertion of container 405 in system 400, and thereby improve safety and efficacy (e.g., the device connections 444, 446 reduce the likelihood that inappropriate consumable substances are used).

A lock and key mechanism may achieve selective activation by configuring connections 444 and 446 based on characteristics including, but not limited to shape, size, and threads. For example, only if a connection 444 or 446 is appropriate, is the corresponding valve 435, 430 activated (e.g., pin 437 (shown in FIG. 4A) activates a displacement mechanism of a valve 435). Alternatively the lock and key mechanism may achieve selective activation based on electrical, magnetic, or piezoelectric characteristics. For example, only if a connection 444 or 446 provides an appropriate electric or magnetic signal, is the corresponding valve activated.

Figure 4B:
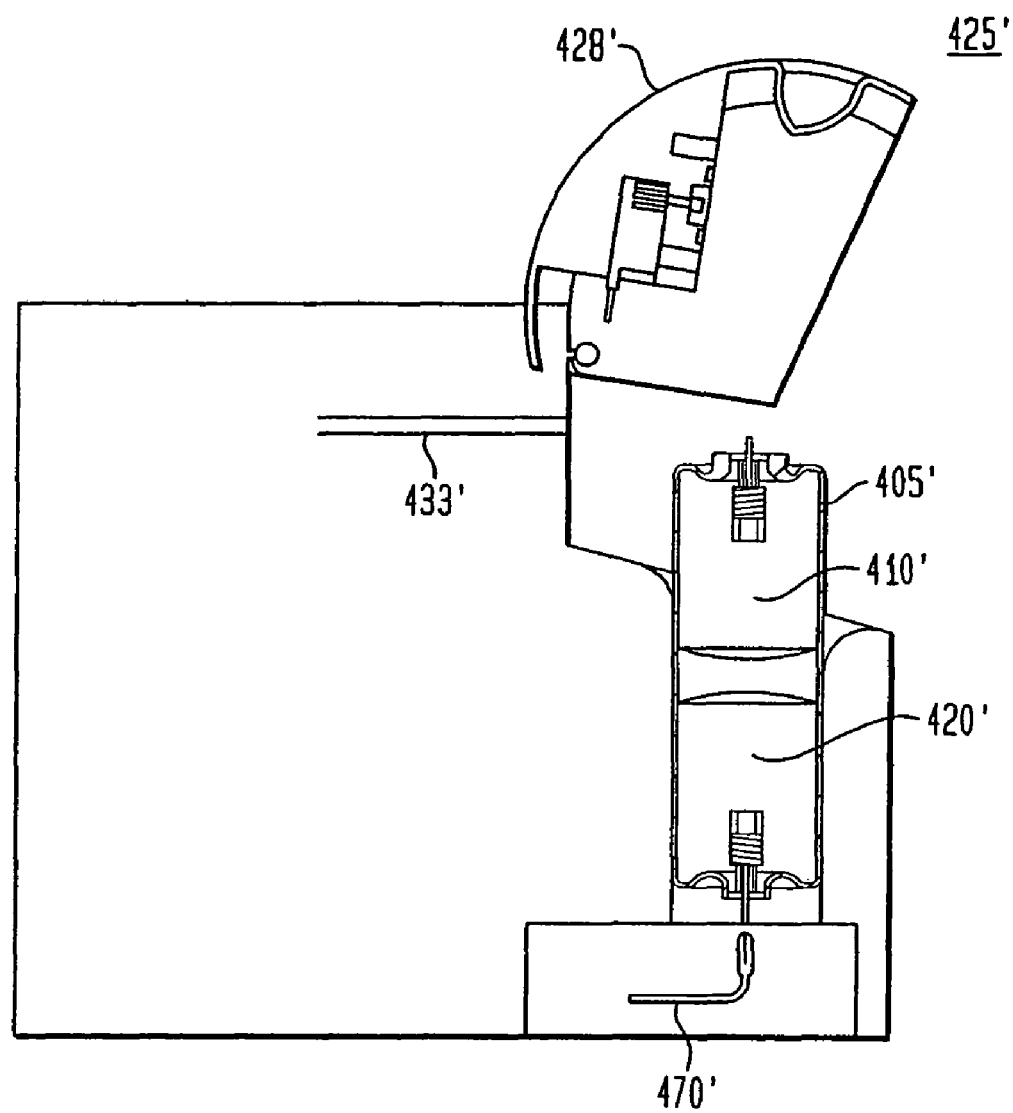
FIG. 4B is a second schematic view of an exemplary embodiment of an application system for use with a replaceable container comprises a first compartment fluidly connectable to a tissue, and a second compartment fluidly connectable to a head of a phototreatment device.
Figure 4C:
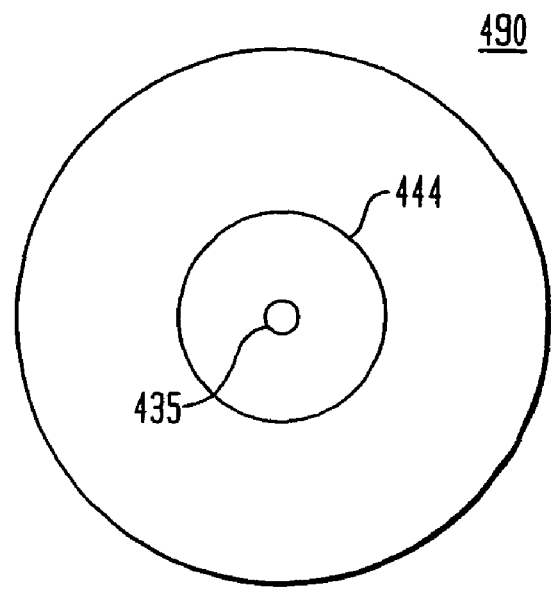
FIG. 4C is a top view of an embodiment of a container.
Figure 4D:
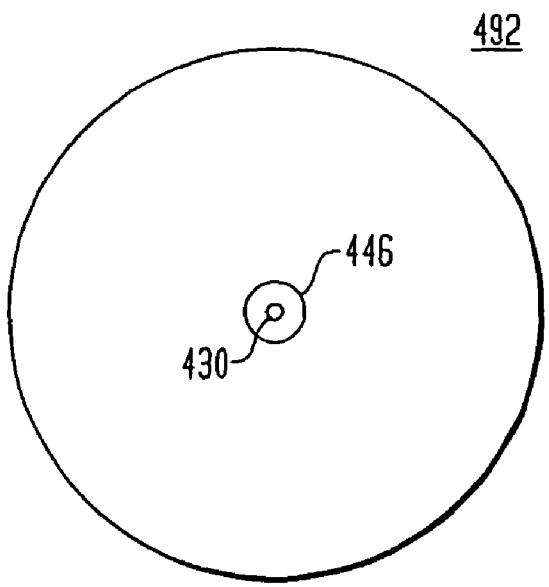
FIG. 4D is a bottom view of an embodiment of a container.

FIG. 4B is a schematic view of an exemplary embodiment of an application system 425 for use with a container 405' comprising a first compartment 410' fluidly connectable to the tissue (not shown), and a second compartment 420' fluidly connectable to a head (not shown) of a phototreatment device (e.g., container 300 shown in FIG. 3A above). Application system 425' has a spring-loaded lid 428' with a conduit 433' to the tissue and a conduit 470' to a heat dissipating element. Consumable substances within container 405' may be applied to the target location as described with respect to FIG. 2 above.

Figure 5A:
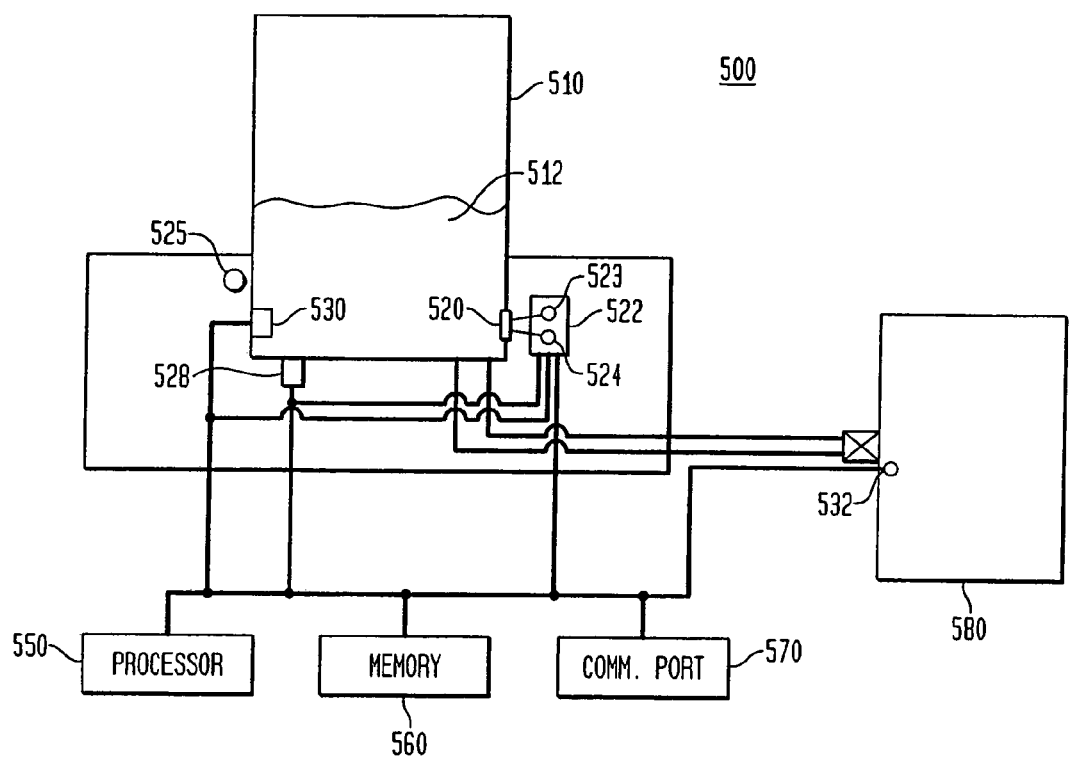
FIG. 5A is a first schematic view of a phototreatment device having an indicia-based, detection and enablement system for use with a phototreatment device.

FIG. 5A is a schematic view of a phototreatment device 500 having an indicia-based, detection and enablement system. Phototreatment device 500 includes a container 510 comprising a consumable substance 512 and an indicator 520. Container 510 is fluidly coupled to the head 580 and/or the tissue to be treated. Phototreatment device 500 also comprises an indicia detector system 522 comprising a detector 524.

Indicator 520 may be any indicator of a consumable substance 512. Indicator 520 may be an optical indicia, a magnetic indicia, an electronic indicia, a piezoelectronic indicia or any known or yet to be developed indicia. Indicator 520 may be attached to the outside of the container 510, may be integrated into the material comprising container 510, or may be within container 510 and detectable through the material comprising container 510. Indicator 520 may contain information identifying any aspect of the consumable substance. For example, the indicator 520 may indicate a manufacturer of the consumable substance or container 510, a manufacturing lot number of the consumable substance or the container, a date on which the container or contents of the container were made, the location where the container or contents of the container were made and/or an expiration date of the contents. Indicator 520 can also indicate the amount of consumable substance within container 510 both when it is connected to the phototreatment device and as the consumable substance is used.

In some embodiments of phototreatment device 500, indicator detector system 522 simply detects the presence of a container. For example, source 523 may project light onto container 510, such that detector 524 detects light reflected from container 510; alternatively, light projector 523 may project light to a detector 525, such that in absence of container 510 light is detected by detector 525, and in the presence of container 510, light is prevented from reaching detector 525. Alternatively, a mechanical detector 528 may be displaced by container 510 to detect the presence of container 510.

In some embodiments, indicator detector system 522 obtains information from the indicator 520 using a suitable method of reading indicia. For example, detector system 524 may comprise an optical detector, magnetic detector, an electronic detector, a piezoelectronic detector, or any other suitable indicia detector to detect and/or read any known or yet to be developed indicia. In some embodiments, indicator detector system 522 may include a source 523 (for example, optical detectors systems such as bar code systems may require an optical source).

Detector system 522 may also include electronic components that can enable or disable the phototreatment device

500. For example, after reading indicator 520, electronic components within detector system 522 may determine if the indicia is one of an acceptable set of indicia. If the indicia is acceptable, then detector system 522 may enable phototreatment device 500, or any component of phototreatment device 500. If the indicia is not acceptable, then detector system 522 may disable or not enable phototreatment device 500. For example, phototreatment device 500 may be enabled through an electronic switch within or coupled to detector system 522, or through additional electronics within or coupled to detector system 522 through an enabling signal. Detector system 522, therefore, can prevent an inappropriate container 510 from being used with phototreatment device 500, thereby protecting the system and the person being treated. Detector system 500 may be one of several safety systems within phototreatment device 500 and the several safety systems may provide a safety loop whereby if any one safety system detects a problem, device 500 is disabled or is not enabled.

Optionally, indicator detector system 522 may be coupled to a processor 550, and processor 550 may enable or disable phototreatment device 500. In addition, processor 550 may be coupled to a memory 560. Indicator detector system 522 may detect indicator 520, and the processor may record the detected indicia in memory 560 and/or the processor may display data included in the indicia. Data detected by detector 524 may be processed by phototreatment device 500 or any other device (such as a diagnostic device). The processing of the data by processor 550 may occur before, after, simultaneously, or instead of storage in memory 560. The data processed by processor 550 may be used to configure or adjust parameters of phototreatment device 500. For example, the fluence, pulse width, wavelength or any other parameter of phototreatment device 500 may be changed depending upon the type of container detected through the indicator as being connected to the phototreatment device. As a result, multiple acceptable indicia may correspond to different containers containing different consumable substances and the processor may change the parameters of the phototreatment device to optimize the treatment for each particular consumable substance. In addition, each container and/or consumable substance may correspond to a different type of treatment and the processor detection of a particular container would correspond to a particular treatment for which the processor would adjust the parameters accordingly.

In addition to or instead of the indicator detector system 522, one or more detectors 528, 530, 532 may be arranged to identify the consumable substance 512. Detectors 528, 530, 532 may be any suitable detector, such as those described above, for identifying consumable substance 512. Detectors 528, 530, 532 may use any physical, optical, electrical, mechanical, chemical, or other mechanism for identifying a characteristic of consumable substance 512, to thereby identify consumable substance 512. For example, a detector may determine the chemical composition, the color, or the viscosity of a consumable substance.

Alternatively, a marker may be added to consumable substance 512 to identify the consumable substance, such that the marker is detected by detectors 528, 530, 532. The marker may be any suitable additive, such as those described above, capable of detection by any of the above described methods and mechanisms. For example, the marker may be a dye capable of optical detection, or the marker may have a detectable chemical composition, or may have detectable magnetic properties, or it can be a fluorescent material such that the additive is detected by projecting light onto the additive.

Detectors 528, 530, 532 may be located at any appropriate location. For example, a detector (e.g., detector 530) may be located inside container 510 or integrated with container 510 and coupled with detector system 522 or processor 550 in phototreatment device 500. The detector may be coupled to detector system 522 by an electrical connection (e.g., metal contacts with or without a wire to detector system 522) or by wireless communication (e.g., electromagnetic pulse(s)). Alternatively, or in addition to detector 530, a detector 528, 532 may be located within phototreatment device 500 and in the path of the consumable substance 512 such that they can identify the consumable substance or marker as it enters phototreatment device 500 from container 510 (e.g., detector 528) or as it enters handpiece 580 (e.g., detector 532). It is to be appreciated that any of detectors 528, 530, 532 can be electrically coupled to any one or more of detector system 522, processor 550, and a memory 560, for example, a bus line or other electrical connection may be implemented.

After identifying the consumable substance or marker, detector system 522 or processor 550 may determine if the consumable substance or marker is one of an acceptable set of consumable substances or markers. If acceptable, then detector system 522 or processor 550 may enable phototreatment device 500, or any component of phototreatment device 500. If the consumable substance or marker is not acceptable, then detector system 528 or processor may disable or not enable phototreatment device 500 or a selected one or more components of phototreatment device 500. Identifying the consumable substance or marker, ensures that the phototreatment device will only function with a container filled with appropriate consumable substances or markers, thereby further protecting the phototreatment device from damage and the person being treated.

In some embodiments of phototreatment device 500, a communications port 570 is included to enable data to be transmitted from phototreatment device 500 to external computer systems. For example, the data may be transmitted for diagnostic purposes, or for assisting a user in operating the device. Communications port 570 may be wired or wireless.

Figure 5B:
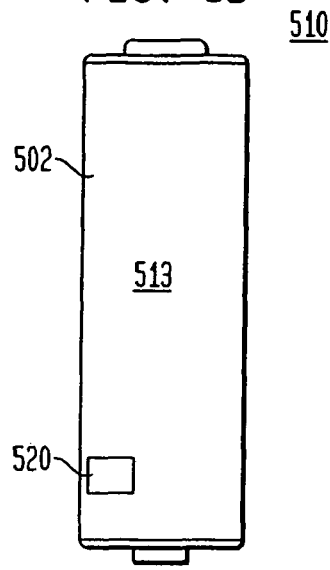
FIG. 5B is a schematic view of a container for use with an indicia-based detection and enablement system.

FIG. 5B is an enlarged view of a container 510 for use with an indicator-based detection and enablement system. Container 510 comprises a compartment 502 to contain a consumable substance (not shown) therein. Compartment 502 is fluidly connectable to a head or base unit of a phototreatment device or tissue (not shown). Container 510 further comprises an indicator 520.

Container 510 may be any container capable of containing a consumable substance. For example, container 510 may be a two-compartment container (shown in FIGS. 3A-3C) and/or a container having a thermally conductive region (shown in FIG. 6); however, container 510 is not limited to such containers. The consumable substance may be any consumable substance suitable for use with a phototreatment device. For example, consumable substance may be a topical substance and/or coolant as described herein above.

III. Photocosmetic Device Cooling Systems

Figure 6:
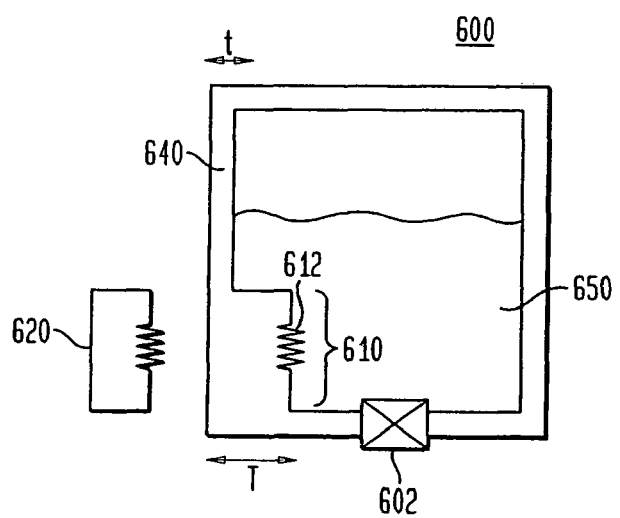
FIG. 6 is a schematic view of a container having a region to cool a heat dissipating element in a phototreatment device.

FIG. 6 is a schematic view of a container 600 having a region 610 configured and arranged to cool a heat dissipating element 620 in a phototreatment device. Container 600 is arranged to be in thermal contact with heat dissipating element 620. Container 600 may be constructed of any thermally conductive material (e.g., a metal), comprising a compartment 640 and configured to contain a substance capable of cooling heat dissipating element. The substance can be any suitable substance, for example, ice, frozen gel, frozen lotion or other coolant.

In some embodiments, the substance is not a consumable substance (i.e., the substance is not a topical substance and it remains in the container). In such embodiments, the container may be re-used (i.e., after the container has reached a temperature where it can no longer adequately cool, it may be re-cooled or re-frozen).

In some embodiments, container 600 is configured to contain a liquified gas 650 that is maintained in a liquid state by pressure. Container 600 is fluidly connectable to a head of a phototreatment device and/or tissue (not shown) via any suitable connector 602. According to well known laws of thermodynamics, as liquified gas 650 is released from container 600, some of the liquified gas within compartment 640 will experience a phase change from liquid to gas, and thereby reducing the temperature of liquified gas 650 and that of at least region 610 of container 600. Accordingly, region 610 may be thermally coupled to a heat dissipating element 620 to remove heat from the heat dissipating element. Liquified gas 650 may be a coolant and/or a topical substance as described herein, which is capable of being pressurized to form a liquified gas.

In some embodiments of container 600, only region 610 is constructed of a thermally conductive region, so that heat is selectively dissipated at region 610, and the remainder of container 600 is thermally insulated such that heat selectively flows through region 610. In some embodiments, region 610 has a thickness T that is larger than the thickness t of other regions of container 600 and, optionally, region 610 comprises a textured surface 612 for improving heat transfer.

Figure 7:
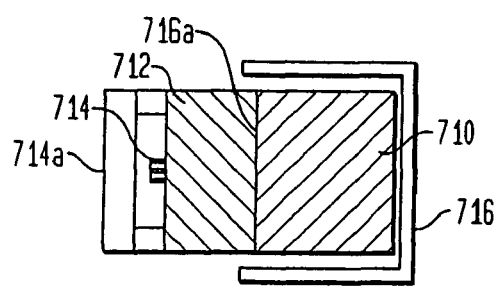
FIG. 7 is a block diagram that schematically depicts an exemplary embodiment of the invention in which the phase change medium is in direct thermal contact with a heated element incorporated in a photocosmetic device, to cool the heated element during operation of the device.

With reference to FIG. 7, in some embodiments of the invention, a phase change material 710, such as ice, is in thermal contact with a heat transfer element 712 incorporated in a photocosmetic device, for example, in a handpiece of such a photocosmetic device, that transfers heat from a heat generator, e.g., light source 714, electronics and contact tip 714a to the phase change material during the operation of the light source and/or between operation. The transferred heat can cause a phase transition in the phase change material, for example, a transition from a solid phase to a liquid phase, thereby providing a mechanism for removing heat from the light source. In other words, the heat extracted from the light source by the heat transfer element 712 which thermally contacting to tip 714a and electronics provides the heat required for causing the phase transition of the phase change material. In this exemplary embodiment, the phase change material is contained within an enclosure 716 having an opening 716a that allows direct contact between the phase change material and the heat exchanger. The surfaces of the phase change medium and the heat transfer element that are in contact with one another are preferably shaped to optimize heat transfer from the heat transfer element to the phase change medium. In general, the enclosure 716 is preferably formed of a thermally low conductive material. In some embodiments, the phase change material 710 can be in thermal contact with the heat transfer element 712 via a portion of the enclosure 716. In other embodiments, the phase change material can be in direct contact with the light source without the intervention of the heat transfer element 712. An optical element 714a, which directs radiation from the light source 714 to a portion of a patient's skin, can also be in thermal contact with the heat transfer element to ensure that its temperature remain in a range that is not damaging to the patient's skin.

Figure 8A:
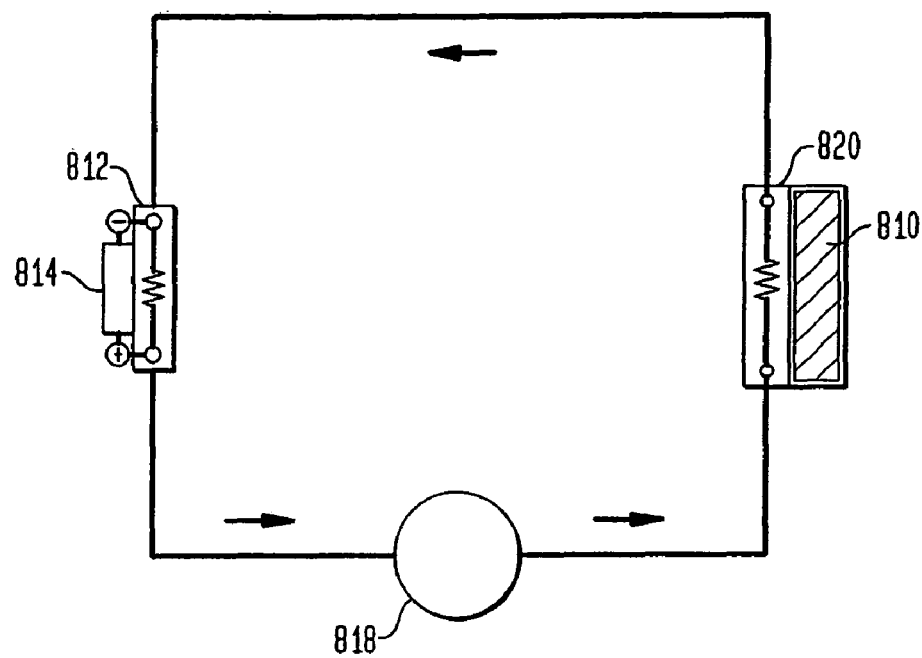
FIG. 8A is a block diagram that schematically depicts another exemplary embodiment of the invention in which a phase change material is employed to extract heat from a circulating fluid that cools a light source of a photocosmetic device.

With reference to FIG. 8A, in another exemplary embodiment of the invention, a circulating cooling fluid, such as water, is utilized to remove heat from the heat transfer element 812, which in turn extracts heat from the light source 814 (or other heated element). A pump 818 circulates the cooling fluid from the heat transfer element 812 to another heat exchanger 820 that transfers heat from the cooling fluid to the phase change material 810, such as ice, that is in thermal contact with the heat exchanger 820. The transferred heat is dissipated by causing a phase transition of the phase change material, for example, from a solid state to a liquid state. In this exemplary embodiment, the second heat exchanger 820 can be incorporated in the photocosmetic device, for example, in a base unit thereof. The phase change material can be prepared for use in the device externally, and then be placed in thermal contact with the heat exchanger 820 to extract heat therefrom via a phase transition to a different state. Subsequent to the phase transition, the material can be removed from the photocosmetic device, and the cycle can be iterated. For example, when the phase change material is ice, a selected quantity of water can be frozen in an external freezer to form ice, and the ice can then be placed in thermal contact with the heat exchanger 820. Upon melting of the ice, the generated water can be removed. Alternatively, a cooling device, such as a thermo-electric (TE) cooler can be provided in the photocosmetic device for re-generating the phase transition material in a state suitable for extracting heat from the heat exchanger, without removing the material from the photocosmetic device, after a phase transition caused by the heat transferred from the heat exchanger to the phase change material. That is, in this example, the TE cooler can freeze the water back into ice.

Figure 8B:
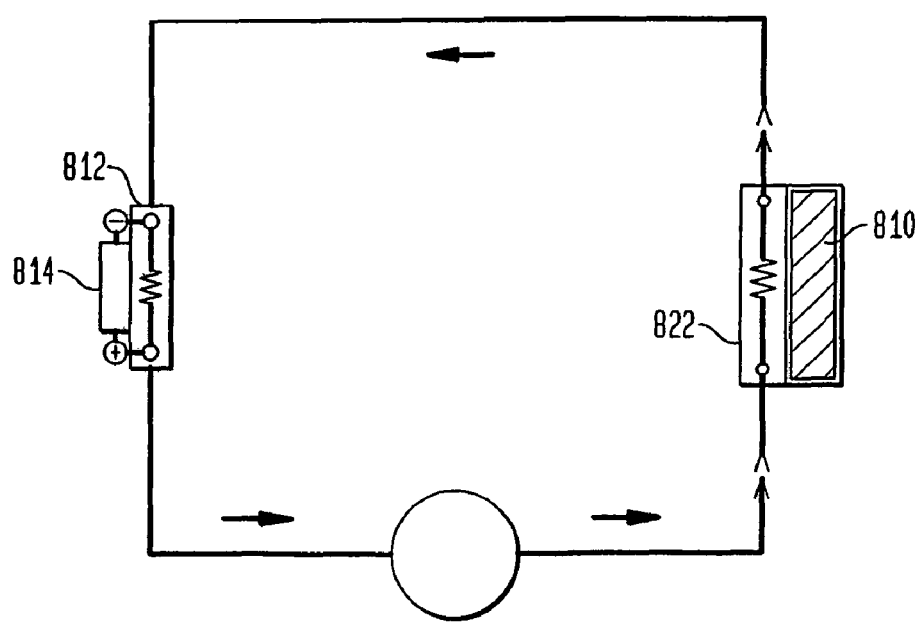
FIG. 8B is a block diagram that schematically depicts yet another exemplary embodiment having a removable heat exchanger that can be coupled to a photocosmetic device to transfer heat from a circulating cooling fluid, which extracts heat from a light source of the device, to a phase change material.

With reference to FIG. 8B, in another embodiment, a circulating fluid transfers heat from the heat transfer element 812, which is thermally coupled to the light source 814 (or other heated element), to another heat exchanger 822, which is in thermal contact with a phase change material, such as ice. The heat exchanger 822, together with the phase change material 810, can be coupled to the photocosmetic device in a removable and replaceable fashion. For example, upon a phase transition of the phase change material as a result of heat extracted from the circulating fluid, the heat exchanger and the phase change material can be removed from the photocosmetic device to be prepared for re-use in the device. For example, the heat exchanger together with the phase change material can be placed in an external freezer to cause a phase transition of the phase change material into a state suitable for extracting heat from the heat exchanger. A unitary structure can be utilized for housing the heat exchanger and the phase change material in thermal contact with one another. Alternatively, the heat exchanger 822 and the phase change material can be housed in separate enclosures that can be coupled together so as to provide good thermal contact between the heat exchanger and the phase change material.

Various exemplary implementations of the above embodiments are described below. It should be understood that the following embodiments are presented for providing further elucidation of salient features of the invention, and are not intended to be limiting of the types of implementations that can be employed to practice the invention.

Figure 9:
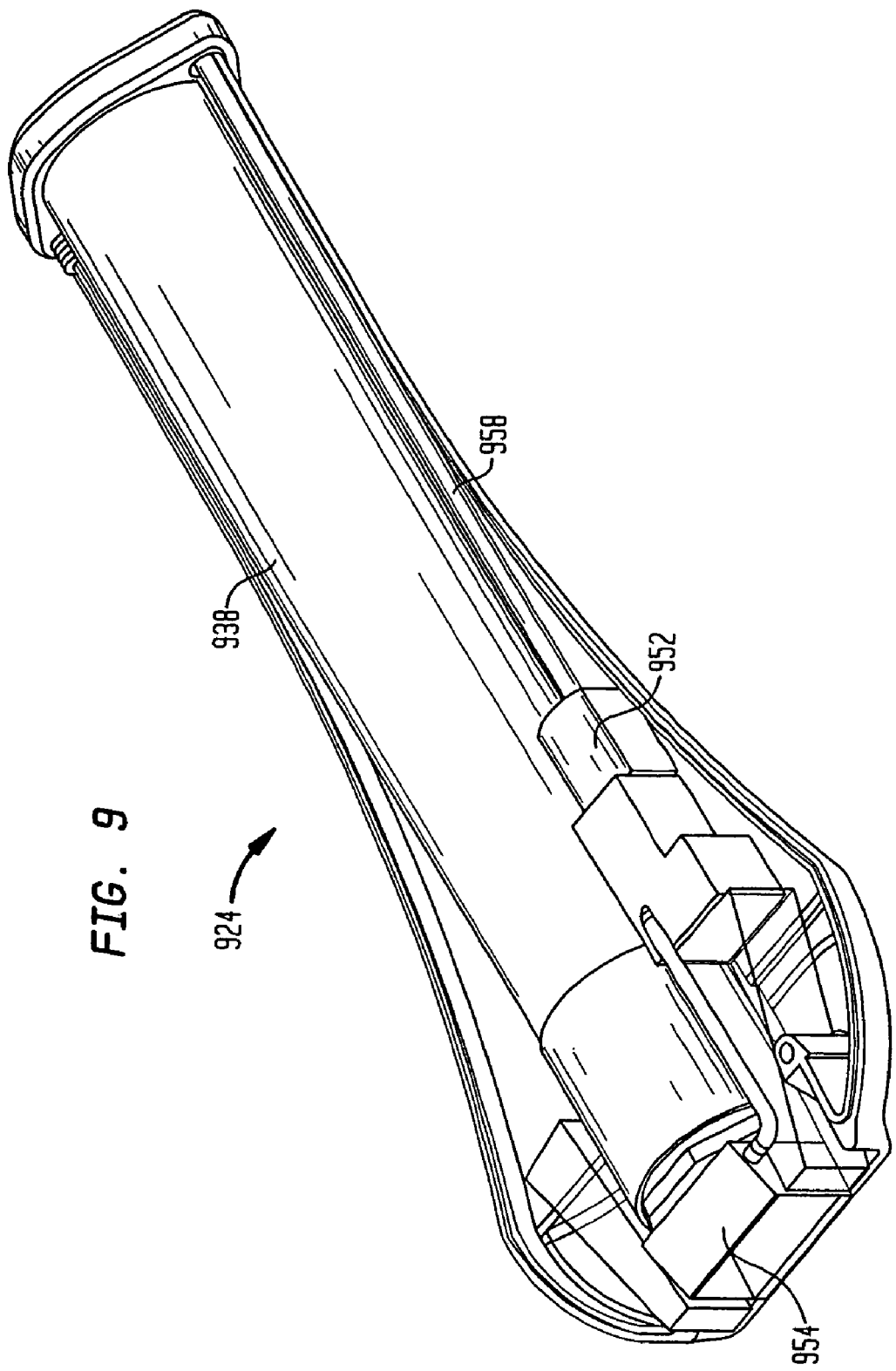
FIG. 9 is a cut-away, schematic perspective view of an exemplary handpiece of a photocosmetic device according to one embodiment of the invention.
Figure 10:
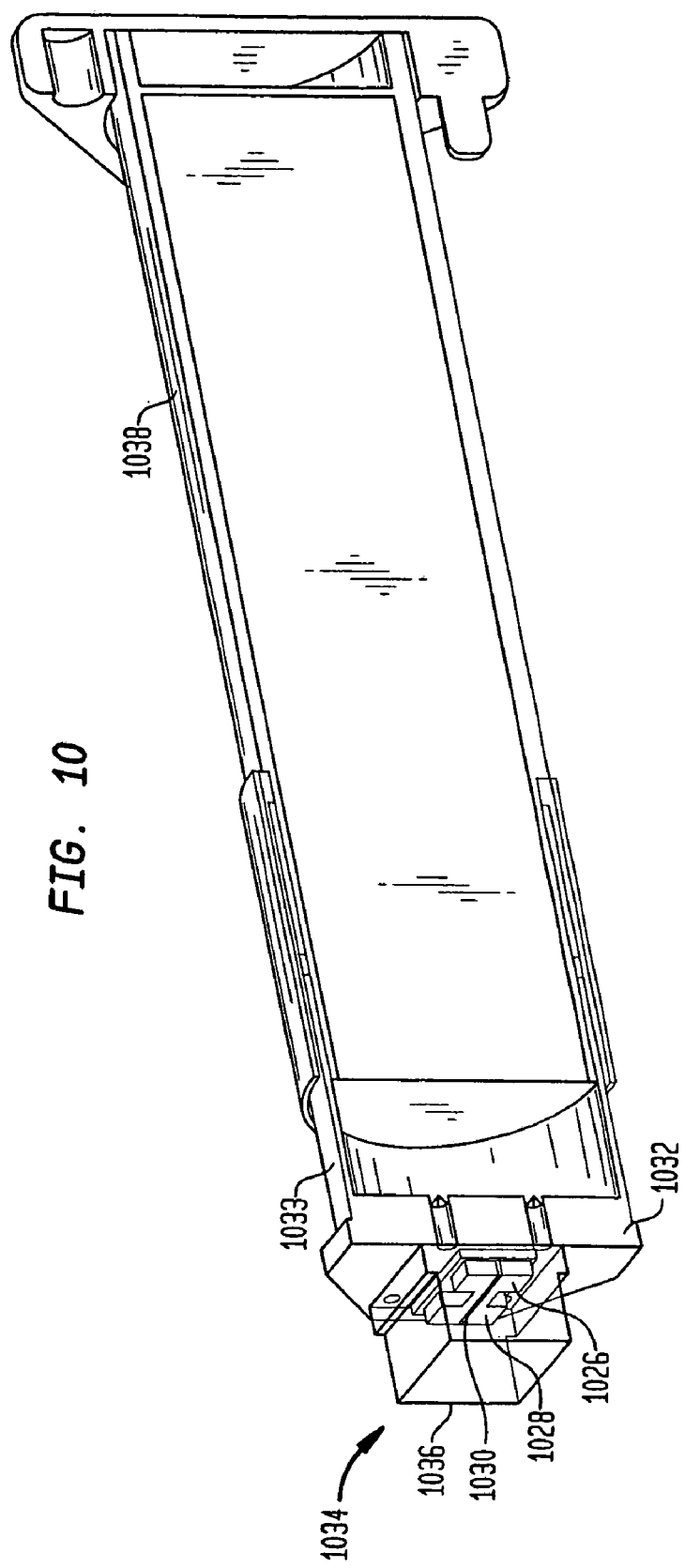
FIG. 10 is a cut-away view of an ice cartridge coupled to a heat sink of the handpiece shown in FIG. 9.

By way of example, with reference to FIG. 9 and FIG. 10, an exemplary handpiece 924 of a photocosmetic device according to one embodiment of the invention includes a light source 1026, e.g., a diode laser or LED or lamp, that is positioned between positive and negative electrodes 1028 and 1030 and is in electrical contact with these electrodes. The diode laser can be clamped between the two electrodes, or can be secured to the electrodes by any other suitable method that ensures good thermal and electrical contact between the diode laser and the electrodes, or only the positive electrode. The electrodes 1028 and 1030 supply electrical power to the diode laser, and are preferably formed of a material, e.g., copper, that has good thermal conductivity. The diode laser 1026 and/or the electrodes are in thermal contact with a heat transfer element 1032 (herein also referred to as a heat sink) that transfers waste heat generated by the laser to a phase change material, such as ice, as described in more detail below. The heat sink 1032 can be formed of any suitable material having good thermal conductivity. For example, the heat sink 1032 can be formed of copper, aluminum, diamond or any other suitable material.

The exemplary handpiece 924 further includes an optics assembly 1034 having an optical transmissive element 1036, for example, a sapphire window, that receives radiation emitted by the laser through an input surface, and delivers the radiation through an output surface to a portion of a patient, for example, a patient's skin. The input surface of the transmissive element is typically located at close proximity of the laser without having direct contact therewith (in some embodiments, the input surface can have direct contact with the light source). Further, the transmissive element is preferably in thermal contact with the heat sink 1032, and is formed of a thermally conductive material that allows removing heat from a portion of a patient's skin that is treated with radiation provided by the light source 1026.

The exemplary heat sink 1032 can couple to the diode laser 1026 and/or the electrodes 1028/1030. A tubular housing 1033, which extends from the heat sink block, can couple to a cartridge 938 in which a quantity of a phase change material, such as ice, is stored for cooling the heat sink 1032, as described in more detail below.

The handpiece 924 is typically connected via an umbilical cord (not shown) to a base unit (not shown) that can include, e.g., a power supply and associated electronics for powering the light source and providing selected control functions. Alternatively, the handpiece 924 may be the entire photocosmetic device including battery power.

The exemplary cartridge 1038, in which a phase change material is disposed, can be removably and replaceably coupled to the heat sink 1032 via the tubular housing 1033. The cartridge 1038 can hold a selected quantity of a phase change material, which in preferred embodiments of the invention is selected to be ice. As discussed above, ice is a particularly good choice for the phase change material because it exhibits a high latent heat of melting and is biologically and environmentally safe. It should, however, be appreciated that any other suitable phase change material can also be utilized in the practice of the invention. Further, skin beneficial ingredients can be added to the phase change material to be released onto a portion of the patient's skin during treatment of the skin by the photocosmetic device. Such ingredients can provide beneficial and/or therapeutic effects independent of the therapeutic effects provided by the exposure of the skin to light, heating or cooling provided by the photocosmetic device. Alternatively, the skin beneficial ingredients can be photo or thermally activated by the device to provide their intended beneficial effects. As discussed in more detail below, the cartridge 1038 can be a disposable element, or alternatively, can be a multi-use element.

Figure 11:
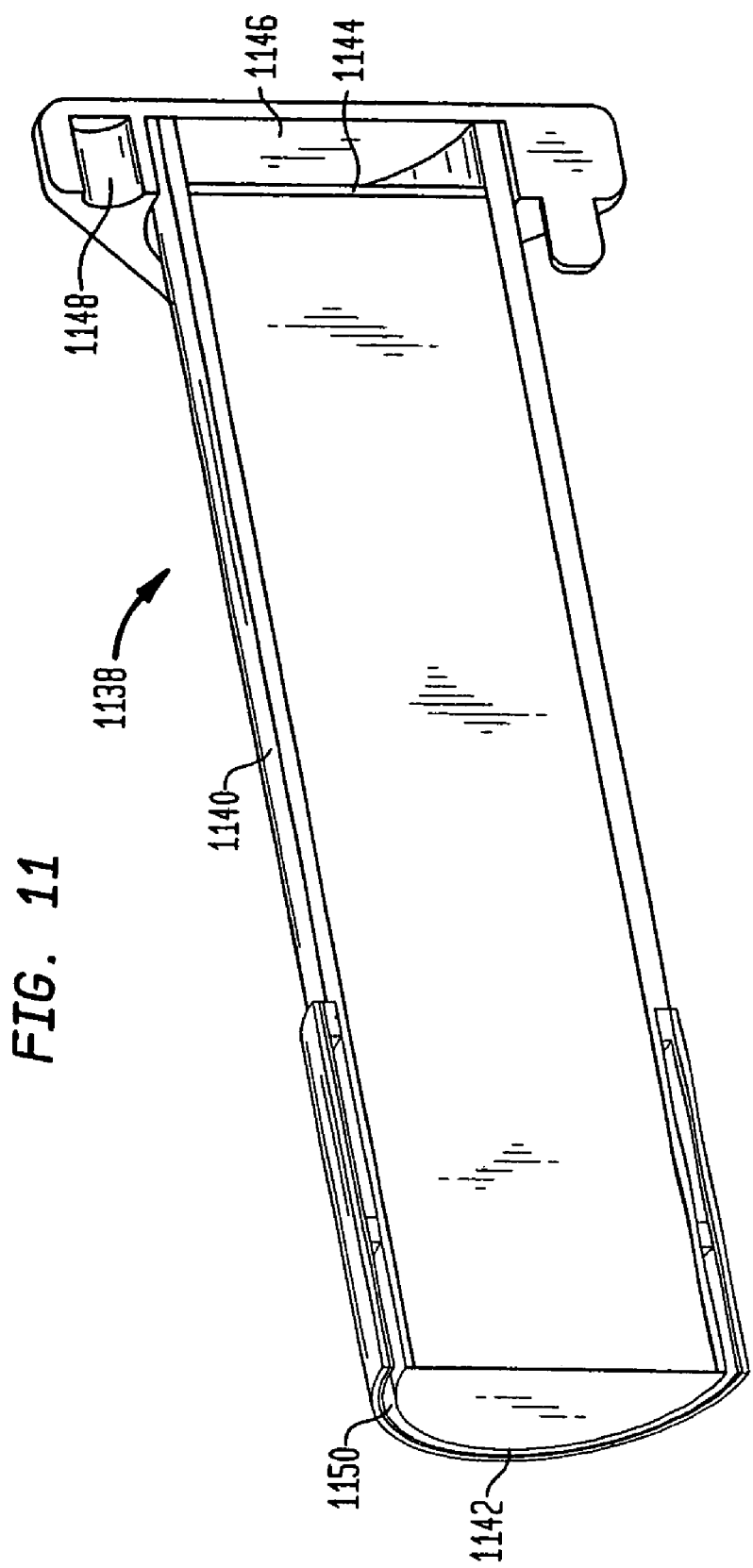
FIG. 11 is a cut-away view of the cartridge shown in FIG. 10 prior to its engagement with the heat sink.

With reference to FIG. 11, the exemplary cartridge 1138 has a generally cylindrical shape (circular, elliptical, rectangular) and includes a hollow tubular housing 1140 in which a quantity of ice, or other suitable phase change material, can be stored. A membrane seal 1142, which is disposed at a proximal end of the cartridge 1138, and another seal 1144, herein referred to as a piston seal, which is disposed at a distal end of the cartridge, cooperatively ensure that the ice remains confined within the cartridge before its engagement with the heat sink 1132. A volume 1146 disposed behind the seal 1144 provides a space for collecting water, via a liquid return port 1148, that is generated as a result of melting of the ice, as described in more detail below.

The membrane seal 1142 is attached to an annular sealing ring 1150 that can provide a seal between the cartridge 1138 and the heat sink 1132 upon coupling of the cartridge with the heat sink. The annular sealing ring 1150 and the membrane seal 1142 can be formed as two separate components and joined together, or alternatively, they can be formed as a unitary structure.

Figure 12:
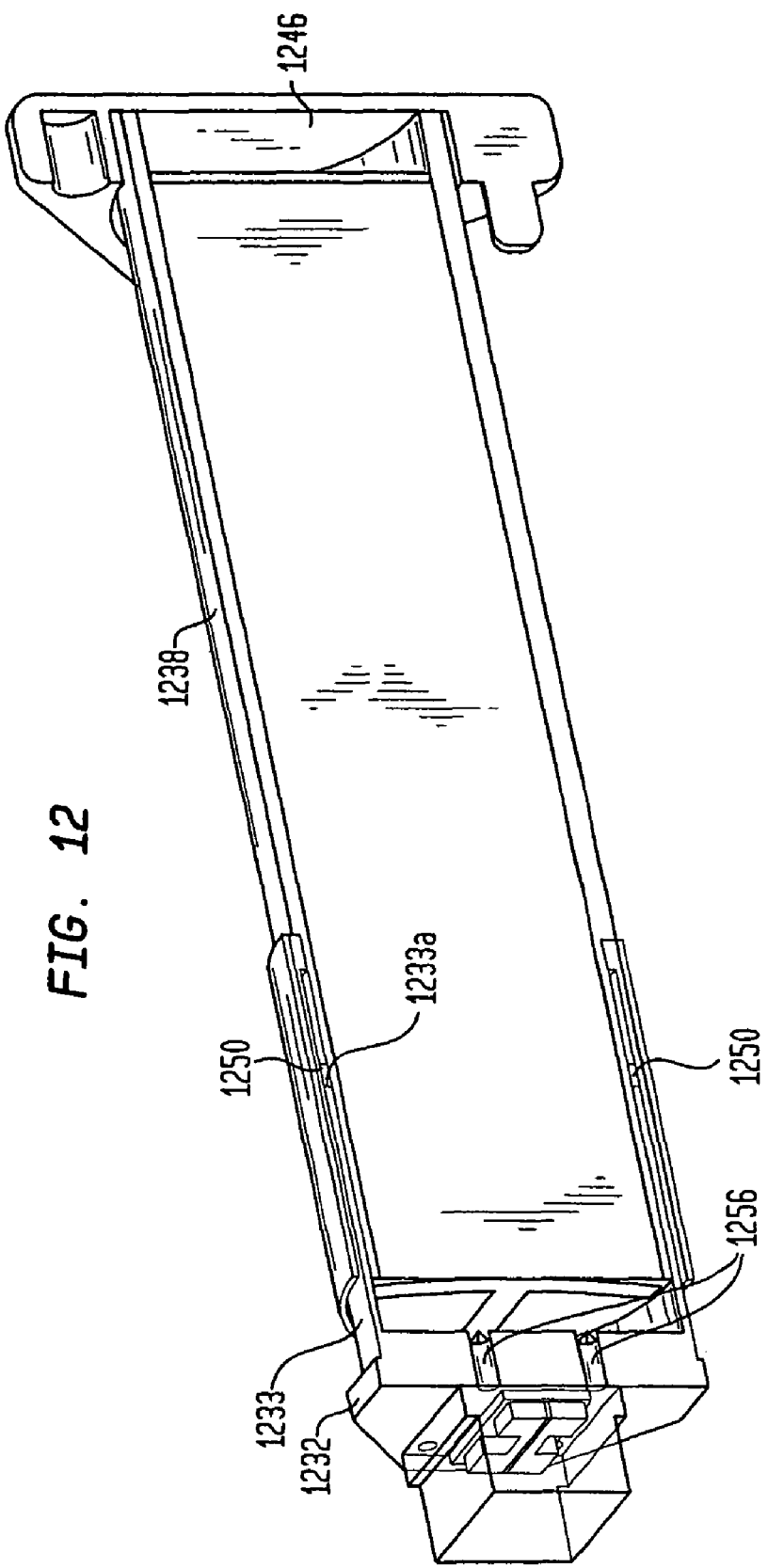
FIG. 12 schematically illustrates coupling of the cartridge of FIG. 11 with the heatsink of the handpiece of FIG. 10.
Figure 13:
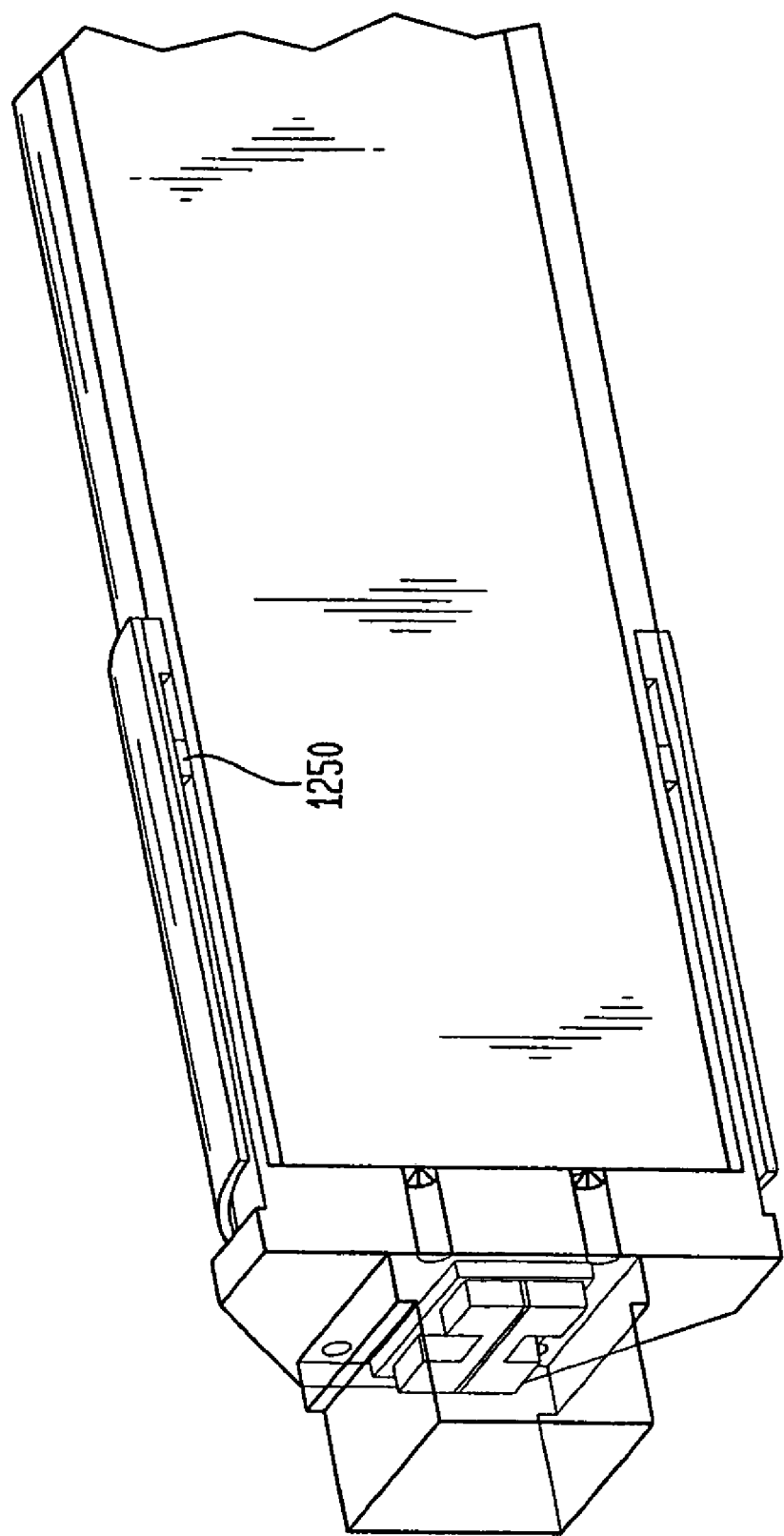
FIG. 13 schematically illustrates full engagement of the ice cartridge of FIG. 11 with the heat sink of the handpiece of FIG. 10.

Referring to FIG. 12 and FIG. 13, the cartridge 1238 can be inserted into the hollow tubular housing 1233 and pushed forward to fully engage with the heat sink. As shown in FIG. 12, as the cartridge is pushed forward, an edge 1233a of the tubular housing 1233 pushes back on the annular sealing ring 1250, thereby causing the membrane seal 1242 to tear and to move towards the annular sealing ring 1250. The tearing of the membrane seal 1242 exposes a surface of the ice, or other phase change material stored in the cartridge, initially covered by the membrane seal. Upon full engagement of the cartridge with the heat sink (FIG. 13), this exposed surface will be in thermal contact with a back surface of the heat sink block 1232 to allow heat generated by the light source to flow from the heat sink to the ice. The transferred heat causes melting of the ice at the ice-heat sink interface, thereby removing heat from the heat sink. In other words, melting of the ice provides the mechanism for dissipating the heat generated by the light source.

The surface of the heat sink that is in contact with the ice is preferably shaped so as to ensure a substantially uniform contact area between the ice and the heat sink at the ice/heatsink interface during operation of the handpiece. In general, this shape allows the contact surface to be a surface of constant temperature. For example, this heat sink surface may have a generally convex shape that substantially conforms with a generally concave shape of the corresponding ice surface. Those having ordinary skill in the art will appreciate that other shapes can also be utilized to optimize the ice/heat sink contact. In addition, this surface can include one or more ports, e.g., in the form of slits, for removing fluid (liquid or gas), generated as a result of phase transition of the phase change medium, from the interface of the heat sink and the phase change medium, thereby preventing formation of a liquid or a gas layer at this interface.

During operation of the handpiece, as heat from the light source is transferred to the ice via the heat sink 1232, water is generated at the ice/heat sink interface. To ensure that the heat sink is in contact with ice rather than water, in preferred embodiments of the invention, the ice cartridge is continuously or discrete translated towards the heat sink during operation and/or between operations of the handpiece. Further, the generated water is moved from the ice/heat sink interface to the volume 1246 at the distal end of the cartridge in a manner described in more detail below.

A number of mechanisms can be utilized for translating the ice cylinder towards the heat sink. Without limitation, such mechanisms can include: a) a spring pressing against the back of the ice cylinder at the distal end of the cartridge, e.g., pressing against the piston seal 1144, b) a motorized linear screw, c) a compound that reacts with the water collected in the volume 1146 to generate a gas, e.g., $CO_2$, to drive the ice forward with gas pressure, d) a foam, or other compound, disposed in the space 1146 whose volume expands at it absorbs water, e) a separate pressurized cylinder or pump that supplies gas for driving the ice forward by gas pressure, f) a permanent magnet or an electromagnet, g) a piezo motor, h) a motor, which mounted inside handpiece or main units and delivery pressure to melting substance through wire, i) pressure can be applied from the hand/fingers of operator with simultaneously activating of light sources, j) pressure from gas chamber heated by electronics or light sources. For example, for manual application of pressure, a portion of the handpiece 924 can be made of a flexible material or otherwise compressible. Cooling efficiency and temperature of light sources and skin can be regulated be changing of the pressure.

With reference to FIG. 9 and FIG. 12, the exemplary handpiece 924 further includes a vacuum/pressure pump 952 for pumping the water generated due to melting of the ice, or other fluid when a phase change material other than ice is employed, from the ice/heat sink interface, via a return manifold 954, to the volume 1246. More particularly, the pump 952 pumps the water through internal channels 1256 provided in the heat sink and via the return manifold 954 and the piping 958 into the space 1246 at the distal end of the cartridge. This advantageously allows a more efficient thermal contact between the remaining ice, which is translated forward to be in contact with the heat sink, and the heat sink.

Figure 14:
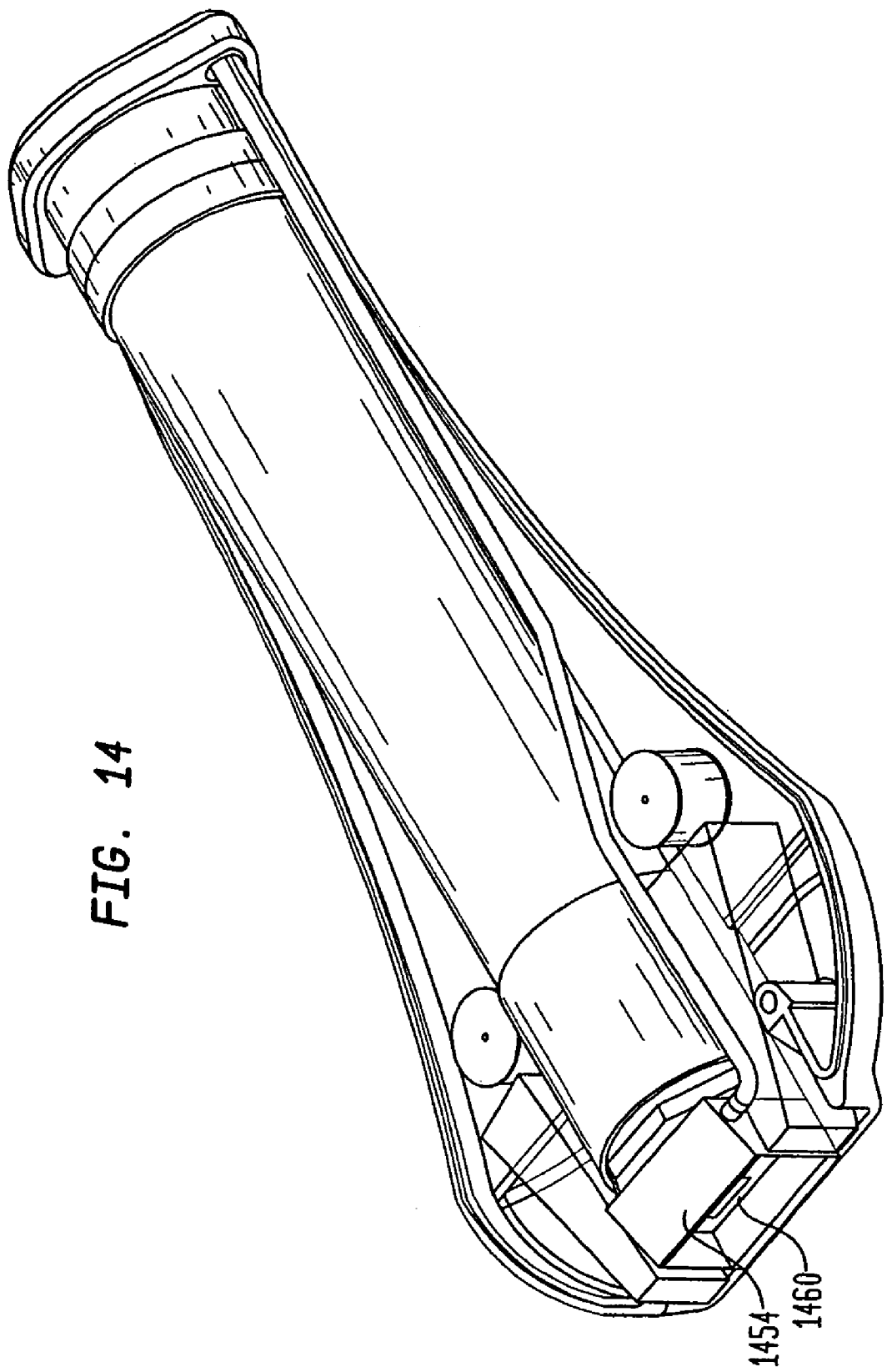
FIG. 14 schematically shows a handpiece of a photocosmetic device of the invention that allows diverting a portion of a liquid generated as a result of melting of a phase change material onto a treatment area of a patient's skin.

With reference to FIG. 14, in some embodiments of the invention, the return manifold 1454 can include a plurality of ports 1460 through which at least a portion of the water generated at the ice/heat sink interface can be diverted onto a portion of a subject's skin, which is under treatment via radiation provided by the handpiece. In addition, selected additives, such as various therapeutic, cosmetic or cleaning agents can be added to the water that is diverted onto the skin surface.

In this exemplary embodiment, the optically transmissive element 1036 of the optics assembly 1034 is in thermal contact with the heat sink 1032. This allows simultaneous cooling of the light source and the optical element 1036. During operation of the handpiece, the optical element 1036 can be in contact with a portion of a patient's skin. Hence, cooling of the optical element 1036 provides a mechanism for removing heat from the patient's skin to ensure that the temperature of the treatment area remains within an acceptable range, for example, below about 30° C.

In some embodiments of the invention, the laser diode 614, or other light source incorporated in the handpiece 924, may operate at a sufficiently high temperature such that heat transferred via the heat sink to the ice will not only cause melting of the ice into water but it may also cause evaporation of at least a portion of the generated water. The evaporation of the water, in other words, the phase transition of the water from a liquid phase to a gas phase, can help in removing heat from the heat sink. In some embodiments, the evaporation temperature of water can be decreased by lowering the ambient pressure in a volume in which water is generated as result of melting of ice, e.g., a volume at the interface of the heat sink and the ice. For example, a pump can provide a partial evacuation of air from this volume to lower the evaporation temperature.

Figure 15B:
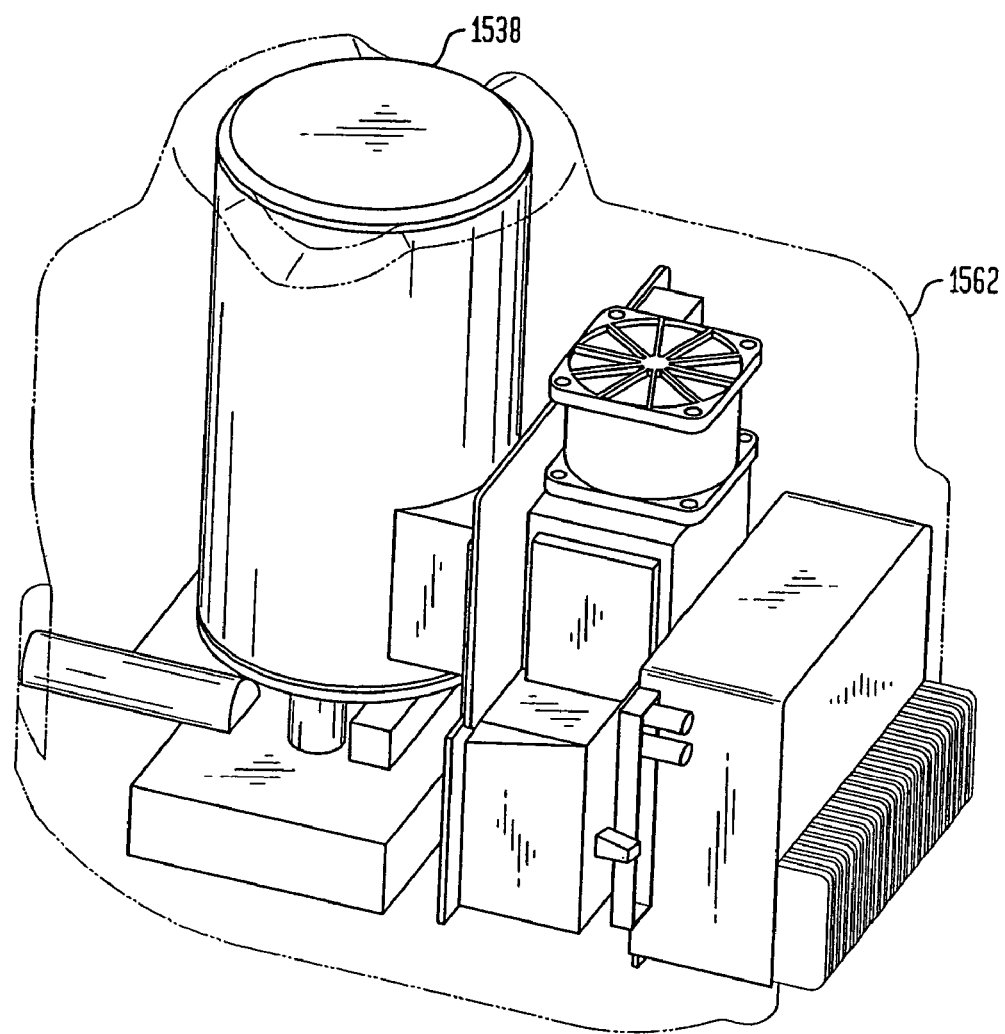
FIG. 15B is a schematic perspective view of another mechanism for cooling a cartridge containing a phase change medium.

The ice in the cartridge can be generated in a variety of different ways. For example, with reference to FIG. 15A and FIG. 15B, the cartridge can be designed to couple to a thermoelectric (TE) cooler 1561 provided in a base unit 1562 of the photocosmetic device. Alternatively, a TE cooler, adapted for coupling to the cartridge, can be provided in an accessory unit. In another approach, the ice can be generated by placing the cartridge in a freezer. Alternatively, a semi-permanent ice cartridge can be incorporated into the handpiece, and the entire handpiece can be placed in a freezer to freeze water disposed in the cartridge into ice.

The cartridge can be designed as a disposable unit that is discarded after one use. Alternatively, the cartridge can be utilized as a reusable unit.

Although in the above exemplary embodiment, the cartridge containing the phase change material is incorporated in the handpiece, in other embodiments, the heat can be transferred from the heated element in the handpiece to another module in which the transferred heat can be dissipated by causing the phase transition of a selected material, e.g., melting of ice, It should be understood that phase change materials other than ice can be employed in a manner described above to extract heat generated by the light source. For example, in some embodiments, a frozen mixture of water and an additive, such as salt or alcohol, is provided in the cartridge as the phase change material. Other examples of the phase change material include gallium and wax. In general, a suitable phase change material preferably exhibits a relatively high latent heat of melting to allow efficient heat dissipation, and is biologically safe. In addition, the phase change material is preferably safe for release into the surrounding environment.

In some embodiments of the invention, rather than utilizing the phase transition of a phase change material from a solid phase to a liquid phase, the sublimation of a phase change material, such as dry ice stored in the cartridge, from a solid phase to a gas phase is employed for removing heat from the light source.

Figure 16:
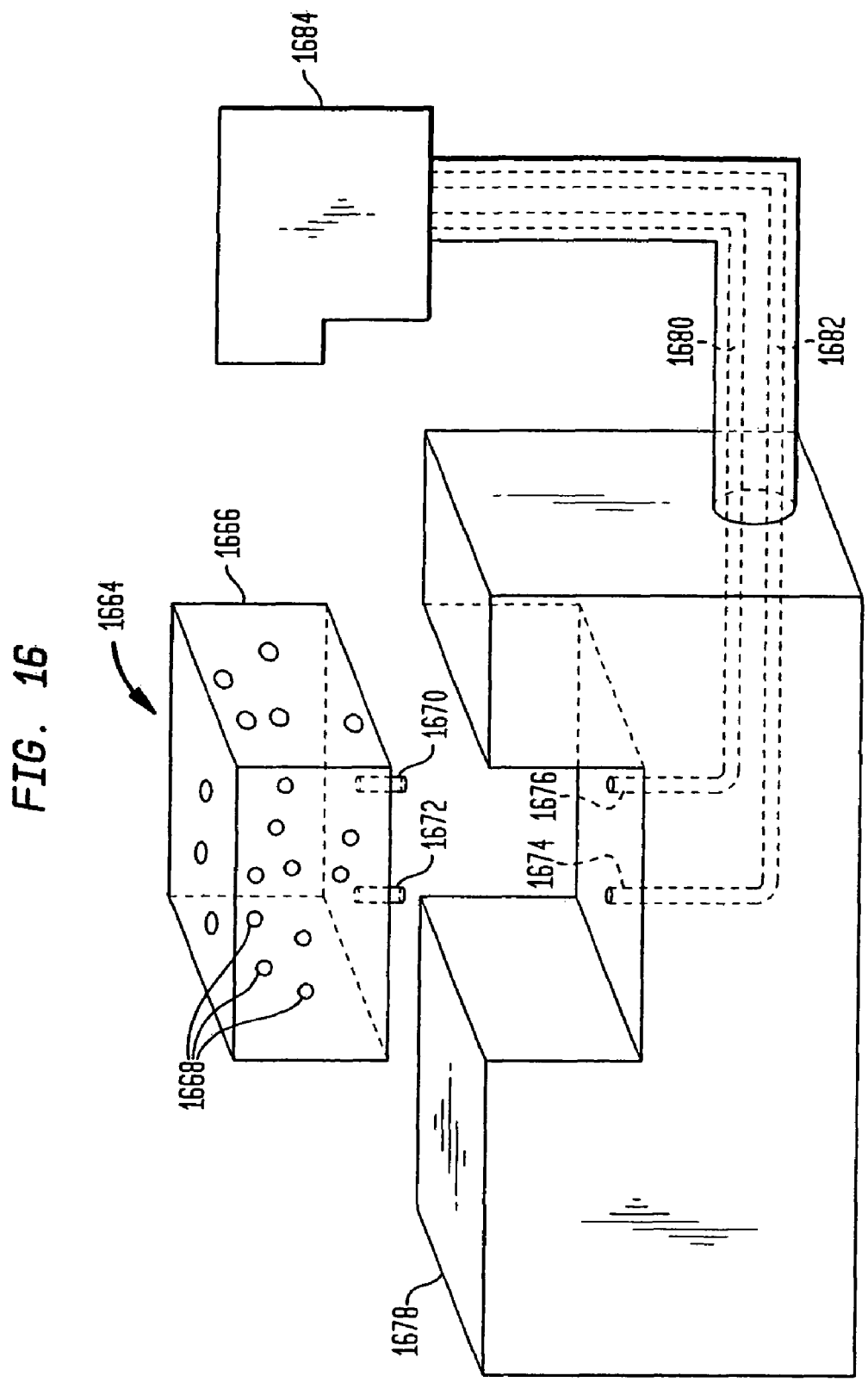
FIG. 16 is a block diagram that schematically illustrates a heat exchanger according to one embodiment of the invention that can removably and replaceably couple to a base unit of a photocosmetic device for cooling a fluid circulating between the base unit and a handpiece of the device for removing heat from a heated element incorporated in the handpiece.

In another aspect, the present invention provides a heat exchanger that utilizes a phase change material, such as, ice, for efficiently extracting heat from a heated element incorporated in the handpiece of a photocosmetic device. By way of example, FIG. 16 illustrates a heat exchanger 1664 according to one embodiment of the invention that includes a substantially hollow housing 1666, formed, for example, of metal or plastic. A plurality of structures 1668 having selected geometrical shape are disposed within the housing 1666. Each of the structures 1668 provides an enclosure for storing a selected quantity of a phase change material, such as ice. The structures can have a variety of different geometrical shapes, such as, spherical, cylindrical, or an elongated serpentine shape, or any other suitable shape. Further, the structures 1668 can have different sizes for storing different volumetric quantities of the phase change material. In general, the shapes and the sizes of these internal structures, which function as reservoir for a phase change material, are chosen so as to maximize their surface area to volume ratios, thereby enhancing the efficiency of heat exchange, as discussed in more detail below.

An internal volume of the heat exchanger 1664 surrounding the structures 1668 is filled with a fluid having a freezing temperature that is lower than the phase transition temperature of the phase change material contained within these structures. For example, when the phase change material is selected to be ice, the filling fluid can be a mixture of water and alcohol, or water in which a selected quantity of salt is dissolved, having a freezing temperature that is lower than the melting temperature of ice. As described in more detail below, during operation of the photocosmetic device, a cooling fluid that has extracted heat from a heated element of the device can circulate through the heat exchanger 1664, via ports 1670 and 1672 that allow ingress and egress of the cooling fluid into and out of the heat exchanger. The heat carried by the cooling fluid causes a phase transition of the phase change material contained within the structures 1668, thereby lowering the temperature of the cooling fluid, which can then be employed again to extract heat from the heated element.

More particularly, in this embodiment, the ports 1670 and 1672, which can include, for example, quick connectors, can engage with corresponding connectors 1674 and 1676, provided in a base unit 1678 of the photocosmetic device, in order to couple the heat exchanger to the base unit. Further, two lumens 1680 and 1682 extend from the base unit to a handpiece 1684 of the photocosmetic device, through an umbilical cord 1686, to provide passageways for circulating a cooling fluid, such as water, between the base unit and the handpiece. The circulating fluid extracts waste heat generated by a heated element disposed within the handpiece. Upon engagement of the heat exchanger 1664 with the base unit 1678, the cooling fluid flows from the lumen 1680, via the connector 1676 and the port 1670, into the heat exchanger 1664. The cooling fluid at a lower temperature exits the heat exchanger via the port 1672 and flows through the lumen 1682 to return to the handpiece for extract more heat from the light source. Alternatively, the ports 1670 and 1672 may engage connectors in the handpiece of the photocosmetic device.

Although in many embodiments of the invention, ice is employed as the phase change substance contained in the internal structures 1668, other materials can also be employed. Such materials can include, without limitation, various frozen solutions of water and selected additives, such as alcohol or salt, pure alcohol or any other suitable material. In all such cases, the fluid filling the heat exchanger's housing external to the structures 1668 should exhibit a freezing temperature that is lower than the phase transition temperature of the phase change material. In some embodiments, the structures 1668 can be partially filled with a liquid having a vaporization temperature that is above the room temperature but below the cooling temperature.

Further, in some embodiments, rather than utilizing the latent heat associated with melting of a phase change material for extracting heat from a cooling fluid circulating through the heat exchanger, the heat of sublimation of a material, such as dry ice, contained within the structures 1668 is utilized.

In other embodiments, the ambient pressure in the structures 1668 is lowered below the atmospheric pressure by partial evacuation of air from the structures so as to raise the phase transition temperature associated with a phase change material confined within the structures.

As discussed above, it is generally preferable to design the internal structures 1668 so as to maximize their surface to volume ratios. To this end, in some embodiments of the invention, the external surface of at least some of the structures 1668 exhibit a textured pattern to maximize the surface area that is in thermal contact with a cooling fluid flowing through the heat exchanger. The texturing of the surface can be accomplished, for example, by providing semispheres, cylinders, or pyramids projecting from the surface.

The heat exchanger 1664 can be prepared for use by employing a variety of different approaches. For example, the heat exchanger can be placed in a freezer for a selected duration to cause the phase transition of a phase change material disposed in the structures 1668 from a liquid phase to a solid phase, e.g., ice can be generated by freezing water contained in the structures 1668. Alternatively, the heat exchanger can be coupled to a TE cooler, or any conventional refrigeration mechanism, which can be provided in the base unit 1670 or in a separate stand-alone unit, to cool the heat exchanger.

With reference to FIG. 17, in another embodiment of the invention, a phase change material, such as ice, is provided within a cassette 1788 that can couple to a base unit 1790 of a photocosmetic device so as to bring the phase change material into contact with a heat exchanger within the base. As described in more detail below, the heat exchanger can include passageways for flow of a cooling fluid, e.g., water, that circulates between the base unit and a handpiece of the photocosmetic device in order to cool a heated element incorporated in the handpiece. Alternatively, the cassette 1788 may couple to the handpiece of a photocosmetic device.

Figure 18A:
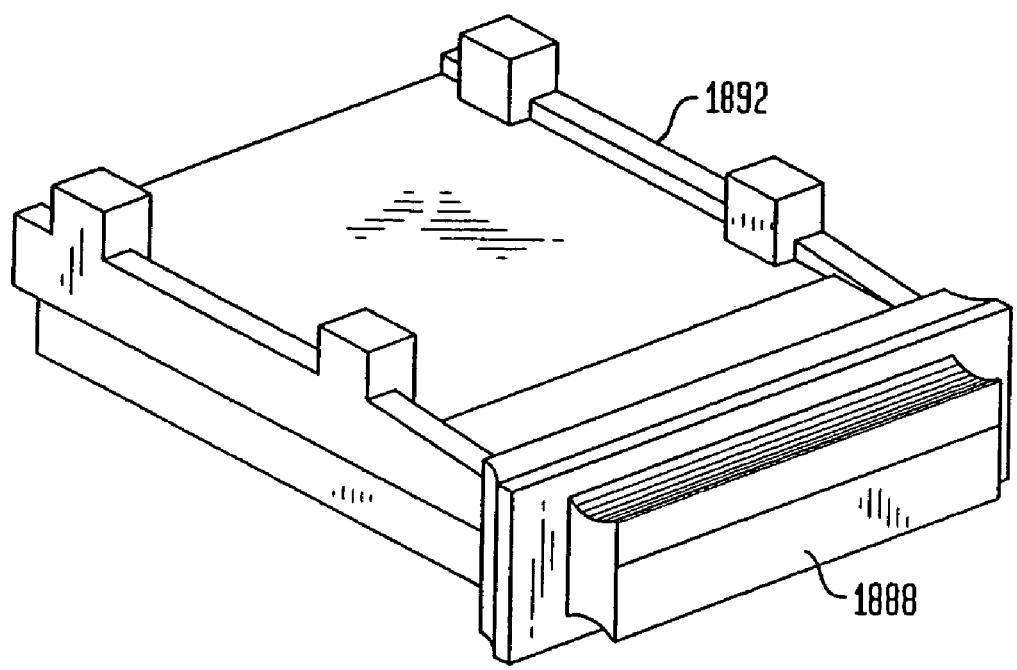
FIG. 18A is a schematic perspective view of the cassette of FIG. 17 coupled to a receiving module in a base unit of the photocosmetic device.

More particularly, with reference to FIG. 18A and FIG. 18B, the cassette 1888 can engage with a receiving module 1892, disposed within the base unit, in which a heat exchanger 1894 is incorporated.

Figure 19:
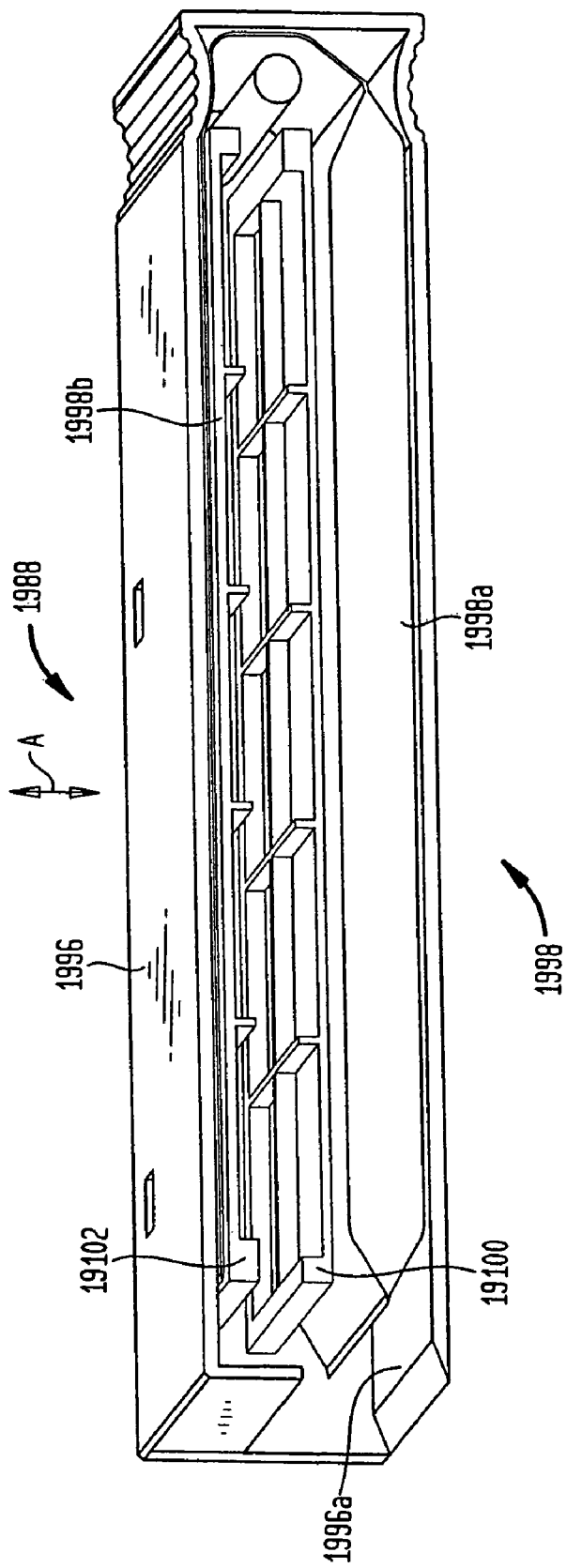
FIG. 19 is a cut-away perspective view schematically illustrating various components of the cassette of FIG. 18B.

FIG. 19 schematically illustrates various components of the exemplary cassette 1988 suitable for use in this embodiment of the invention. The illustrative cassette 1988 includes a housing 1996 in which a container (pouch) 1998 for storing a selected quantity of a phase change material is disposed. The container 1998 can be formed of a compliant material, such as plastic, having preferably good thermal conductivity. In this exemplary embodiment, the container 1998 includes a lower portion 1998a and an upper portion 1998b that surround two movable plates 19100 and 19102, which can move in a direction A to exert pressure on either the lower or the upper portions of the container 1998.

As shown in FIG. 18B and FIG. 19, prior to engagement of the cassette with the receiving module 1892, the pouch 1998 contains a selected quantity of ice, or other suitable material, while the upper portion of the pouch is empty. During formation of the ice in the pouch by freezing a selected quantity of water, the movable plate 19100 and a lower surface 1996a of the cassette's housing form a "mold" for generating a "brick" of ice while the movable plate 19102 squeezes the upper portion of the pouch to force any water remaining in the that portion to be transferred into the lower portion.

Figure 20:
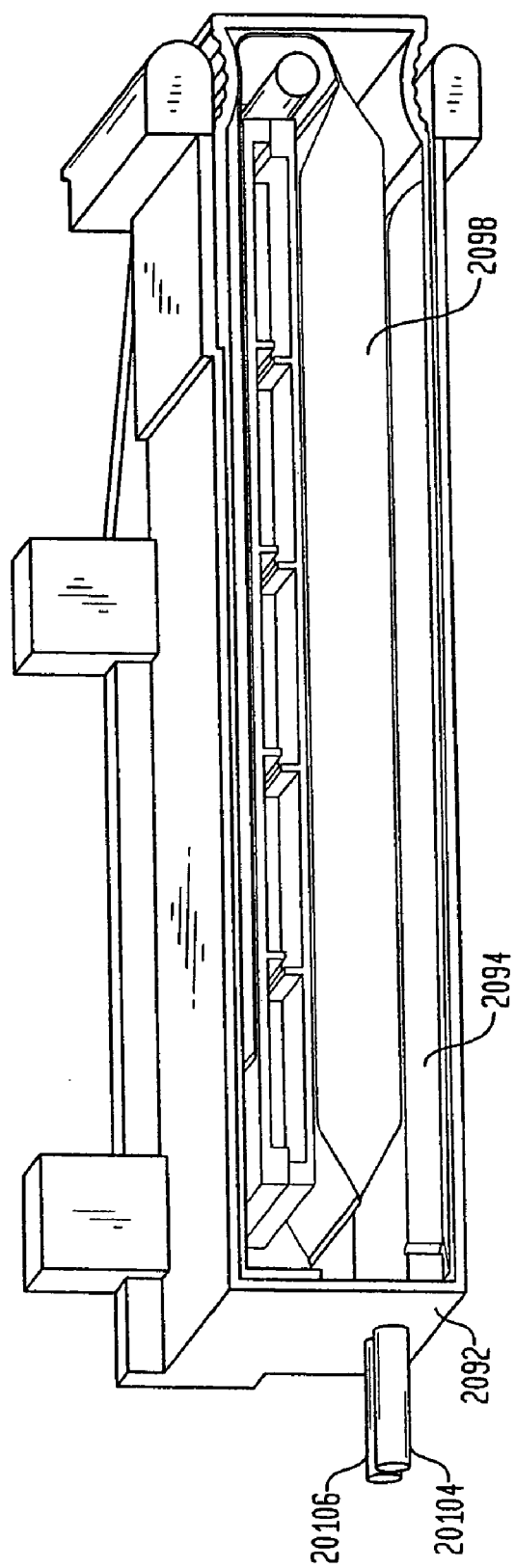
FIG. 20 illustrates coupling of the cassette of FIG. 19 with a heat exchanger provided in the receiving module of FIG. 18B.

With reference to FIG. 20, upon engagement of the cassette with the receiving module 2092, the ice block contained within the pouch 2098 will be in thermal contact with the heat exchanger 2094. The heat exchanger includes an ingress port 20104 through which a cooling fluid that has extracted heat from the heated element, disposed in the device's handpiece, flows into the heat exchanger. The thermal contact of the lower portion of the pouch 2098 with the heat exchanger causes the heat carried by the cooling fluid to be transferred to the ice contained within the pouch 2098, thereby causing it to melt. In other words, melting of the ice provides the mechanism for removing heat from the cooling fluid, thereby lowering its temperature. Meanwhile, the movable plates 20100 and 20102 apply pressure to the lower portion of the pouch in order to maintain good thermal contact between the pouch and the heat exchanger, and further to force water generated as a result of melting of the ice into the upper portion of the pouch.

Hence, as the cooling fluid flows through the internal passageways of the heat exchanger, it gives up heat to the ice in the pouch 2098, and it finally exits the heat exchanger at a lower temperature through an egress port 20106. The cooling fluid is then returned to the handpiece in order to extract heat from the heated element.

Figure 21:
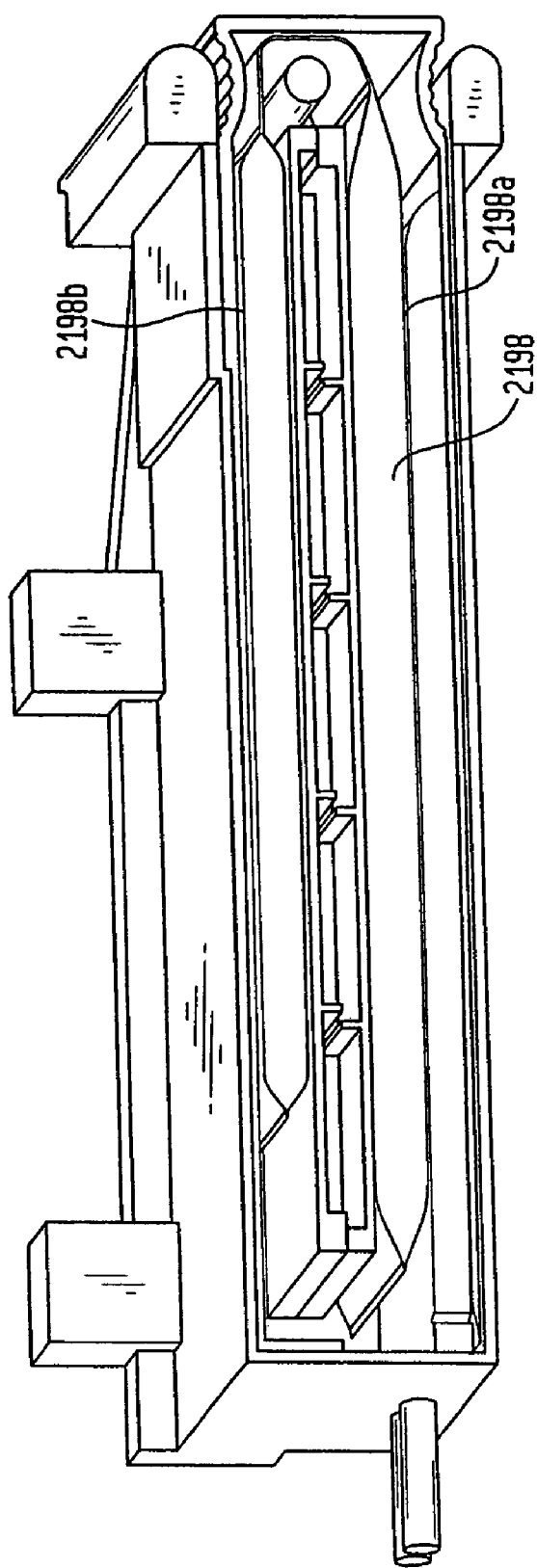
FIG. 21 schematically illustrates reduction of ice volume in a lower portion of an ice container of the cassette of FIG. 20 as the heat removed from a heated element of the photocosmetic device causes melting of the ice.
Figure 22:
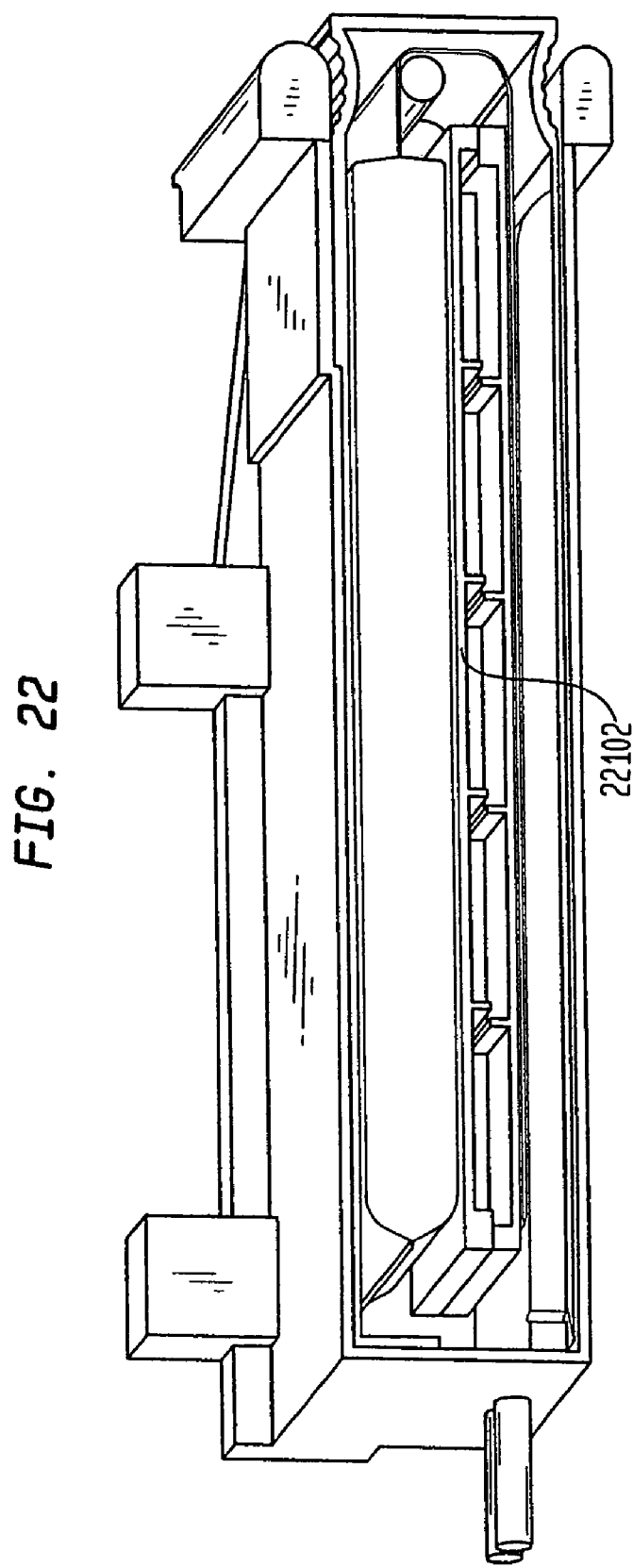
FIG. 22 schematically illustrates that upon melting of all of the ice in a lower portion of the container of FIG. 21, the generated water is accumulated in an upper portion of the container.

As shown in FIG. 21, as the ice melts, the volume of the ice within the lower portion 2198a of the pouch 2198 decreases while water continues to accumulate in the upper portion 2198b of the pouch. Finally, as shown in FIG. 22, the ice is used up and the generated water is collected in the upper portion of the pouch. The cassette can then be removed from the base unit. As the cassette is pulled out of the base unit, the plate 22102 applies a pressure to the upper portion of the pouch to cause transfer of the collected water into the pouch's lower portion. Hence, when the cassette is fully disengaged from the base unit, the water is accumulated in the lower portion, as shown previously in FIG. 19.

The formation of ice in the cassette can be accomplished by employing a number of different techniques. For example, a TE cooler can be provided in the base unit to which the cassette can couple in order to freeze water contained in the pouch. Alternatively, such a TE cooler can be provided in a separate accessory unit. In another approach, the cassette can be placed in a freezer for a selected time period to freeze water contained in the pouch into ice.

Figure 23:
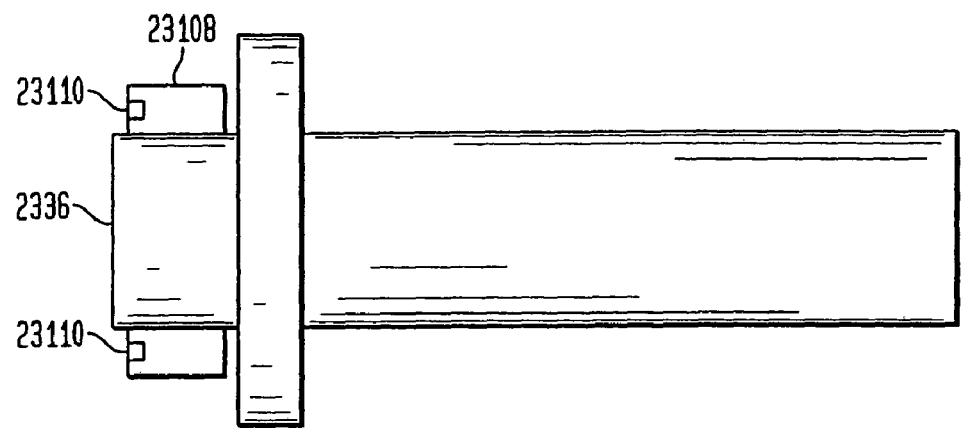
FIG. 23 schematically illustrates a cooling device for removing heat from an optical transmissive element of a handpiece of a photocosmetic device according to one embodiment of the invention.

In other aspects, the invention provides a cooling device that can be coupled to an optical transmissive element of the optics assembly of a handpiece of a photocosmetic device to remove heat therefrom. As shown in FIG. 23, in an exemplary embodiment, a cooling device 23108, herein also referred to as a heat exchanger, can surround the transmissive element 2336 to extract heat therefrom. The cooling of the transmissive element 2336 can in turn cause removing heat from (i.e., cooling) a portion of a patient's skin, which is in contact with a surface of the transmissive element during operation of the photocosmetic device, to ensure that the temperature of the treatment area remains within an acceptable range.

In one embodiment, the exemplary heat exchanger 23108 can be configured as a hollow sleeve that wraps around the transmissive element 2336 so as to be in thermal contact therewith. The sleeve, which is preferably formed of a thermally conductive material (e.g., copper), can contain a phase change material, such as ice or a vaporizable liquid, whose phase transition can be utilized in order to remove heat from the optical transmissive element. Preferably, the optical transmissive element is maintained at a temperature less than about 30° C. In addition, the sleeve can also be configured to directly remove heat from treated skin surface during operation of the photocosmetic device. Without any loss of generality, in the following description, the phase change material is assumed to be ice with the understanding that any other suitable phase change material can also be utilized. For example, in some embodiments, a frozen mixture of water and an additive, such as salt or alcohol, can be stored in the hollow sleeve.

Upon melting of the ice contained within the sleeve 23108, the generated water can be either released from the hollow sleeve onto the treatment area of the patient's skin or can be retained within the hollow sleeve. In some embodiments, the sleeve 23108 includes a plurality of openings, such as openings 23110, that allow introducing the water onto the treatment area. In other embodiments, therapeutic, cosmetic or cleaning agents can be added to the water to be also released onto the treatment area. Non-limiting examples of such additives include lotions, vitamins, aloe vera, petroleum jelly, oils, bee pollen, glycerin, moisturizers, preservatives, plant extracts, and fruit extracts. The openings can also be utilized for replenishing the phase change material in liquid form.

As discussed above, the hollow sleeve is preferably formed from a thermally conductive material, such as thermoconductive plastics or composite materials, ceramics, or metals. In some embodiments, the hollow sleeve can be formed of a semi-permeable or porous material such that, upon melting of the ice, the generated water can be selectively released onto the subject's treatment area. The pores can be configured to be sufficiently small such that the phase change material is dispersed onto the subject area only when in liquid form. Dispersal of the liquid can be controlled through the application of pressure, for example, during the movement of the transmissive element along the treatment area. More particularly, in some embodiments, a mechanism can be coupled to the sleeve to allow exerting pressure thereon as the transmissive element moves over the treatment area to facilitate introduction of the water and/or water mixed with therapeutic agents onto the skin.

Figure 24A:
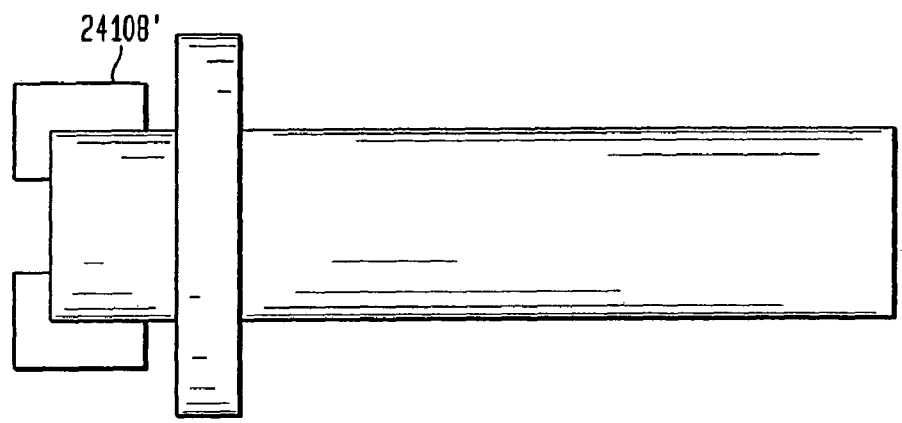
FIG. 24A and FIG. 24B schematically illustrate alternative implementations of the cooling device of FIG. 23.
Figure 24B:
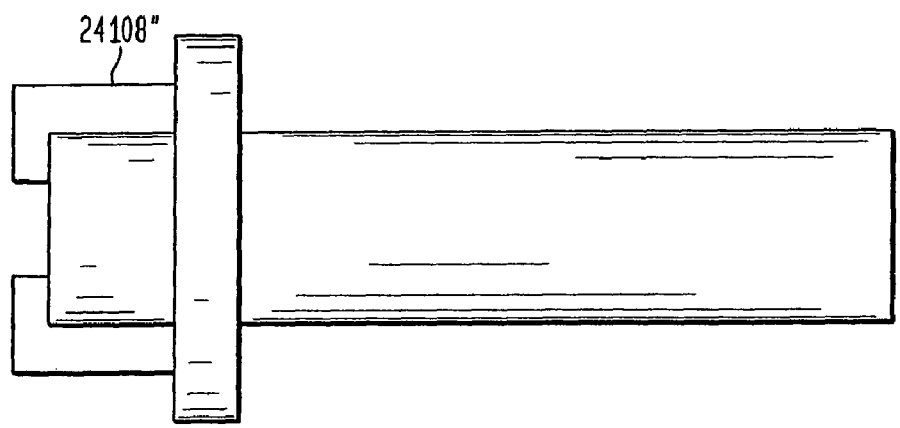

It is generally preferable to design the hollow sleeve so that its surface to volume ratio is maximized. For example, the hollow sleeve can be designed to substantially cover a peripheral outer surface area, i.e., the surface area other than the area facing the patient's skin, of the transmissive element. Alternatively, the hollow sleeve can be designed to substantially cover both the outer peripheral surface area of the transmissive element and/or partially cover the top face of the transmissive element (FIG. 24A), while still permitting optical radiation to be transmitted to the subject's treatment area. In another embodiment, the hollow sleeve can be designed to be in thermal contact not only with the transmissive element but also with the heat sink 2432 that is turn in thermal contact with a heated element (e.g., a light source) for removing heat therefrom (See FIG. 24B).

The hollow sleeve can be of various shapes. In general, the shape of the sleeve is complementary to that of the transmissive element to ensure good thermal contact therewith. For example, some suitable geometrical shapes for the hollow sleeve include, though are not limited to, a toroid having a circular, a rectangular, an oval or any other cross-sectional shape. The hollow sleeve can be configured to easily attach to and closely contact with the transmissive element. A number of mechanisms can be utilized to secure the hollow sleeve to the transmissive element and/or the heat sink. Non-limiting examples include: a) the hollow sleeve can be designed from a semi-elastic or elastic material that can slip over the transmissive element, forming a pressure fit with the transmissive element and/or the heat sink, b) the hollow sleeve can be hinged to the device such that the sleeve can clip onto the transmissive element and/or heat sink c) the hollow sleeve can have a cut-away portion that is complementary to a projection on the transmissive element.

In some embodiments, the hollow sleeve is disposable while in other embodiments, it can be recycled. For example, the sleeve filled with water, or other suitable material, can be placed in a freezer to generate ice. Alternatively, a stand-alone unit or a unit coupled to the device can be provided to house the hollow sleeve during regeneration, i.e., a freezing device into which the hollow sleeve selectively fits. In another embodiment, an additional element, e.g., a catalyst, can be added to either the hollow sleeve or the phase change material to initiate the phase change. In yet another example, the hollow sleeve can be designed to contain an inner tube that can be selectively filled with a material capable of initiating the phase change.

The surfaces of the transmissive element that receive light from the light source and/or are illuminated by light reflected from the treatment site are preferably formed of a material having a low coefficient of absorption of light in order to minimize heating of these surfaces.

IV. Safety Features

A. Markers

Aspects of the present invention are directed to providing safety feature to prevent misuse of the device. In one embodiment, the device is capable of detecting a treatment area. For example, in some applications, phototreatment devices are capable of being used only on the desired target area, i.e., a patient's tissue or skin, and not on other parts of the body (e.g., the eyes) thereby preventing potential injury to the user. Additionally, preventing use of a phototreatment device on an improper surface such as table, mirror, clothes, etc. may avoid damage to the device and injury to the user. According to embodiments of this aspect of the invention, a topical substance is deposited on a tissue to be treated and the topical substance or a marker within the topical substance is detected by a sensor in the phototreatment device so that the phototreatment device functions only if the topical substance or marker is detected, and preferably only if the topical substance or marker is determined to be on a tissue (e.g., skin). The topical substance and/or the markers may be detected, for example, using optical, electrical, magnetic, or acoustic detection techniques.

Two exemplary types of optical markers are absorptive and fluorescent markers. In some embodiments, a mild eye irritant is added to a topical substance or the marker, to deter a user from applying the topical substance on an eye.

In some embodiments of optical systems for detecting an area of treatment, a topical substance is applied to a tissue, a detection source provides light at a wavelength absorbed by the topical substance or an optical marker within the topical substance, and a detector is configured and arranged to detect a reflected portion of said light (i.e., light that is not absorbed). Preferably, the wavelength detected is close to the peak of absorption of the topical substance or optical marker, such that a reduction in the detected signal indicates the presence of the optical marker. In this embodiment, the optical detector is designed as a reflectometer to detect reflected light at a wavelength absorbed by the topical substance or optical marker.

Preferably, the topical substance or marker is characterized by an optical absorption spectrum substantially different from that of skin, to facilitate detection. Also, preferably, the absorption band of the topical substance or marker is outside the working spectrum of the phototreatment device, such that detection of the marker may be achieved without interference from source. Preferably, the optical density of the topical substance or marker is higher than the optical density of the skin for the light reflected from the patient's skin in the absorption band to facilitate detection of the topical substance or marker. The term "optical density" (OD) is defined herein to mean $$OD = -\ln\frac{I_r}{I_i},$$

where $I_i$ is the intensity of the incident light and $I_r$ is the intensity of registered light.

Figure 25A:
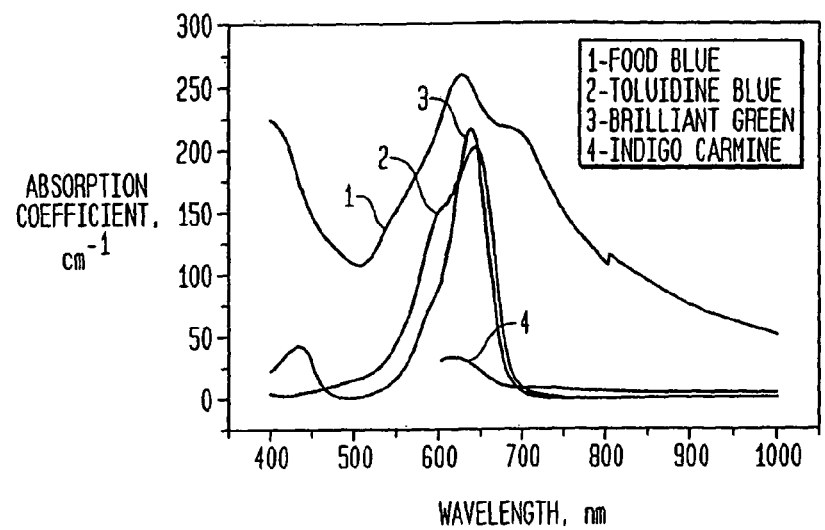
FIG. 25A is a graphical representation of absorption spectra for some exemplary dyes suitable for use as markers of areas to be treated.
Figure 25B:
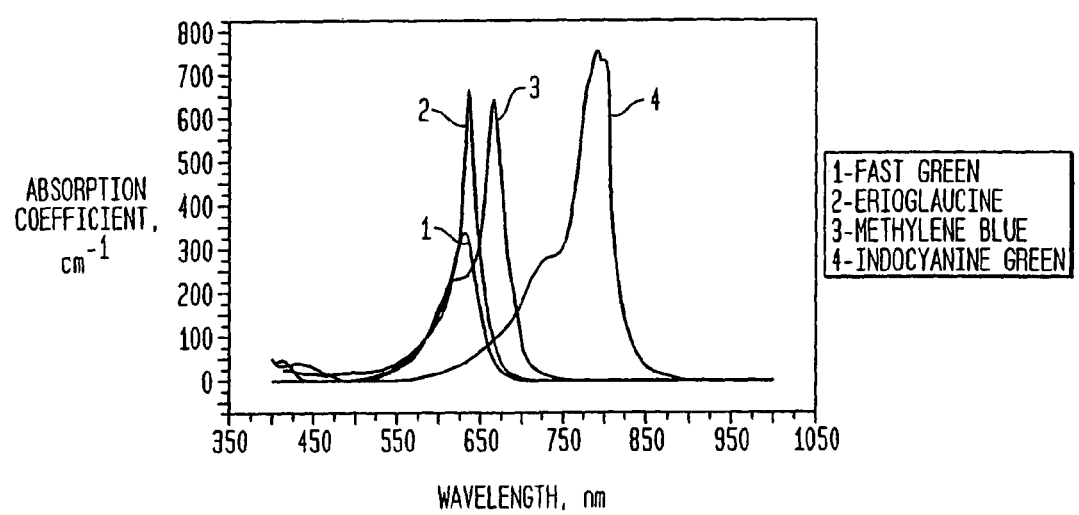
FIG. 25B is a graphical representation of exemplary absorption spectra for some exemplary, biocompatible dyes suitable for use as markers of areas to be treated.

FIG. 25A is a graphical representation of absorption spectra for some exemplary dyes suitable for use as markers of areas to be treated. The absorption spectra were taken using a UV spectrophotomer of dye solutions in glycerol with following concentrations: (1) 10 mg/ml Food Blue, (2) 1 mg/ml Toluidine Blue, (3) 1 mg/ml Brilliant Green, (4) 1 mg/ml Indigo Carmine. FIG. 25B is a graphical representation of absorption spectra for some exemplary, biocompatible dyes (1: Fast Green, 2: Erioglaucine, 3: Methylene Blue, 4; Indocyanime Green) suitable for use as markers of areas to be treated.

As shown in FIGS. 25A and 25B, Food Blue, Toluidine Blue, Brilliant Green, Indigo Carmine, Fast Green, Erioglaucine, Methylene Blue, and Indocyanine Green can be used as absorptive markers in combination with a suitable source (e.g., a 550-870 nm diode laser or 550-870 nm lamp). In addition to the markers indicated in FIGS. 25A and 25B, another class of absorptive markers is non-organic absorbers (e.g., carbon particles; china ink; compounds containing ions of Cu, Fe, Au, Ag, and Zn).

In some embodiments of systems for detecting areas of treatment, the reflectance is at two substantially different wavelengths, $\lambda_1$ and $\lambda_2$, where $\lambda_1$ lies within the absorption band of the topical substance or marker and $\lambda_2$ lies outside the absorption band. In such embodiments, a determination that a topical substance is located on a tissue may be determined when two conditions are fulfilled:

$$R_{min} < R_2 < R_{max},$$

$$\frac{R_1}{R_2} < A_T,$$

where $R_1$ and $R_2$ are the reflectance coefficients measured at the wavelengths $\lambda_1$ and $\lambda_2$, respectively; $R_{min}$ and $R_{max}$ are the minimal and maximal threshold values of the reflectance coefficients at wavelength $\lambda_2$, respectively; and $A_T$, is a threshold value of the reflectance ratio. Preferably, $R_{min}$ and $R_{max}$ are chosen to correspond to the physiological range of skin reflectance for $\lambda_2$. The above recognition algorithm is merely exemplary, and any other suitable detection algorithm may be used.

It is to be appreciated that if the peak of absorption shifts when the topical substance and/or marker is applied to or penetrates into the skin, the wavelength to be detected may be adjusted in such a way as to correspond to the shifted absorption peak. Such shifts may be used to provide additional assurance that the topical substance or marker has indeed been applied to skin.

As mentioned above, optical detection of an area to be treated may include a fluorescent marker. The term "fluorescence" is defined herein to encompass all types of non-elastic re-emission of electromagnetic energy, including (but not limited to) luminescence and Raman scattering. A "fluorescent marker" is any substance having at least one active ingredient characterized by fluorescence excitation.

Preferably, a fluorescent marker has an emission spectrum substantially different from that of skin. Also, preferably the fluorescent marker has a high quantum yield of fluorescence. Preferably, biocompatible fluorescent color additives are used as fluorescent markers. For example, suitable markers include Eosin Y; D&C Orange Nos. 5, 10, and 11; D&C Red Nos. 21, 22, 27, and 28; and Zinc sulfide.

In order to detect a fluorescent marker, a detection source is configured and arranged to provide light in the absorption band of the fluorescent marker, and a detector is configured and arranged to detect light emitted by the fluorescent marker. For example, the device may be a fluorimeter. In some embodiments, the fluorescent marker is illuminated with wavelength of light $\lambda_1$ which lies within the excitation band of the fluorescent marker, a resulting fluorescent signal is measured at wavelength $\lambda_2$ in the emission band of the fluorescent marker. In such embodiments, positive identification occurs when the following condition is fulfilled:

$$I_{12} > F_t,$$

where $F_t$ is a threshold value of the fluorescent signal. Other detection algorithms can be devised by those skilled in the art without departure from the scope of the present invention.

If one or both of the excitation band and emission band shifts when the optical marker is applied to or penetrates into the skin, the wavelengths $\lambda_1$ and $\lambda_2$ can be adjusted in such a way as to correspond to the shifted bands. A shift of a wavelength may be used to provide information related to the nature of the substrate (e.g., is the substrate skin or non-skin).

As indicated above, the topical substance or a marker within the topical substance may be detected through an electrical detector. For example, the topical substance or marker may have electrical conductivity (preferably, more than two-fold) higher than the maximal electrical conductivity of the skin. Examples of suitable topical substances or markers are conductive lotions and gels, such as: ALOE-STAT® CONDUCTIVE SKIN LOTION (Walter G Legge Company Inc), LECTRON 2 CONDUCTIVITY GEL and ELECTRO-MIST ELECTROLYTE SPRAY (Pharmaceutical Innovation), 3M CONDUCTIVE ELECTRODE GEL (3M Surgical Products Division). Some conductive lotions may penetrate into the skin. To detect an electrically conductive topical substance or marker, a phototreatment device may be equipped with a detector capable of detecting an electrical characteristic of the marker. For example, the detector may be a contact ohmmeter.

Also as indicated above, a topical substance or a marker within the topical substance may be detected through an acoustic detector. For example, a topical substance and/or marker may be designed to have an acoustical transmission resonance at a selected acoustic frequency, such that application of the topical substance and/or marker to the skin surface can change (e.g., dampen) the resonance of the topical substance and/or marker. In such embodiments, a phototreatment device may be equipped with an acoustic source (e.g., a piezo-electric crystal) and a transducer, such that a region covered with the topical substance and/or marker is identified when the acoustic signal exceeds a preset limit. For example, the detector may indicate that both of the following is true: 1) there is a signal at the resonance frequency (the film is present); and 2) said signal is dampened (i.e., the topical substance and/or marker is on a tissue).

As further indicated above, a topical substance or a marker within a topical substance may be detected through a magnetic detector. For example, the topical substance and/or marker may consist of or contain compounds with static or induced magnetic susceptibility. For example, magnetic microparticles, paramagnetic (FeO) and ferromagnetic ($CrO_2$, magnetite). Such compounds may be coated with a polymer (polystyrene) and, for example, the particles may have sizes of 3-10 µm (e.g., such a magnetic material is available from Spherotech, Inc.) or up to 1 µm (e.g., such a magnetic material is available from Polysciences, Inc). To minimize light absorption of magnetic particles in the working band of a phototreatment source, they can be coated by a highly reflecting metal such as Au, Ag, Cu, Al or by a multi-layer dielectric coating (Colored Magnetic Particles).

According to another aspect of the invention, additives can be advantageously included in a topical substance. The additives may provide a variety of effects. The following is an exemplary list of possible cosmetic additives: mineral oil, petrolatum, capric/caprylic triglyceraldehydes, cholesterol, lanolin, dimethicone/cyclomethicone, almond oil, jojoba oil, avocado oil, sesame oil, sunflower oil, coconut oil, grapeseed oil, glycerin (glycerol), propylene glycol, sorbitol, hyaluronic acid, lecithin, Urea, lactic acid, pyrrolidone carboxylic acid (NA-PCA), phospholipids, collagen, elastin, ceramide, vitamins A,B,C,D,E,K, hyaluronic acid, retinol, potassium hydroxide, or thyioglycolic acid.

Some additives interact synergistically with the phototreatment wavelength or wavelengths of light. Three exemplary mechanisms may be involved in the synergistic action of the device and the additives. First, the device may create a controlled profile of elevated temperature in skin, such that the transdermal penetration of the additive may be facilitated, and a higher concentration of an active compound(s) in the target area may be achieved. Second, a mild hyperthermia at the target site may increase the efficiency of an active ingredient(s) and, thus, enhance the desired effect. Third, an additive may be activated photochemically by the light emission of the device.

Figure 26:
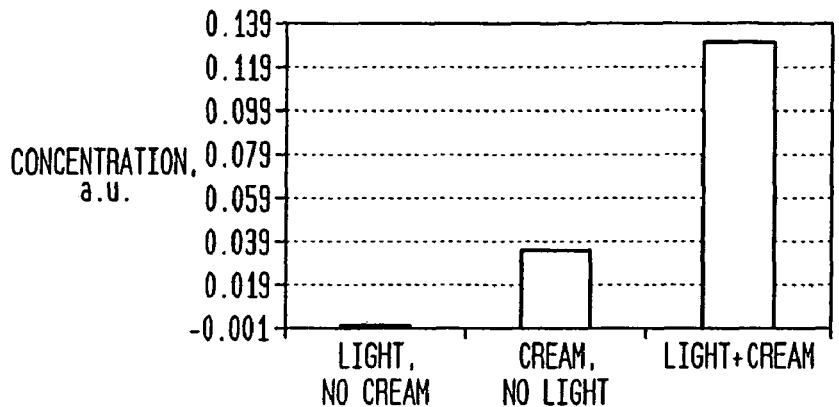
FIG. 26 illustrates photo-enhancement of transcutaneous penetration of a retinol-containing preparation observed in in vitro conditions.

FIG. 4 illustrates photo-enhancement of transcutaneous penetration of a retinol-containing preparation observed in in vitro conditions. Light with a wavelength of 800-2000 nm and flux 0.5 W/cm$^2$ was used in this experiment. The relative concentration of retinol, the active ingredient in the solution, after 30 minutes exposure to light was measured using UV absorbance. As shown in FIG. 26, the concentration of retinol is greatest when exposed to light.

B. Speed of the Device

Another aspect of the present invention is a motion sensor for determining the scanning speed of a phototreatment device. For example, an optical, electrical or magnetic marker may be used for detecting motion and/or determining scanning speed.

Figure 27:
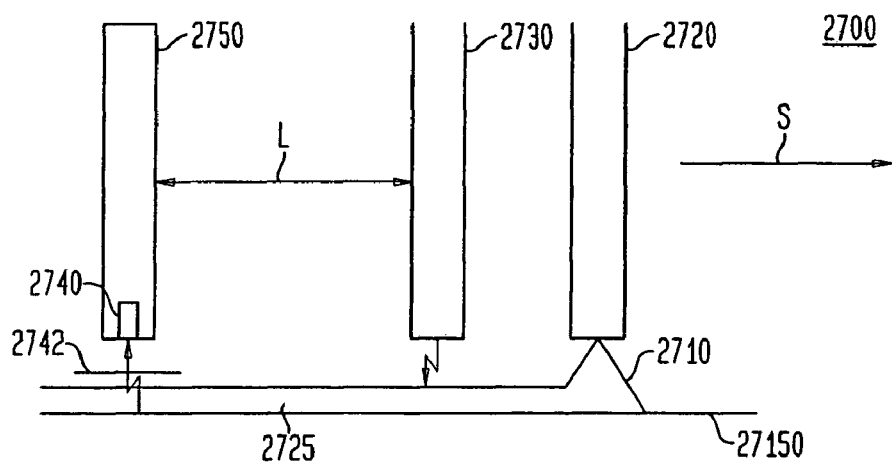
FIG. 27 is a schematic view of a system for measuring a speed of motion of a device on a tissue using a layer of marker material.

FIG. 27 is a schematic view of one example of a system 2700 for measuring a speed of motion S of a phototreatment device over a tissue 27150 using a topical substance or a marker 2710 added to a topical substance.

System 2700 may be located on a head of a phototreatment device such that as the head is moved across a patient's tissue 27150, the speed of motion S can be monitored. System 2700 comprises an applicator 2720 for applying a layer 2725 comprising topical substance and/or marker, and a detector system 2750 to detect a signal generated by layer 2725. As described below, the signal may be optical, electronic, or magnetic.

A detector system 2750 comprises a detector 2750 and suitable electronics to detect the signal generated by or in response to the layer 2725 and determine the speed of motion S at which the head is moving across tissue 27150. For example, the calculated speed may be used to control the fluence, wavelength(s) or pulse width of the light source, to control the application of a consumable substance, for display of speed S, or any other any other purposes. Further discussion of uses for a measured speed of motion S are given in U.S. application Ser. No. 10/154,756, incorporated by reference herein above.

Applicator 2720 is located to deposit layer 2725 onto tissue 27150. Applicator 2720 may be any known applicator capable of depositing a layer of material on a tissue. In some embodiments, applicator 2720 deposits a layer of uniform thickness.

The topical substance and marker may be any suitable materials capable of generating or responding to a suitable signal (e.g., optical, electrical or magnetic signal). In some embodiments, the material has a low enough viscosity to allow the material to be deposited by applicator 2720, and high enough viscosity, such that it remains on the tissue after deposit. Preferably, the material is easily removed by water and/or soap and water. Preferably, the topical substance and/or marker is index-matched to tissue 27150 to improve optical coupling of light from a source to the tissue (i.e., light from source 125 in FIG. 1A above) into tissue 27150.

In some embodiments, the topical substance and/or marker is a fluorescent material. Examples of appropriate fluorescent materials include those described above for use with consumable substances. Preferably the absorption band of the fluorescent material does not overlap with the wavelengths over which source 125 emits, to prevent interference.

Layer 2725 may be deposited using applicator 2720; however, in some embodiments of the invention, fluorescent topical substance and/or marker is applied by hand to form layer 2725; in such embodiments applicator 2720 may be omitted. In some embodiments, a fluorescent topical substance and/or marker is selected such that after applying the fluorescent topical substance and/or marker (e.g., by hand or any other suitable mechanism) and allowing it to remain for a predetermined time (e.g., 1-5 minutes), the fluorescent topical substance and/or marker may be removed as some of the fluorescent topical substance and/or marker will have penetrated the skin and still be detectable.

In some embodiments, a light projector 2730 projects a plurality of pulses of light onto layer 2725 having a wavelength in the absorption band of the fluorescent material to cause the fluorescent material to generate fluorescent light (i.e., to fluoresce). Light projector 2730 may be any LED, laser, lamp or any other known source of light capable of causing layer 2725 to generate fluorescent light. In some embodiments, the light pulses are uniform in intensity to generate uniform amounts of fluorescent light, and/or the pulses are generated at uniform intervals of time. Alternatively, the light may have any selected signal such that the signal has a known intensity (e.g., the signal may be a harmonic signal of known amplitude). Light projector 2730 may consist of a light source or may comprise a light source and focusing optics, beam steering optics, or any other suitable optical components.

In embodiments where the topical substance and/or marker is a fluorescent marker, detector 2740 is located to receive fluorescent light. Detector 2740 may be any detector sensitive to the fluorescent light emitted by fluorescent layer 2725 after light is projected onto it by the light projector 2730. Preferably, detector 2740 is a low electrical noise detector.

In some embodiments, detector 2740 is a known distance L from light projector 2730. Detector 2740 may measure an intensity using a single photosensitive element to determine the location of a peak intensity of the fluorescent light, or may have an array of photosensitive elements to determine the location of the peak intensity of the fluorescent light. In some embodiments, a band pass filter 2742 may be placed in front of detector 2740 to filter any extraneous light (i.e., any light other than fluorescent light emitted by fluorescent layer 2725).

Detector system 2750 is coupled to detector 2740 to calculate the speed of motion S. Speed of motion S may be calculated using any known method. In some embodiments, light projector 2730 projects pulses onto layer 2725, which are uniformly spaced in time, and detector system 2750 determines a time interval between peaks in the fluorescent light intensity as detected by detector 2740. By calculating a ratio of the distance L and the time interval between the peaks, speed of motion S may be determined. Alternatively, light projector 2730 may project pulses of light of known intensity, and the detector system 2750 measures the intensity of the peak detected by the detector 2740. If light projector 2730 generates a pulse of light having a known intensity and if fluorescent layer 2725 emits fluorescent light having a known intensity and a known decay rate, a time interval between the pulse of light produced by projector 2730 and time at which detector 2740 detects the light can be calculated. Because there is a known distance L between light projector 2730 and detector 2740, by calculating a ratio between distance L and time interval, a speed can be calculated.

In other embodiments, the detector 2740 need not be a known distance L from light projector 2730. Instead, the applicator deposits bands of fluorescent marker in a known pattern, having a known spacing. Accordingly, light projected onto the pattern by projector 2730 is modulated by the known pattern, so the speed can be calculated. For example, the known pattern may be formed by fluorescing molecules or particles at periodical parallel lines (bars) with period $\Delta$. When the handpiece is moved across the skin, the reflection signal is modulated with a period $P=\Delta/S$, so the speed can calculated as $S=\Delta/P$.

In other embodiments of system 2700, layer 2725 is a topical substance and/or marker that is absorptive of light from projector 2730. In such embodiments, projector 2730 provides light having a wavelength in the band of absorption of the absorptive layer 2725. Similar to the fluorescent layer system described above, projector 2730 may be a projector that provides periodic pulses or harmonics; however, in the present embodiment, detector 2750 may measure a reflected portion of light, or may measure heat generated by the absorption of light by the layer (e.g., the detector may be an infrared detector, a thermocouple, or a thermistor). Similar to the fluorescent topical system and/or marker system described above, the speed can be determined by measuring the time between pulses or using a known marker pattern.

In addition to optical topical substance and/or markers, electrical topical substance and/or markers may be used to measure speed of a phototreatment device. For example, a Hall sensor can be used as a motion sensor to detect magnetic field from the current flowing through the topical substance and/or marker. Current and voltage in the Hall sensor will be proportional to the current through the topical substance and to speed of motion S. Alternatively, a conductive pattern can be formed on the film as periodical conductive lines (bars). Using an electrical sensor (e.g., an ohmmeter), speed S can be determined as a ratio of the spatial period of the conductive pattern to the period of modulation of the signal from the ohmmeter.

Alternatively, a magnetic topical substance and/or marker may be used for measuring speed of a phototreatment device. Movement of the topical substance in the magnetic field can be detected as electromotive force in simple voltage sensor. A magnetic pattern can be formed on the film, for example, a pattern comprised of periodic magnetic lines (bars). In such embodiments, the electromotive force in the voltage sensor will be modulated with a period inversely proportional to speed S.

C. Visualizing the Treated Area

Figure 28:
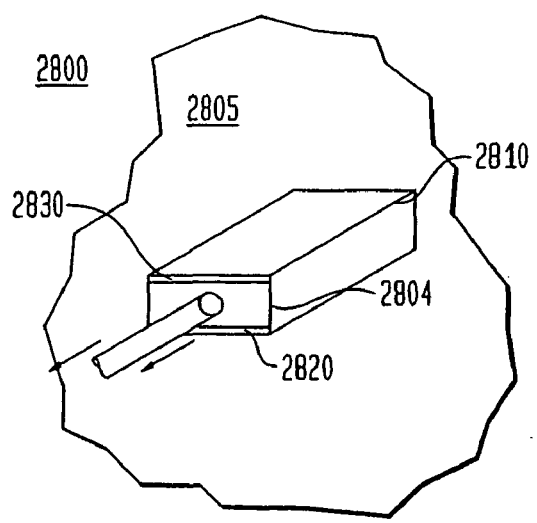
FIG. 28 is a schematic illustration of another aspect of the present invention directed to visibly indicating an area that has been treated.

FIG. 28 is a schematic illustration of another aspect of the present invention directed to visibly indicating an area that has been treated. Because treatment with a phototreatment device 2800 usually does not cause any visible change to the skin, a topical substance and/or marker 2810 may be deposited to provide a visual indication of areas that have been treated.

In some embodiments, a topical substance 2810 and/or marker having optical characteristics that are visible to an operator of the phototreatment device are deposited by an applicator coupled to the phototreatment device 2804. The applicator 2820 deposits the substance 2810 onto the tissue 2805 as the device is moved over a tissue region 2805, but prior to irradiation of the tissue region 2805 by the radiation source 2830 of the phototreatment device 2804. For example, the topical substance and/or marker 2810 can be comprised of a layer of lotion, gel, an adhesive wax, or a dye described above with reference to FIG. 25A and FIG. 25B may be used.

Alternatively, the topical substance and/or marker may be deposited by hand or any suitable device, and the topical substance and/or marker may be removed by the phototreatment device such that after the phototreatment device has passed over the tissue, the operator can visually discern the treated area. In some embodiments, the topical substance and/or marker has one or more optical characteristic that change after treatment (i.e., after exposure to phototreatment light). For example, the topical substances and/or marker may be invisible prior to exposure to the treatment light and become visible after treatment, or the topical substances and/or marker may be visible before treatment and become invisible after treatment (e.g., the topical substances and/or marker may be photo or thermally bleached). For example, suitable dyes can be selected from the polymethine, coumarine, or xanthene groups.

It is to be appreciated that although the aspects of the invention described in this application were described for use with a phototreatment device, aspects of the invention may have application in other types of devices that use consumable substances. Additionally, it is to be appreciated that, although consumable substances have been described as having been delivered through a replaceable container integrated with or attached to a phototreatment device, the consumable substances may be held within containers that are not non-integrated with and non-attached to a phototreatment device; in such embodiments consumable contents from a container may be directly applied to a tissue without passing through a phototreatment device.

D. Shut-Off Mechanism 40. In yet another aspect, the invention provides a system, having a radiation source, detector, and processor, for measuring a speed of motion of a phototreatment device over a tissue region, where the phototreatment device has an electromagnetic source to effect a phototreatment and the tissue region has a substance applied thereto. An applicator coupled to the phototreatment device can be used for depositing the substance onto the tissue prior to irradiation of the tissue region by the radiation source. The substance contains a marker. Non-limiting examples of markers include fluorescent markers, absorptive markers, electrical markers, optical markers, and magnetic markers. The radiation source is positioned on the phototreatment device to irradiate the tissue region and the applied substance. The detector is associated with the phototherapeutic device configured and arranged to monitor the substance. The processor calculates a speed of motion of the phototreatment device based on signals from the detector. The radiation source can be further coupled to the phototreatment device for irradiating a plurality of tissue locations and the substance is applied thereto as the device moves over the tissue region. The detector can be further coupled to the phototreatment device at a selected distance from the radiation source and arranged to monitor a response of the substance at an irradiated location subsequent to said irradiation. The processor can be further coupled to the detector for comparing said monitored response with a pre-selected value to determine a speed of motion of said phototreatment device.

The system can contain a comparator, for comparing the calculated speed of motion with a defined maximum speed value in order to determine when the calculated speed has exceeded a threshold established by the defined maximum speed. A preferred maximum speed in the 100-500 mm/sec range. A comparator can also be used for comparing the calculated speed of motion with a defined minimum speed value in order to determine when the calculated speed has fallen below a threshold established by the defined minimum speed. A preferred minimum speed is in the 10-100 mm/sec range. The system also contains a shut-off switch responsive to a control signal to terminate phototreatment when the speed has fallen below the threshold, thereby preventing injury to the user. For example, the control signal can enable the processor to control the electromagnetic source based on the speed of the phototherapeutic device. The shut-off switch can include a shutter that blocks the radiation and/or an alarm to alert the user.

Those skilled in the art will appreciate, or be able to ascertain using no more than routine experimentation, further features and advantages of the invention based on the above-described embodiments. Accordingly, the invention is not to be limited by what has been particularly shown and described, except as indicated by the appended claims. All publications and references are herein expressly incorporated by reference in their entirety.

The invention claimed is:

1. A method of operating a phototreatment device comprising:
    applying a marker to a region of tissue:
    detecting the marker; and
    enabling a function of the phototreatment device when the marker is detected; and
    disabling said function when said marker is not detected.

2. The method of claim 1, further comprising disabling said function until said marker is detected.

3. The method of claim 1, wherein the marker is one of an absorptive marker, a fluorescent marker, an electric marker, and a magnetic marker.

4. The method of claim 1, wherein the marker comprises at least one of Food Blue, Toluidine Blue, Brilliant Green, Indigo Carmine, Fast Green, Erioglaucine, Methylene Blue, and Indocyanine Green; carbon particles; china ink; Cu ions, Fe ions, Au ions, Ag ions, and Zn ions, Eosin Y; D&C Orange Nos. 5, 10, and 11; D&C Red Nos. 21, 22, 27, and 28; Zinc sulfide, ALOE-STAT® CONDUCTIVE SKIN LOTION, LECTRON 2 CONDUCTIVITY GEL, ELECTRO-MIST ELECTROLYTE SPRAY, 3M CONDUCTIVE ELECTRODE GEL, FeO, $CrO_2$, and magnetite.

5. A container for use with a photocosmetic device, comprising:
    at least one compartment defining an interior cavity and configured to contain a substance for use with the photocosmetic device;
    an opening in fluid communication with the interior cavity of said compartment and configured to be coupled to a phototreatment device; and
    a detection mechanism configured to be coupled to a corresponding detection mechanism of the photocosmetic device.

6. The container of claim 5, wherein the compartment is fluidly coupled to a head of a phototreatment device.

7. The container of claim 5, wherein the compartment is fluidly coupled to a heat dissipating element in a phototreatment device.

8. The container of claim 5, wherein the compartment is in fluid communication with a tissue.

9. The container of claim 5, wherein the detection mechanism is one of a mechanical mechanism, an optical mechanism, a magnetic mechanism, an electronic mechanism, and a piezoelectronic mechanism.

10. The container of claim 5, wherein the detection mechanism indicates an aspect of the container.

11. The container of claim 5, wherein the detection mechanism indicates an aspect of the substance.

12. The container of claim 5, wherein the container is detachable from the photocosmetic device.

13. The container of claim 5, wherein the container is configured to be refillable.

14. The container of claim 5, wherein the container is configured to be reusable.

15. The container of claim 5, wherein the container is configured to be removable.

* * * * *